US011136552B2

(12) United States Patent
Ko et al.

(10) Patent No.: US 11,136,552 B2
(45) Date of Patent: Oct. 5, 2021

(54) METHOD FOR REDUCING DIFFERENTIATION RESISTANCE OF PLURIPOTENT STEM CELLS

(71) Applicant: KEIO UNIVERSITY, Tokyo (JP)

(72) Inventors: Minoru Ko, Tokyo (JP); Tomohiko Akiyama, Tokyo (JP)

(73) Assignee: KEIO UNIVERSITY, Tokyo (JP)

(*) Notice: Subject to any disclaimer, the term of this patent is extended or adjusted under 35 U.S.C. 154(b) by 436 days.

(21) Appl. No.: 15/770,634

(22) PCT Filed: Oct. 28, 2016

(86) PCT No.: PCT/JP2016/082152
§ 371 (c)(1),
(2) Date: Apr. 24, 2018

(87) PCT Pub. No.: WO2017/073763
PCT Pub. Date: May 4, 2017

(65) Prior Publication Data
US 2020/0048612 A1 Feb. 13, 2020

(30) Foreign Application Priority Data

Oct. 28, 2015 (JP) ............................. JP2015-211356

(51) Int. Cl.
C12N 5/0775 (2010.01)
C12N 15/09 (2006.01)
C12N 5/074 (2010.01)

(52) U.S. Cl.
CPC ......... *C12N 5/0662* (2013.01); *C12N 5/0696* (2013.01); *C12N 15/09* (2013.01); *C12N 2501/60* (2013.01); *C12N 2502/45* (2013.01); *C12N 2503/02* (2013.01); *C12N 2506/02* (2013.01); *C12N 2506/45* (2013.01); *C12N 2510/00* (2013.01)

(58) Field of Classification Search
CPC .............. C12N 5/0662; C12N 2510/00; C12N 2506/45; C12N 2506/02; C12N 2501/60; C12N 15/09
See application file for complete search history.

(56) References Cited

U.S. PATENT DOCUMENTS

| 2013/0302893 A1 | 11/2013 | Pei et al. |
| 2015/0275171 A1 | 10/2015 | Kato et al. |

FOREIGN PATENT DOCUMENTS

| JP | 2009-045004 A | 3/2009 | |
| WO | WO-2014069479 A1 * | 5/2014 | ........... C12Y 114/11 |

OTHER PUBLICATIONS

Thoma et al., Ectopic expression of neurogenin 2 alone is sufficient to induce differentiation of embryonic stem cells into mature neurons. PLoS One, vol. 7, No. 6 (2012) e38651. (Year: 2012).*
Burchfield et al., JMJD3 as an epigenetic regulator in development and disease. The International Journal of Biochemistry & Cell Biology, vol. 67 (online Jul. 17, 2015) pp. 148-157. (Year: 2015).*
Takayama et al., Generation of metabolically functioning hepatocytes from human pluripotent stem cells by FOXA2 and HNF1α. Journal of Hepatology, vol. 57, No. 3 (Sep. 2012) pp. 628-636. (Year: 2012).*
Oh et al., Directed differentiation of pluripotent stem cells by transcription factors. Molecules and Cells, vol. 42, No. 3 (2019) pp. 200-209. (Year: 2019).*
Huang et al., JMJD3 acts in tandem with KLF4 to facilitate reprogramming to pluripotency. Nature Communications, vol. 11 (2020) pp. 1-16. (Year: 2020).*
International Search Report and Written Opinion issued in corresponding International Patent Application No. PCT/JP2016/082152 dated Jan. 24,2017 (7 pages).
Akiyama et al., "Transient ectopic expression of the histone demethylase JMJD3 accelerates the differentiation of human pluripotent stem cells," Development, 2016, pp. 3674-3685, vol. 143.
Correa-Cerro et al., "Generation of mouse ES cell lines engineered for the forced induction of transcription factors," Scientific Reports, 2011, pp. 1-6, vol. 1, No. 167.
Dey et al., "The Histone Demethylase KDM5b/JARID1b Plays a Role in Cell Fate Decisions by Blocking Terminal Differentiation," Molecular and Cellular Biology, 2008, pp. 5312-5327, vol. 28, No. 17.
Goto, "Analysis of time-dependent fate control mechanism of neural stem cells," Research Reports of Uehara Memorial Foundation, 2008, pp. 1-3, p. 1, vol. 22 (machine translation attached).
Nishiyama et al., "Uncovering Early Response of Gene Regulatory Networks in ESCs by Systematic Induction of Transcription Factors," Cell Stem Cell, 2009, pp. 420-433, vol. 5.
Torres et al., "Utx Is Required for Proper Induction of Ectoderm and Mesoderm during Differentiation of Embryonic Stem Cells," PLOS One, 2013, pp. 1-15, vol. 8, Issue 4.
Wang et al., "Histone demethylase KDM2B inhibits the chondrogenic differentiation potentials of stem cells from apical papilla," Int. J. Clin. Exp. Med., 2015, pp. 2165-2173, vol. 8, No. 2.
Xiang, "JMJD3 is a histone H3K27 demethylase," Cell Research, 2007, pp. 850-857, vol. 17.
Yamamizu et al., "Identification of Transcription Factors for Lineage-Specific ESC Differentiation," Stem Cell Reports, 2013, pp. 1-15, vol. 1.
Yamamizu et al., "Development of a differentiation induction method from pluripotent stem cells to arbitrary cells using transcription factor," Experimental Medicine, 2015, pp. 239-246, p. 242, vol. 33, No. 2 (machine translation attached).
Zasshi, "Establishment of a Method of Hepatocyte Differentiation from Human Pluripotent Stem Cells for Innovation Drug Development," 2015, pp. 1141-1146, p. 1142, vol. 135, No. 10 (machine translation attached).

* cited by examiner

*Primary Examiner* — Kara D Johnson
(74) *Attorney, Agent, or Firm* — Kilyk & Bowersox, P.L.L.C.

(57) ABSTRACT

In related-art methods of differentiating pluripotent stem cells into a desired cell type, there has not been established a differentiation induction method using human ES/iPS cells and being stable and highly efficient. A method of inducing differentiation into a desired cell type within a short period of time and with high efficiency by attenuating differentiation resistance of a pluripotent stem cell to generate a pluripotent stem cell that actively proceeds to a differentiated cell type has been found, and thus the present invention has been completed.

7 Claims, 10 Drawing Sheets

Specification includes a Sequence Listing.

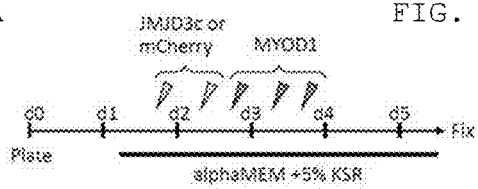
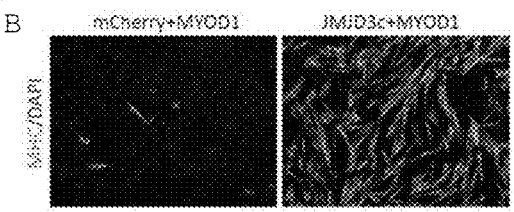
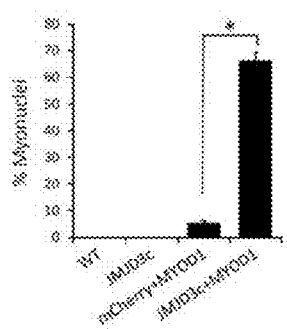
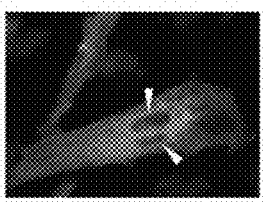
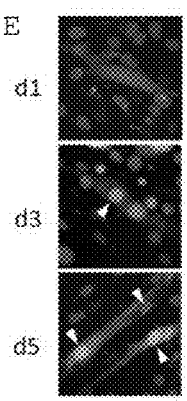
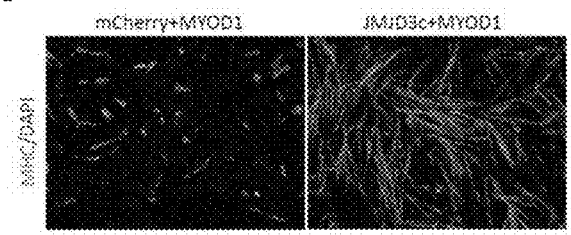
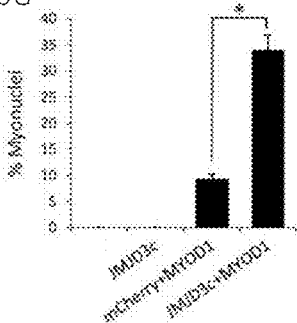
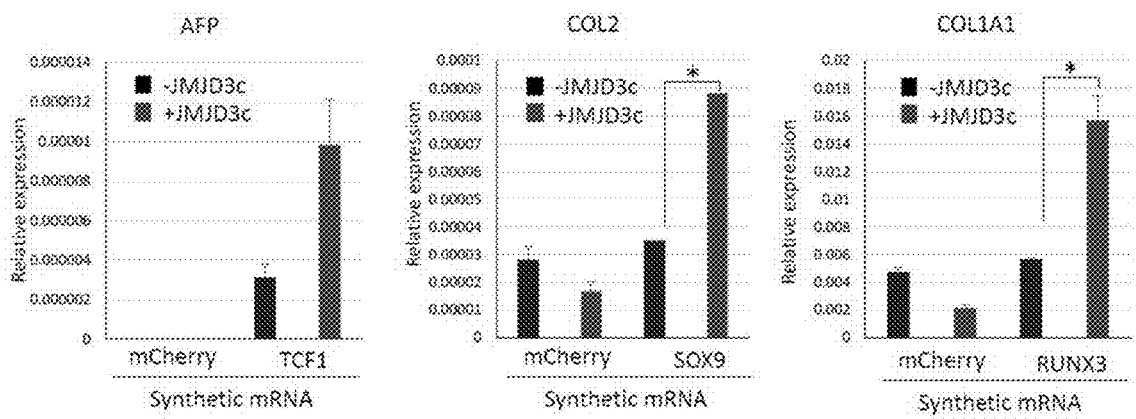

SEQUENCE LISTING

```
<160> NUMBER OF SEQ ID NOS: 94

<210> SEQ ID NO 1
<211> LENGTH: 1682
<212> TYPE: PRT
<213> ORGANISM: Homo sapiens

<400> SEQUENCE: 1

Met His Arg Ala Val Asp Pro Pro Gly Ala Arg Ala Ala Arg Glu Ala
1               5                   10                  15

Phe Ala Leu Gly Gly Leu Ser Cys Ala Gly Ala Trp Ser Ser Cys Pro
            20                  25                  30

Pro His Pro Pro Pro Arg Ser Ala Trp Leu Pro Gly Gly Arg Cys Ser
        35                  40                  45
```

-continued

```
Ala Ser Ile Gly Gln Pro Pro Leu Pro Ala Pro Leu Pro Ser His
    50                  55                  60
Gly Ser Ser Ser Gly His Pro Ser Lys Pro Tyr Tyr Ala Pro Gly Ala
65                  70                  75                  80
Pro Thr Pro Arg Pro Leu His Gly Lys Leu Glu Ser Leu His Gly Cys
                85                  90                  95
Val Gln Ala Leu Leu Arg Glu Pro Ala Gln Pro Gly Leu Trp Glu Gln
            100                 105                 110
Leu Gly Gln Leu Tyr Glu Ser Glu His Asp Ser Glu Ala Thr Arg
            115                 120                 125
Cys Tyr His Ser Ala Leu Arg Tyr Gly Gly Ser Phe Ala Glu Leu Gly
    130                 135                 140
Pro Arg Ile Gly Arg Leu Gln Gln Ala Gln Leu Trp Asn Phe His Thr
145                 150                 155                 160
Gly Ser Cys Gln His Arg Ala Lys Val Leu Pro Leu Glu Gln Val
                165                 170                 175
Trp Asn Leu Leu His Leu Glu His Lys Arg Asn Tyr Gly Ala Lys Arg
            180                 185                 190
Gly Gly Pro Pro Val Lys Arg Ala Ala Glu Pro Val Val Gln Pro
            195                 200                 205
Val Pro Pro Ala Ala Leu Ser Gly Pro Ser Gly Glu Glu Gly Leu Ser
    210                 215                 220
Pro Gly Gly Lys Arg Arg Arg Gly Cys Asn Ser Glu Gln Thr Gly Leu
225                 230                 235                 240
Pro Pro Gly Leu Pro Leu Pro Pro Pro Leu Pro Pro Pro Pro
                245                 250                 255
Pro Pro Pro Pro Pro Pro Pro Leu Pro Gly Leu Ala Thr Ser Pro
                260                 265                 270
Pro Phe Gln Leu Thr Lys Pro Gly Leu Trp Ser Thr Leu His Gly Asp
    275                 280                 285
Ala Trp Gly Pro Glu Arg Lys Gly Ser Ala Pro Pro Glu Arg Gln Glu
    290                 295                 300
Gln Arg His Ser Leu Pro His Pro Tyr Pro Tyr Pro Ala Pro Ala Tyr
305                 310                 315                 320
Thr Ala His Pro Pro Gly His Arg Leu Val Pro Ala Ala Pro Gly
                325                 330                 335
Pro Gly Pro Arg Pro Pro Gly Ala Glu Ser His Gly Cys Leu Pro Ala
            340                 345                 350
Thr Arg Pro Pro Gly Ser Asp Leu Arg Glu Ser Arg Val Gln Arg Ser
            355                 360                 365
Arg Met Asp Ser Ser Val Ser Pro Ala Ala Thr Thr Ala Cys Val Pro
    370                 375                 380
Tyr Ala Pro Ser Arg Pro Pro Gly Leu Pro Gly Thr Thr Thr Ser Ser
385                 390                 395                 400
Ser Ser Ser Ser Ser Asn Thr Gly Leu Arg Gly Val Glu Pro Asn
                405                 410                 415
Pro Gly Ile Pro Gly Ala Asp His Tyr Gln Thr Pro Ala Leu Glu Val
            420                 425                 430
Ser His His Gly Arg Leu Gly Pro Ser Ala His Ser Ser Arg Lys Pro
    435                 440                 445
Phe Leu Gly Ala Pro Ala Ala Thr Pro His Leu Ser Leu Pro Pro Gly
450                 455                 460
```

```
            -continued

Pro Ser Ser Pro Pro Pro Pro Cys Pro Arg Leu Leu Arg Pro Pro
465                 470                 475                 480

Pro Pro Pro Ala Trp Leu Lys Gly Pro Ala Cys Arg Ala Ala Arg Glu
            485                 490                 495

Asp Gly Glu Ile Leu Glu Glu Leu Phe Phe Gly Thr Glu Gly Pro Pro
            500                 505                 510

Arg Pro Ala Pro Pro Leu Pro His Arg Glu Gly Phe Leu Gly Pro
            515                 520                 525

Pro Ala Ser Arg Phe Ser Val Gly Thr Gln Asp Ser His Thr Pro Pro
            530                 535                 540

Thr Pro Pro Thr Pro Thr Thr Ser Ser Asn Ser Asn Ser Gly Ser
545                 550                 555                 560

His Ser Ser Ser Pro Ala Gly Pro Val Ser Phe Pro Pro Pro Tyr
            565                 570                 575

Leu Ala Arg Ser Ile Asp Pro Leu Pro Arg Pro Pro Ser Pro Ala Gln
            580                 585                 590

Asn Pro Gln Asp Pro Pro Leu Val Pro Leu Thr Leu Ala Leu Pro Pro
            595                 600                 605

Ala Pro Pro Ser Ser Cys His Gln Asn Thr Ser Gly Ser Phe Arg Arg
            610                 615                 620

Pro Glu Ser Pro Arg Pro Arg Val Ser Phe Pro Lys Thr Pro Glu Val
625                 630                 635                 640

Gly Pro Gly Pro Pro Gly Pro Leu Ser Lys Ala Pro Gln Pro Val
            645                 650                 655

Pro Pro Gly Val Gly Glu Leu Pro Ala Arg Gly Pro Arg Leu Phe Asp
            660                 665                 670

Phe Pro Pro Thr Pro Leu Glu Asp Gln Phe Glu Glu Pro Ala Glu Phe
            675                 680                 685

Lys Ile Leu Pro Asp Gly Leu Ala Asn Ile Met Lys Met Leu Asp Glu
            690                 695                 700

Ser Ile Arg Lys Glu Glu Glu Gln Gln Gln His Glu Ala Gly Val Ala
705                 710                 715                 720

Pro Gln Pro Pro Leu Lys Glu Pro Phe Ala Ser Leu Gln Ser Pro Phe
            725                 730                 735

Pro Thr Asp Thr Ala Pro Thr Thr Ala Pro Ala Val Ala Val Thr
            740                 745                 750

Thr Thr Thr Thr Thr Thr Thr Thr Thr Ala Thr Gln Glu Glu Glu
            755                 760                 765

Lys Lys Pro Pro Pro Ala Leu Pro Pro Pro Pro Leu Ala Lys Phe
770                 775                 780

Pro Pro Pro Ser Gln Pro Gln Pro Pro Pro Pro Pro Ser Pro
785                 790                 795                 800

Ala Ser Leu Leu Lys Ser Leu Ala Ser Val Leu Glu Gly Gln Lys Tyr
            805                 810                 815

Cys Tyr Arg Gly Thr Gly Ala Ala Val Ser Thr Arg Pro Gly Pro Leu
            820                 825                 830

Pro Thr Thr Gln Tyr Ser Pro Gly Pro Ser Gly Ala Thr Ala Leu
            835                 840                 845

Pro Pro Thr Ser Ala Ala Pro Ser Ala Gln Gly Ser Pro Gln Pro Ser
            850                 855                 860

Ala Ser Ser Ser Ser Gln Phe Ser Thr Ser Gly Gly Pro Trp Ala Arg
865                 870                 875                 880
```

-continued

```
Glu Arg Arg Ala Gly Glu Glu Pro Val Pro Gly Pro Met Thr Pro Thr
                885                 890                 895
Gln Pro Pro Pro Leu Ser Leu Pro Pro Ala Arg Ser Glu Ser Glu
        900                 905                 910
Val Leu Glu Glu Ile Ser Arg Ala Cys Glu Thr Leu Val Glu Arg Val
        915                 920                 925
Gly Arg Ser Ala Thr Asp Pro Ala Asp Pro Val Asp Thr Ala Glu Pro
    930                 935                 940
Ala Asp Ser Gly Thr Glu Arg Leu Leu Pro Pro Ala Gln Ala Lys Glu
945                 950                 955                 960
Glu Ala Gly Gly Val Ala Ala Val Ser Gly Ser Cys Lys Arg Arg Gln
            965                 970                 975
Lys Glu His Gln Lys Glu His Arg Arg His Arg Arg Ala Cys Lys Asp
            980                 985                 990
Ser Val Gly Arg Arg Pro Arg Glu Gly Arg Ala Lys Ala Lys Ala Lys
        995                 1000                1005
Val Pro Lys Glu Lys Ser Arg Arg Val Leu Gly Asn Leu Asp Leu
    1010                1015                1020
Gln Ser Glu Glu Ile Gln Gly Arg Glu Lys Ser Arg Pro Asp Leu
    1025                1030                1035
Gly Gly Ala Ser Lys Ala Lys Pro Pro Thr Ala Pro Ala Pro Pro
    1040                1045                1050
Ser Ala Pro Ala Pro Ser Ala Gln Pro Thr Pro Pro Ser Ala Ser
    1055                1060                1065
Val Pro Gly Lys Lys Ala Arg Glu Glu Ala Pro Gly Pro Pro Gly
    1070                1075                1080
Val Ser Arg Ala Asp Met Leu Lys Leu Arg Ser Leu Ser Glu Gly
    1085                1090                1095
Pro Pro Lys Glu Leu Lys Ile Arg Leu Ile Lys Val Glu Ser Gly
    1100                1105                1110
Asp Lys Glu Thr Phe Ile Ala Ser Glu Val Glu Glu Arg Arg Leu
    1115                1120                1125
Arg Met Ala Asp Leu Thr Ile Ser His Cys Ala Ala Asp Val Val
    1130                1135                1140
Arg Ala Ser Arg Asn Ala Lys Val Lys Gly Lys Phe Arg Glu Ser
    1145                1150                1155
Tyr Leu Ser Pro Ala Gln Ser Val Lys Pro Lys Ile Asn Thr Glu
    1160                1165                1170
Glu Lys Leu Pro Arg Glu Lys Leu Asn Pro Pro Thr Pro Ser Ile
    1175                1180                1185
Tyr Leu Glu Ser Lys Arg Asp Ala Phe Ser Pro Val Leu Leu Gln
    1190                1195                1200
Phe Cys Thr Asp Pro Arg Asn Pro Ile Thr Val Ile Arg Gly Leu
    1205                1210                1215
Ala Gly Ser Leu Arg Leu Asn Leu Gly Leu Phe Ser Thr Lys Thr
    1220                1225                1230
Leu Val Glu Ala Ser Gly Glu His Thr Val Glu Val Arg Thr Gln
    1235                1240                1245
Val Gln Gln Pro Ser Asp Glu Asn Trp Asp Leu Thr Gly Thr Arg
    1250                1255                1260
Gln Ile Trp Pro Cys Glu Ser Ser Arg Ser His Thr Thr Ile Ala
    1265                1270                1275
```

```
Lys Tyr Ala Gln Tyr Gln Ala Ser Ser Phe Gln Glu Ser Leu Gln
    1280                1285                1290

Glu Glu Lys Glu Ser Glu Asp Glu Glu Ser Glu Glu Pro Asp Ser
    1295                1300                1305

Thr Thr Gly Thr Pro Pro Ser Ser Ala Pro Asp Pro Lys Asn His
    1310                1315                1320

His Ile Ile Lys Phe Gly Thr Asn Ile Asp Leu Ser Asp Ala Lys
    1325                1330                1335

Arg Trp Lys Pro Gln Leu Gln Glu Leu Leu Lys Leu Pro Ala Phe
    1340                1345                1350

Met Arg Val Thr Ser Thr Gly Asn Met Leu Ser His Val Gly His
    1355                1360                1365

Thr Ile Leu Gly Met Asn Thr Val Gln Leu Tyr Met Lys Val Pro
    1370                1375                1380

Gly Ser Arg Thr Pro Gly His Gln Glu Asn Asn Asn Phe Cys Ser
    1385                1390                1395

Val Asn Ile Asn Ile Gly Pro Gly Asp Cys Glu Trp Phe Ala Val
    1400                1405                1410

His Glu His Tyr Trp Glu Thr Ile Ser Ala Phe Cys Asp Arg His
    1415                1420                1425

Gly Val Asp Tyr Leu Thr Gly Ser Trp Trp Pro Ile Leu Asp Asp
    1430                1435                1440

Leu Tyr Ala Ser Asn Ile Pro Val Tyr Arg Phe Val Gln Arg Pro
    1445                1450                1455

Gly Asp Leu Val Trp Ile Asn Ala Gly Thr Val His Trp Val Gln
    1460                1465                1470

Ala Thr Gly Trp Cys Asn Asn Ile Ala Trp Asn Val Gly Pro Leu
    1475                1480                1485

Thr Ala Tyr Gln Tyr Gln Leu Ala Leu Glu Arg Tyr Glu Trp Asn
    1490                1495                1500

Glu Val Lys Asn Val Lys Ser Ile Val Pro Met Ile His Val Ser
    1505                1510                1515

Trp Asn Val Ala Arg Thr Val Lys Ile Ser Asp Pro Asp Leu Phe
    1520                1525                1530

Lys Met Ile Lys Phe Cys Leu Leu Gln Ser Met Lys His Cys Gln
    1535                1540                1545

Val Gln Arg Glu Ser Leu Val Arg Ala Gly Lys Lys Ile Ala Tyr
    1550                1555                1560

Gln Gly Arg Val Lys Asp Glu Pro Ala Tyr Tyr Cys Asn Glu Cys
    1565                1570                1575

Asp Val Glu Val Phe Asn Ile Leu Phe Val Thr Ser Glu Asn Gly
    1580                1585                1590

Ser Arg Asn Thr Tyr Leu Val His Cys Glu Gly Cys Ala Arg Arg
    1595                1600                1605

Arg Ser Ala Gly Leu Gln Gly Val Val Val Leu Glu Gln Tyr Arg
    1610                1615                1620

Thr Glu Glu Leu Ala Gln Ala Tyr Asp Ala Phe Thr Leu Val Arg
    1625                1630                1635

Ala Arg Arg Ala Arg Gly Gln Arg Arg Arg Ala Leu Gly Gln Ala
    1640                1645                1650
```

Ala Gly Thr Gly Phe Gly Ser Pro Ala Pro Phe Pro Glu Pro
1655                1660                1665

Pro Pro Ala Phe Ser Pro Gln Ala Pro Ala Ser Thr Ser Arg
1670                1675                1680

<210> SEQ ID NO 2
<211> LENGTH: 659
<212> TYPE: PRT
<213> ORGANISM: Homo sapiens

<400> SEQUENCE: 2

Gln Ser Glu Glu Ile Gln Gly Arg Glu Lys Ser Arg Pro Asp Leu Gly
1               5                   10                  15

Gly Ala Ser Lys Ala Lys Pro Pro Thr Ala Pro Ala Pro Pro Ser Ala
            20                  25                  30

Pro Ala Pro Ser Ala Gln Pro Thr Pro Pro Ser Ala Ser Val Pro Gly
        35                  40                  45

Lys Lys Ala Arg Glu Glu Ala Pro Gly Pro Pro Gly Val Ser Arg Ala
50                  55                  60

Asp Met Leu Lys Leu Arg Ser Leu Ser Glu Gly Pro Pro Lys Glu Leu
65                  70                  75                  80

Lys Ile Arg Leu Ile Lys Val Glu Ser Gly Asp Lys Glu Thr Phe Ile
                85                  90                  95

Ala Ser Glu Val Glu Glu Arg Arg Leu Arg Met Ala Asp Leu Thr Ile
            100                 105                 110

Ser His Cys Ala Ala Asp Val Val Arg Ala Ser Arg Asn Ala Lys Val
        115                 120                 125

Lys Gly Lys Phe Arg Glu Ser Tyr Leu Ser Pro Ala Gln Ser Val Lys
130                 135                 140

Pro Lys Ile Asn Thr Glu Glu Lys Leu Pro Arg Glu Lys Leu Asn Pro
145                 150                 155                 160

Pro Thr Pro Ser Ile Tyr Leu Glu Ser Lys Arg Asp Ala Phe Ser Pro
                165                 170                 175

Val Leu Leu Gln Phe Cys Thr Asp Pro Arg Asn Pro Ile Thr Val Ile
            180                 185                 190

Arg Gly Leu Ala Gly Ser Leu Arg Leu Asn Leu Gly Leu Phe Ser Thr
        195                 200                 205

Lys Thr Leu Val Glu Ala Ser Gly Glu His Thr Val Glu Val Arg Thr
210                 215                 220

Gln Val Gln Gln Pro Ser Asp Glu Asn Trp Asp Leu Thr Gly Thr Arg
225                 230                 235                 240

Gln Ile Trp Pro Cys Glu Ser Ser Arg Ser His Thr Thr Ile Ala Lys
                245                 250                 255

Tyr Ala Gln Tyr Gln Ala Ser Ser Phe Gln Glu Ser Leu Gln Glu Glu
            260                 265                 270

Lys Glu Ser Glu Asp Glu Glu Ser Glu Glu Pro Asp Ser Thr Thr Gly
        275                 280                 285

Thr Pro Pro Ser Ser Ala Pro Asp Pro Lys Asn His His Ile Ile Lys
290                 295                 300

Phe Gly Thr Asn Ile Asp Leu Ser Asp Ala Lys Arg Trp Lys Pro Gln
305                 310                 315                 320

Leu Gln Glu Leu Leu Lys Leu Pro Ala Phe Met Arg Val Thr Ser Thr
                325                 330                 335

Gly Asn Met Leu Ser His Val Gly His Thr Ile Leu Gly Met Asn Thr
            340                 345                 350

-continued

Val Gln Leu Tyr Met Lys Val Pro Gly Ser Arg Thr Pro Gly His Gln
            355                 360                 365

Glu Asn Asn Asn Phe Cys Ser Val Asn Ile Asn Ile Gly Pro Gly Asp
    370                 375                 380

Cys Glu Trp Phe Ala Val His Glu His Tyr Trp Glu Thr Ile Ser Ala
385                 390                 395                 400

Phe Cys Asp Arg His Gly Val Asp Tyr Leu Thr Gly Ser Trp Trp Pro
                405                 410                 415

Ile Leu Asp Asp Leu Tyr Ala Ser Asn Ile Pro Val Tyr Arg Phe Val
                420                 425                 430

Gln Arg Pro Gly Asp Leu Val Trp Ile Asn Ala Gly Thr Val His Trp
            435                 440                 445

Val Gln Ala Thr Gly Trp Cys Asn Asn Ile Ala Trp Asn Val Gly Pro
        450                 455                 460

Leu Thr Ala Tyr Gln Tyr Gln Leu Ala Leu Glu Arg Tyr Glu Trp Asn
465                 470                 475                 480

Glu Val Lys Asn Val Lys Ser Ile Val Pro Met Ile His Val Ser Trp
                485                 490                 495

Asn Val Ala Arg Thr Val Lys Ile Ser Asp Pro Asp Leu Phe Lys Met
            500                 505                 510

Ile Lys Phe Cys Leu Leu Gln Ser Met Lys His Cys Gln Val Gln Arg
        515                 520                 525

Glu Ser Leu Val Arg Ala Gly Lys Lys Ile Ala Tyr Gln Gly Arg Val
        530                 535                 540

Lys Asp Glu Pro Ala Tyr Tyr Cys Asn Glu Cys Asp Val Glu Val Phe
545                 550                 555                 560

Asn Ile Leu Phe Val Thr Ser Glu Asn Gly Ser Arg Asn Thr Tyr Leu
                565                 570                 575

Val His Cys Glu Gly Cys Ala Arg Arg Arg Ser Ala Gly Leu Gln Gly
            580                 585                 590

Val Val Val Leu Glu Gln Tyr Arg Thr Glu Glu Leu Ala Gln Ala Tyr
        595                 600                 605

Asp Ala Phe Thr Leu Val Arg Ala Arg Ala Arg Gly Gln Arg Arg
610                 615                 620

Arg Ala Leu Gly Gln Ala Ala Gly Thr Gly Phe Gly Ser Pro Ala Ala
625                 630                 635                 640

Pro Phe Pro Glu Pro Pro Ala Phe Ser Pro Gln Ala Pro Ala Ser
                645                 650                 655

Thr Ser Arg

<210> SEQ ID NO 3
<211> LENGTH: 109
<212> TYPE: PRT
<213> ORGANISM: Homo sapiens

<400> SEQUENCE: 3

Gln Leu Tyr Met Lys Val Pro Gly Ser Arg Thr Pro Gly His Gln Glu
1               5                   10                  15

Asn Asn Asn Phe Cys Ser Val Asn Ile Asn Ile Gly Pro Gly Asp Cys
                20                  25                  30

Glu Trp Phe Ala Val His Glu His Tyr Trp Glu Thr Ile Ser Ala Phe
            35                  40                  45

Cys Asp Arg His Gly Val Asp Tyr Leu Thr Gly Ser Trp Trp Pro Ile
        50                  55                  60

```
Leu Asp Asp Leu Tyr Ala Ser Asn Ile Pro Val Tyr Arg Phe Val Gln
 65                  70                  75                  80

Arg Pro Gly Asp Leu Val Trp Ile Asn Ala Gly Thr Val His Trp Val
                 85                  90                  95

Gln Ala Thr Gly Trp Cys Asn Asn Ile Ala Trp Asn Val
            100                 105

<210> SEQ ID NO 4
<211> LENGTH: 5049
<212> TYPE: DNA
<213> ORGANISM: Homo sapiens

<400> SEQUENCE: 4
```

| | | | |
|---|---|---|---|
| atgcatcggg cagtggatcc tccaggggcc cgcgctgcac gggaagcctt tgcccttggg | 60 |
| ggcctgagct gtgctggggc ctggagctcc tgcccgcctc atcccctcc tcgtagcgca | 120 |
| tggctgcctg gaggcagatg ctcagccagc attgggcagc cccgcttcc tgctccccta | 180 |
| cccccttcac atggcagtag ttctgggcac cccagcaaac catattatgc tccaggggcg | 240 |
| cccactccaa gacccctcca tgggaagctg gaatccctgc atggctgtgt gcaggcattg | 300 |
| ctccgggagc cagcccagcc agggcttttgg gaacagcttg gcaactgta cgagtcagag | 360 |
| cacgatagtg aggaggccac acgctgctac cacagcgccc ttcgatacgg aggaagcttc | 420 |
| gctgagctgg ggccccgcat ggccgactg cagcaggccc agtctggaa ctttcatact | 480 |
| ggctcctgcc agcaccgagc caaggtcctg cccccactgg agcaagtgtg aacttgcta | 540 |
| caccttgagc acaaacggaa ctatggagcc aagcggggag gtccccggt gaagcgagct | 600 |
| gctgaacccc cagtggtgca gcctgtgcct cctgcagcac tctcaggccc ctcaggggag | 660 |
| gagggcctca gccctggagg caagcgaagg agaggctgca actctgaaca gactggcctt | 720 |
| cccccagggc tgccactgcc tccaccacca ttaccaccac caccaccac accaccacca | 780 |
| ccaccaccac ccctgcctgg cctggctacc agcccccat tcagctaac caagccaggg | 840 |
| ctgtggagta ccctgcatgg agatgcctgg ggcccagagc gcaagggttc agcaccccca | 900 |
| gagcgccagg agcagcggca ctcgctgcct cacccatatc catacccagc tccagcgtac | 960 |
| accgcgcacc ccctggcca ccggctggtc ccggctgctc ccccaggccc aggccccgc | 1020 |
| cccccaggag cagagagcca tggctgcctg cctgccaccc gtcccccgg aagtgacctt | 1080 |
| agagagagca gagttcagag gtcgcggatg gactccagcg tttcaccagc agcaaccacc | 1140 |
| gcctgcgtgc cttacgcccc ttcccggccc cctggcctcc ccggcaccac caccagcagc | 1200 |
| agcagtagca gcagcagcaa cactggtctc cggggcgtgg agccgaaccc aggcattccc | 1260 |
| ggcgctgacc attaccaaac tcccgcgctg gaggtctctc accatggccg cctggggccc | 1320 |
| tcggcacaca gcagtcggaa accgttcttg ggggctcccg ctgccactcc ccacctatcc | 1380 |
| ctgccacctg gacttcctc acccccctcca ccccctgtc ccgcctctt acgcccccca | 1440 |
| ccaccccctg cctggttgaa gggtccggcc tgccgggcag cccgagagga tggagagatc | 1500 |
| ttagaagagc tcttctttgg gactgaggga cccccccgcc ctgccccacc accctcccc | 1560 |
| catcgcgagg gcttctttggg gcctccggcc tccgctttt ctgtgggcac tcaggattct | 1620 |
| cacacccctc ccactccccc aacccaaacc accagcagta gcaacagcaa cagtggcagc | 1680 |
| cacagcagca gccctgctgg gctgtgtcc tttccccac caccctatct ggccagaagt | 1740 |
| atagaccccc ttccccggcc tcccagccca gcacagaacc cccaggaccc acctcttgta | 1800 |
| cccctgactc ttgccctgcc tccagcccct ccttcctcct gccaccaaaa tacctcagga | 1860 |

```
agcttcaggc gcccggagag ccccccggccc agggtctcct tcccaaagac ccccgaggtg    1920
gggccggggc cacccccagg cccctgagt aaagccccc agcctgtgcc gcccgggtt       1980
ggggagctgc ctgcccgagg ccctcgactc tttgattttc ccccactcc gctggaggac    2040
cagtttgagg agccagccga attcaagatc tacctgatg ggctggccaa catcatgaag    2100
atgctggacg aatccattcg caaggaagag gaacagcaac aacacgaagc aggcgtggcc   2160
ccccaacccc cgctgaagga gccctttgca tctctgcagt ctcctttccc caccgacaca   2220
gcccccacca ctactgctcc tgctgtcgcc gtcaccacca ccaccaccac caccaccacc   2280
accacggcca cccaggaaga ggagaagaag ccaccaccag ccctaccacc accaccgcct   2340
ctagccaagt tccctccacc ctctcagcca cagccaccac cacccccacc cccagcccg    2400
gccagcctgc tcaaatcctt ggcctccgtg ctggagggac aaaagtactg ttatcggggg   2460
actggagcag ctgttccac ccggcctggg cccttgccca ccactcagta ttccctggc    2520
cccccatcag gtgctaccgc cctgccgccc acctcagcgg ccctagcgc cagggctcc    2580
ccacagccct ctgcttcctc gtcatctcag ttctctacct caggcgggcc ctgggccgg    2640
gagcgcaggg cgggcgaaga gccagtcccg ggccccatga ccccaccca accgccccca    2700
cccctatctc tgcccctgc tcgctctgag tctgaggtgc tagaagagat cagccgggct    2760
tgcgagaccc ttgtggagcg ggtgggccgg agtgccactg acccagccga cccagtggac   2820
acagcagagc agcggacag tgggactgag cgactgctgc ccccgcaca ggccaaggag    2880
gaggctggcg gggtggcggc agtgtcaggc agctgtaagc ggcgacagaa ggagcatcag   2940
aaggagcatc ggcggcacag gcgggcctgt aaggacagtg tgggtcgtcg gccccgtgag   3000
ggcagggcaa aggccaaggc caaggtcccc aaagaaaaga gccgccgggt gctggggaac   3060
ctggacctgc agagcgagga gatccagggt cgtgagaagt cccggcccga tcttggcggg   3120
gcctccaagg ccaagccacc cacagctcca gcccctccat cagctcctgc accttctgcc   3180
cagcccacac ccccgtcagc ctctgtccct ggaaagaagg ctcgggagga agccccaggg   3240
ccaccgggtg tcagccgggc cgacatgctg aagctgcgct cacttagtga ggggcccccc   3300
aaggagctga gatccggct catcaaggta gagagtggtg acaaggagac ctttatcgcc   3360
tctgaggtgg aagagcggcg gctgcgcatg gcagacctca ccatcagcca ctgtgctgct   3420
gacgtcgtgc gcgccagcag gaatgccaag gtgaaaggga gtttcgaga gtcctacctt   3480
tcccctgccc agtctgtgaa accgaagatc aacactgagg agaagctgcc ccgggaaaaa   3540
ctcaaccccc ctacacccag catctatctg gagagcaaac gggatgcctt ctcacctgtc   3600
ctgctgcagt tctgtacaga ccctcgaaat cccatcacag tgatccgggg cctggcgggc   3660
tccctgcggg tcaacttggg cctcttctcc accaagaccc tggtggaagc gagtggcgaa   3720
cacaccgtgg aagttcgcac ccaggtgcag cagccctcag atgagaactg ggatctgaca   3780
ggcactcggc agatctggcc ttgtgagagc tcccgttccc acaccaccat tgccaagtac   3840
gcacagtacc aggcctcatc cttccaggag tctctgcagg aggagaagga gagtgaggat   3900
gaggagtcag aggagccaga cagcaccact ggaaccctc ctagcagcgc accagacccg    3960
aagaaccatc acatcatcaa gtttggcacc aacatcgact tgtctgatgc taagcggtgg   4020
aagccccagc tgcaggagct gctgaagctg cccgccttca tgcgggtaac atccacgggc   4080
aacatgctga gccacgtggg ccacaccatc ctgggcatga acacggtgca gctgtacatg   4140
aaggtgcccg gcagccgaac gccaggccac caggagaata caacttctg ctccgtcaac    4200
atcaacattg gcccaggcga ctgcgagtgg ttcgcggtgc acgagcacta ctgggagacc   4260
```

```
atcagcgctt tctgtgatcg gcacggcgtg gactacttga cgggttcctg gtggccaatc    4320
ctggatgatc tctatgcatc caatattcct gtgtaccgct tcgtgcagcg acccggagac    4380
ctcgtgtgga ttaatgcggg gactgtgcac tgggtgcagg ccaccggctg gtgcaacaac    4440
attgcctgga acgtggggcc cctcaccgcc tatcagtacc agctggccct ggaacgatac    4500
gagtggaatg aggtgaagaa cgtcaaatcc atcgtgccca tgattcacgt gtcatggaac    4560
gtggctcgca cggtcaaaat cagcgacccc gacttgttca agatgatcaa gttctgcctg    4620
ctgcagtcca tgaagcactg ccaggtgcaa cgcgagagcc tggtgcgggc agggaagaaa    4680
atcgcttacc agggccgtgt caaggacgag ccagcctact actgcaacga gtgcgatgtg    4740
gaggtgttta acatcctgtt cgtgacaagt gagaatggca gccgcaacac gtacctggta    4800
cactgcgagg gctgtgcccg cgccgcagc gcaggcctgc agggcgtggt ggtgctggag    4860
cagtaccgca ctgaggagct ggctcaggcc tacgacgcct tcacgctggt gagggcccgg    4920
cgggcgcgcg gcagcggag gagggcactg gggcaggctg cagggacggg cttcgggagc    4980
ccggccgcgc ctttccctga gccccgccg gctttctccc ccaggcccc agccagcacg    5040 tcgcgatga                                                           5049

<210> SEQ ID NO 5
<211> LENGTH: 1980
<212> TYPE: DNA
<213> ORGANISM: Homo sapiens

<400> SEQUENCE: 5
cagagcgagg agatccaggg tcgtgagaag tcccggcccg atcttggcgg ggcctccaag      60
gccaagccac ccacagctcc agcccctcca tcagctcctg caccttctgc ccagcccaca     120
cccccgtcag cctctgtccc tggaaagaag gctcggagg aagccccagg ccaccgggt      180 gtcagccggg ccgacatgct gaagctgcgc tcacttagtg aggggccccc caaggagctg     240
aagatccggc tcatcaaggt agagagtggt gacaaggaga cctttatcgc ctctgaggtg     300
gaagagcggc ggctgcgcat ggcagacctc accatcagcc actgtgctgc tgacgtcgtg     360
cgcgccagca ggaatgccaa ggtgaaaggg aagtttcgag agtcctacct ttcccctgcc     420
cagtctgtga aaccgaagat caacactgag gagaagctgc cccgggaaaa actcaaccc     480 cctacacccca gcatctatct ggagagcaaa cgggatgcct tctcacctgt cctgctgcag     540
ttctgtacag accctcgaaa tcccatcaca gtgatccggg gcctggcggg ctccctgcgg     600
ctcaacttgg gcctcttctc caccaagacc ctggtggaag cgagtggcga acacaccgtg     660
gaagttcgca cccaggtgca gcagccctca gatgagaact gggatctgac aggcactcgg     720
cagatctggc cttgtgagag ctcccgttcc cacaccacca ttgccaagta cgcacagtac     780
caggcctcat ccttccagga gtctctgcag gaggagaagg agagtgagga tgaggagtca     840
gaggagccag acagcaccac tggaacccct cctagcagcg caccagaccc gaagaaccat     900
cacatcatca gttttggcac caacatcgac ttgtctgatg ctaagcggtg gaagcccag     960 ctgcaggagc tgctgaagct gcccgccttc atgcgggtaa catccacggg caacatgctg    1020
agccacgtgg ccacaccat cctgggcatg aacacggtgc agctgtacat gaaggtgccc    1080
ggcagccgaa cgccaggcca ccaggagaat aacaacttct gctccgtcaa catcaacatt    1140
ggcccaggcg actgcgagtg gttcgcggtg cacgagcact actgggagac catcagcgct    1200
ttctgtgatc ggcacggcgt ggactacttg acgggttcct ggtggccaat cctggatgat    1260
ctctatgcat ccaatattcc tgtgtaccgc ttcgtgcagc gacccggaga cctcgtgtgg    1320
```

```
attaatgcgg ggactgtgca ctgggtgcag gccaccggct ggtgcaacaa cattgcctgg      1380
aacgtggggc ccctcaccgc ctatcagtac cagctggccc tggaacgata cgagtggaat      1440
gaggtgaaga acgtcaaatc catcgtgccc atgattcacg tgtcatggaa cgtggctcgc      1500
acggtcaaaa tcagcgaccc cgacttgttc aagatgatca agttctgcct gctgcagtcc      1560
atgaagcact gccaggtgca acgcgagagc ctggtgcggg cagggaagaa aatcgcttac      1620
cagggccgtg tcaaggacga gccagcctac tactgcaacg agtgcgatgt ggaggtgttt      1680
aacatcctgt tcgtgacaag tgagaatggc agccgcaaca cgtacctggt acactgcgag      1740
ggctgtgccc ggcgccgcag cgcaggcctg cagggcgtgg tggtgctgga gcagtaccgc      1800
actgaggagc tggctcaggc ctacgacgcc ttcacgctgg tgagggcccg gcgggcgcgc      1860
gggcagcgga ggagggcact ggggcaggct gcagggacgg gcttcgggag cccggccgcg      1920
cctttccctg agccccgcc ggctttctcc ccccaggccc cagccagcac gtcgcgatga      1980

<210> SEQ ID NO 6
<211> LENGTH: 327
<212> TYPE: DNA
<213> ORGANISM: Homo sapiens

<400> SEQUENCE: 6
cagctgtaca tgaaggtgcc cggcagccga acgccaggcc accaggagaa taacaacttc        60
tgctccgtca acatcaacat tggcccaggc gactgcgagt ggttcgcggt gcacgagcac       120
tactgggaga ccatcagcgc tttctgtgat cggcacggcg tggactactt gacgggttcc       180
tggtggccaa tcctggatga tctctatgca tccaatattc ctgtgtaccg cttcgtgcag       240
cgacccggag acctcgtgtg gattaatgcg gggactgtgc actgggtgca ggccaccggc       300
tggtgcaaca cattgcctg gaacgtg                                             327

<210> SEQ ID NO 7
<211> LENGTH: 12
<212> TYPE: PRT
<213> ORGANISM: Human immunodeficiency virus

<400> SEQUENCE: 7

Gly Arg Lys Lys Arg Arg Gln Arg Arg Arg Pro Gln
1               5                   10

<210> SEQ ID NO 8
<211> LENGTH: 8
<212> TYPE: PRT
<213> ORGANISM: Artificial Sequence
<220> FEATURE:
<223> OTHER INFORMATION: r8

<400> SEQUENCE: 8

Arg Arg Arg Arg Arg Arg Arg Arg
1               5

<210> SEQ ID NO 9
<211> LENGTH: 21
<212> TYPE: PRT
<213> ORGANISM: Artificial Sequence
<220> FEATURE:
<223> OTHER INFORMATION: MPG-8 (The first amino acid "Ala" is modified
      into "bAla.")
```

<400> SEQUENCE: 9

Ala Phe Leu Gly Trp Leu Gly Ala Trp Gly Thr Met Gly Trp Ser Pro
1               5                   10                  15

Lys Lys Lys Arg Lys
            20

<210> SEQ ID NO 10
<211> LENGTH: 23
<212> TYPE: DNA
<213> ORGANISM: Artificial Sequence
<220> FEATURE:
<223> OTHER INFORMATION: qRT-PCR forward primer for GAPDH

<400> SEQUENCE: 10
ggtggtctcc tctgacttca aca                                    23

<210> SEQ ID NO 11
<211> LENGTH: 19
<212> TYPE: DNA
<213> ORGANISM: Artificial Sequence
<220> FEATURE:
<223> OTHER INFORMATION: qRT-PCR reverse primer for GAPDH

<400> SEQUENCE: 11
gtggtcgttg agggcaatg                                         19

<210> SEQ ID NO 12
<211> LENGTH: 22
<212> TYPE: DNA
<213> ORGANISM: Artificial Sequence
<220> FEATURE:
<223> OTHER INFORMATION: qRT-PCR forward primer for POU5F1

<400> SEQUENCE: 12
cttgaatccc gaatggaaag gg                                     22

<210> SEQ ID NO 13
<211> LENGTH: 23
<212> TYPE: DNA
<213> ORGANISM: Artificial Sequence
<220> FEATURE:
<223> OTHER INFORMATION: qRT-PCR reverse primer for POU5F1

<400> SEQUENCE: 13
gtgtatatcc cagggtgatc ctc                                    23

<210> SEQ ID NO 14
<211> LENGTH: 19
<212> TYPE: DNA
<213> ORGANISM: Artificial Sequence
<220> FEATURE:
<223> OTHER INFORMATION: qRT-PCR forward primer for NANOG

<400> SEQUENCE: 14
agaaggcctc agcacctac                                         19

<210> SEQ ID NO 15
<211> LENGTH: 20
<212> TYPE: DNA
<213> ORGANISM: Artificial Sequence
<220> FEATURE:
<223> OTHER INFORMATION: qRT-PCR reverse primer for NANOG

<400> SEQUENCE: 15
ggcctgattg ttccaggatt                                        20

```
<210> SEQ ID NO 16
<211> LENGTH: 26
<212> TYPE: DNA
<213> ORGANISM: Artificial Sequence
<220> FEATURE:
<223> OTHER INFORMATION: qRT-PCR forward primer for T

<400> SEQUENCE: 16
gccctctccc tccctccac gcacag                                        26

<210> SEQ ID NO 17
<211> LENGTH: 26
<212> TYPE: DNA
<213> ORGANISM: Artificial Sequence
<220> FEATURE:
<223> OTHER INFORMATION: qRT-PCR reverse primer for T

<400> SEQUENCE: 17
cggcgccgtt gctcacagac cacagg                                       26

<210> SEQ ID NO 18
<211> LENGTH: 24
<212> TYPE: DNA
<213> ORGANISM: Artificial Sequence
<220> FEATURE:
<223> OTHER INFORMATION: qRT-PCR forward primer for MSX1

<400> SEQUENCE: 18
cgagaggacc ccgtggatgc agag                                         24

<210> SEQ ID NO 19
<211> LENGTH: 24
<212> TYPE: DNA
<213> ORGANISM: Artificial Sequence
<220> FEATURE:
<223> OTHER INFORMATION: qRT-PCR reverse primer for MSX1

<400> SEQUENCE: 19
ggcggccatc ttcagcttct ccag                                         24

<210> SEQ ID NO 20
<211> LENGTH: 26
<212> TYPE: DNA
<213> ORGANISM: Artificial Sequence
<220> FEATURE:
<223> OTHER INFORMATION: qRT-PCR forward primer for SOX17

<400> SEQUENCE: 20
cgctttcatg gtgtgggcta aggacg                                       26

<210> SEQ ID NO 21
<211> LENGTH: 26
<212> TYPE: DNA
<213> ORGANISM: Artificial Sequence
<220> FEATURE:
<223> OTHER INFORMATION: qRT-PCR reverse primer for SOX17

<400> SEQUENCE: 21
tagttggggt ggtcctgcat gtgctg                                       26

<210> SEQ ID NO 22
<211> LENGTH: 26
<212> TYPE: DNA
<213> ORGANISM: Artificial Sequence
<220> FEATURE:
<223> OTHER INFORMATION: qRT-PCR forward primer for FOXA2
```

```
<400> SEQUENCE: 22
tgggagcggt gaagatggaa gggcac                                              26

<210> SEQ ID NO 23
<211> LENGTH: 26
<212> TYPE: DNA
<213> ORGANISM: Artificial Sequence
<220> FEATURE:
<223> OTHER INFORMATION: qRT-PCR reverse primer for FOXA2

<400> SEQUENCE: 23
tcatgccagc gcccacgtac gacgac                                              26

<210> SEQ ID NO 24
<211> LENGTH: 20
<212> TYPE: DNA
<213> ORGANISM: Artificial Sequence
<220> FEATURE:
<223> OTHER INFORMATION: qRT-PCR forward primer for GATA4

<400> SEQUENCE: 24
gctccttcag gcagtgagag                                                     20

<210> SEQ ID NO 25
<211> LENGTH: 20
<212> TYPE: DNA
<213> ORGANISM: Artificial Sequence
<220> FEATURE:
<223> OTHER INFORMATION: qRT-PCR reverse primer for GATA4

<400> SEQUENCE: 25
ctgtgcccgt agtgagatga                                                     20

<210> SEQ ID NO 26
<211> LENGTH: 20
<212> TYPE: DNA
<213> ORGANISM: Artificial Sequence
<220> FEATURE:
<223> OTHER INFORMATION: qRT-PCR forward primer for GATA6

<400> SEQUENCE: 26
gtgcccagac cacttgctat                                                     20

<210> SEQ ID NO 27
<211> LENGTH: 20
<212> TYPE: DNA
<213> ORGANISM: Artificial Sequence
<220> FEATURE:
<223> OTHER INFORMATION: qRT-PCR reverse primer for GATA6

<400> SEQUENCE: 27
tggagtcatg ggaatggaat                                                     20

<210> SEQ ID NO 28
<211> LENGTH: 20
<212> TYPE: DNA
<213> ORGANISM: Artificial Sequence
<220> FEATURE:
<223> OTHER INFORMATION: qRT-PCR forward primer for GSC

<400> SEQUENCE: 28
cggtcctcat cagaggagtc                                                     20
```

```
<210> SEQ ID NO 29
<211> LENGTH: 20
<212> TYPE: DNA
<213> ORGANISM: Artificial Sequence
<220> FEATURE:
<223> OTHER INFORMATION: qRT-PCR reverse primer for GSC

<400> SEQUENCE: 29
ccgagtccaa atcgctttta                                              20

<210> SEQ ID NO 30
<211> LENGTH: 20
<212> TYPE: DNA
<213> ORGANISM: Artificial Sequence
<220> FEATURE:
<223> OTHER INFORMATION: qRT-PCR forward primer for EVX1

<400> SEQUENCE: 30
cggctggaga aggaattcta                                              20

<210> SEQ ID NO 31
<211> LENGTH: 20
<212> TYPE: DNA
<213> ORGANISM: Artificial Sequence
<220> FEATURE:
<223> OTHER INFORMATION: qRT-PCR reverse primer for EVX1

<400> SEQUENCE: 31
acaccttgat ggtggtttcc                                              20

<210> SEQ ID NO 32
<211> LENGTH: 20
<212> TYPE: DNA
<213> ORGANISM: Artificial Sequence
<220> FEATURE:
<223> OTHER INFORMATION: qRT-PCR forward primer for MYOG

<400> SEQUENCE: 32
gccagactat cccctteectc                                             20

<210> SEQ ID NO 33
<211> LENGTH: 20
<212> TYPE: DNA
<213> ORGANISM: Artificial Sequence
<220> FEATURE:
<223> OTHER INFORMATION: qRT-PCR reverse primer for MYOG

<400> SEQUENCE: 33
gaggccgcgt tatgataaaa                                              20

<210> SEQ ID NO 34
<211> LENGTH: 20
<212> TYPE: DNA
<213> ORGANISM: Artificial Sequence
<220> FEATURE:
<223> OTHER INFORMATION: qRT-PCR forward primer for MEF2C

<400> SEQUENCE: 34
aggtcacctg acatcccaag                                              20

<210> SEQ ID NO 35
<211> LENGTH: 20
<212> TYPE: DNA
<213> ORGANISM: Artificial Sequence
<220> FEATURE:
<223> OTHER INFORMATION: qRT-PCR reverse primer for MEF2C
```

```
<400> SEQUENCE: 35
gttagccctc caactccaca                                          20

<210> SEQ ID NO 36
<211> LENGTH: 20
<212> TYPE: DNA
<213> ORGANISM: Artificial Sequence
<220> FEATURE:
<223> OTHER INFORMATION: qRT-PCR forward primer for CKM

<400> SEQUENCE: 36
gaagagcatg acggagaagg                                          20

<210> SEQ ID NO 37
<211> LENGTH: 20
<212> TYPE: DNA
<213> ORGANISM: Artificial Sequence
<220> FEATURE:
<223> OTHER INFORMATION: qRT-PCR reverse primer for CKM

<400> SEQUENCE: 37
gttgtcattg tgccagatgc                                          20

<210> SEQ ID NO 38
<211> LENGTH: 20
<212> TYPE: DNA
<213> ORGANISM: Artificial Sequence
<220> FEATURE:
<223> OTHER INFORMATION: qRT-PCR forward primer for SIX1

<400> SEQUENCE: 38
tgtttgcgca taaaggaatg                                          20

<210> SEQ ID NO 39
<211> LENGTH: 20
<212> TYPE: DNA
<213> ORGANISM: Artificial Sequence
<220> FEATURE:
<223> OTHER INFORMATION: qRT-PCR reverse primer for SIX1

<400> SEQUENCE: 39
tgggaaggaa aatgcaaaag                                          20

<210> SEQ ID NO 40
<211> LENGTH: 18
<212> TYPE: DNA
<213> ORGANISM: Artificial Sequence
<220> FEATURE:
<223> OTHER INFORMATION: qRT-PCR forward primer for AFP

<400> SEQUENCE: 40
tgggacccga actttcca                                            18

<210> SEQ ID NO 41
<211> LENGTH: 22
<212> TYPE: DNA
<213> ORGANISM: Artificial Sequence
<220> FEATURE:
<223> OTHER INFORMATION: qRT-PCR reverse primer for AFP

<400> SEQUENCE: 41
ggccacatcc aggactagtt tc                                       22
```

```
<210> SEQ ID NO 42
<211> LENGTH: 20
<212> TYPE: DNA
<213> ORGANISM: Artificial Sequence
<220> FEATURE:
<223> OTHER INFORMATION: qRT-PCR forward primer for COL2

<400> SEQUENCE: 42
tttcccaggt caagatggtc                                                 20

<210> SEQ ID NO 43
<211> LENGTH: 20
<212> TYPE: DNA
<213> ORGANISM: Artificial Sequence
<220> FEATURE:
<223> OTHER INFORMATION: qRT-PCR reverse primer for COL2

<400> SEQUENCE: 43
cttcagcacc tgtctcacca                                                 20

<210> SEQ ID NO 44
<211> LENGTH: 20
<212> TYPE: DNA
<213> ORGANISM: Artificial Sequence
<220> FEATURE:
<223> OTHER INFORMATION: qRT-PCR forward primer for COL1A1

<400> SEQUENCE: 44
cctggatgcc atcaaagtct                                                 20

<210> SEQ ID NO 45
<211> LENGTH: 20
<212> TYPE: DNA
<213> ORGANISM: Artificial Sequence
<220> FEATURE:
<223> OTHER INFORMATION: qRT-PCR reverse primer for COL1A1

<400> SEQUENCE: 45
tcttgtcctt ggggttcttg                                                 20

<210> SEQ ID NO 46
<211> LENGTH: 20
<212> TYPE: DNA
<213> ORGANISM: Artificial Sequence
<220> FEATURE:
<223> OTHER INFORMATION: ChIP-PCR forward primer for POU5F1

<400> SEQUENCE: 46
ggaggtaaac ccagctcaca                                                 20

<210> SEQ ID NO 47
<211> LENGTH: 20
<212> TYPE: DNA
<213> ORGANISM: Artificial Sequence
<220> FEATURE:
<223> OTHER INFORMATION: ChIP-PCR reverse primer for POU5F1

<400> SEQUENCE: 47
tttggcctta gggttaagca                                                 20

<210> SEQ ID NO 48
<211> LENGTH: 20
<212> TYPE: DNA
<213> ORGANISM: Artificial Sequence
<220> FEATURE:
<223> OTHER INFORMATION: ChIP-PCR forward primer for NANOG
```

```
<400> SEQUENCE: 48
gctcagggat gagcatgatt                                          20

<210> SEQ ID NO 49
<211> LENGTH: 20
<212> TYPE: DNA
<213> ORGANISM: Artificial Sequence
<220> FEATURE:
<223> OTHER INFORMATION: ChIP-PCR reverse primer for NANOG

<400> SEQUENCE: 49
tgcccagtaa catccacaaa                                          20

<210> SEQ ID NO 50
<211> LENGTH: 20
<212> TYPE: DNA
<213> ORGANISM: Artificial Sequence
<220> FEATURE:
<223> OTHER INFORMATION: ChIP-PCR forward primer for T

<400> SEQUENCE: 50
ggcacggcca aataagaata                                          20

<210> SEQ ID NO 51
<211> LENGTH: 20
<212> TYPE: DNA
<213> ORGANISM: Artificial Sequence
<220> FEATURE:
<223> OTHER INFORMATION: ChIP-PCR reverse primer for T

<400> SEQUENCE: 51
ggttcaattc ctgggtcgta                                          20

<210> SEQ ID NO 52
<211> LENGTH: 20
<212> TYPE: DNA
<213> ORGANISM: Artificial Sequence
<220> FEATURE:
<223> OTHER INFORMATION: ChIP-PCR forward primer for MSX1

<400> SEQUENCE: 52
tccctcatct gatcccaaac                                          20

<210> SEQ ID NO 53
<211> LENGTH: 20
<212> TYPE: DNA
<213> ORGANISM: Artificial Sequence
<220> FEATURE:
<223> OTHER INFORMATION: ChIP-PCR reverse primer for MSX1

<400> SEQUENCE: 53
accagctcct actgcgagaa                                          20

<210> SEQ ID NO 54
<211> LENGTH: 20
<212> TYPE: DNA
<213> ORGANISM: Artificial Sequence
<220> FEATURE:
<223> OTHER INFORMATION: ChIP-PCR forward primer for SOX17

<400> SEQUENCE: 54
agcaagatgc tgggtgagtc                                          20
```

```
<210> SEQ ID NO 55
<211> LENGTH: 20
<212> TYPE: DNA
<213> ORGANISM: Artificial Sequence
<220> FEATURE:
<223> OTHER INFORMATION: ChIP-PCR reverse primer for SOX17

<400> SEQUENCE: 55
ctacacaccc ctggttttgg                                                  20

<210> SEQ ID NO 56
<211> LENGTH: 20
<212> TYPE: DNA
<213> ORGANISM: Artificial Sequence
<220> FEATURE:
<223> OTHER INFORMATION: ChIP-PCR forward primer for FOXA2

<400> SEQUENCE: 56
ttcttcgctc tcagtgctca                                                  20

<210> SEQ ID NO 57
<211> LENGTH: 21
<212> TYPE: DNA
<213> ORGANISM: Artificial Sequence
<220> FEATURE:
<223> OTHER INFORMATION: ChIP-PCR reverse primer for FOXA2

<400> SEQUENCE: 57
ggcgagttaa aggtgtgtac g                                                21

<210> SEQ ID NO 58
<211> LENGTH: 20
<212> TYPE: DNA
<213> ORGANISM: Artificial Sequence
<220> FEATURE:
<223> OTHER INFORMATION: ChIP-PCR forward primer for GATA4

<400> SEQUENCE: 58
gatcttcgcg acagttcctc                                                  20

<210> SEQ ID NO 59
<211> LENGTH: 20
<212> TYPE: DNA
<213> ORGANISM: Artificial Sequence
<220> FEATURE:
<223> OTHER INFORMATION: ChIP-PCR reverse primer for GATA4

<400> SEQUENCE: 59
catggccaag ctctgataca                                                  20

<210> SEQ ID NO 60
<211> LENGTH: 20
<212> TYPE: DNA
<213> ORGANISM: Artificial Sequence
<220> FEATURE:
<223> OTHER INFORMATION: ChIP-PCR forward primer for GATA6

<400> SEQUENCE: 60
tgcagcctac gctcttgtta                                                  20

<210> SEQ ID NO 61
<211> LENGTH: 19
<212> TYPE: DNA
<213> ORGANISM: Artificial Sequence
<220> FEATURE:
<223> OTHER INFORMATION: ChIP-PCR reverse primer for GATA6
```

```
<400> SEQUENCE: 61
gtcagtcaag gccatccac                                                    19

<210> SEQ ID NO 62
<211> LENGTH: 20
<212> TYPE: DNA
<213> ORGANISM: Artificial Sequence
<220> FEATURE:
<223> OTHER INFORMATION: ChIP-PCR forward primer for GSC

<400> SEQUENCE: 62
gacatgacgg agatgggtct                                                   20

<210> SEQ ID NO 63
<211> LENGTH: 20
<212> TYPE: DNA
<213> ORGANISM: Artificial Sequence
<220> FEATURE:
<223> OTHER INFORMATION: ChIP-PCR reverse primer for GSC

<400> SEQUENCE: 63
tggaaggtgc ctcacttctt                                                   20

<210> SEQ ID NO 64
<211> LENGTH: 20
<212> TYPE: DNA
<213> ORGANISM: Artificial Sequence
<220> FEATURE:
<223> OTHER INFORMATION: ChIP-PCR forward primer for EVX1

<400> SEQUENCE: 64
tcacactctc ctccccaatc                                                   20

<210> SEQ ID NO 65
<211> LENGTH: 20
<212> TYPE: DNA
<213> ORGANISM: Artificial Sequence
<220> FEATURE:
<223> OTHER INFORMATION: ChIP-PCR reverse primer for EVX1

<400> SEQUENCE: 65
ttacagtacc gctggtgacg                                                   20

<210> SEQ ID NO 66
<211> LENGTH: 23
<212> TYPE: DNA
<213> ORGANISM: Artificial Sequence
<220> FEATURE:
<223> OTHER INFORMATION: ChIP-PCR forward primer for GAPDH

<400> SEQUENCE: 66
cggtgactaa ccctgcgctc ctg                                               23

<210> SEQ ID NO 67
<211> LENGTH: 24
<212> TYPE: DNA
<213> ORGANISM: Artificial Sequence
<220> FEATURE:
<223> OTHER INFORMATION: ChIP-PCR reverse primer for GAPDH

<400> SEQUENCE: 67
agctagcctc gctccacctg actt                                              24
```

<210> SEQ ID NO 68
<211> LENGTH: 20
<212> TYPE: DNA
<213> ORGANISM: Artificial Sequence
<220> FEATURE:
<223> OTHER INFORMATION: ChIP-PCR forward primer for MYOG_a

<400> SEQUENCE: 68
cctccggaaa gaatgggact                                              20

<210> SEQ ID NO 69
<211> LENGTH: 21
<212> TYPE: DNA
<213> ORGANISM: Artificial Sequence
<220> FEATURE:
<223> OTHER INFORMATION: ChIP-PCR reverse primer for MYOG_a

<400> SEQUENCE: 69
tctgttagct gctctgagtc t                                            21

<210> SEQ ID NO 70
<211> LENGTH: 20
<212> TYPE: DNA
<213> ORGANISM: Artificial Sequence
<220> FEATURE:
<223> OTHER INFORMATION: ChIP-PCR forward primer for MYOG_b

<400> SEQUENCE: 70
ttggagccaa ggttaccagt                                              20

<210> SEQ ID NO 71
<211> LENGTH: 18
<212> TYPE: DNA
<213> ORGANISM: Artificial Sequence
<220> FEATURE:
<223> OTHER INFORMATION: ChIP-PCR reverse primer for MYOGb

<400> SEQUENCE: 71
ctctcacagc gcctcctg                                                18

<210> SEQ ID NO 72
<211> LENGTH: 20
<212> TYPE: DNA
<213> ORGANISM: Artificial Sequence
<220> FEATURE:
<223> OTHER INFORMATION: ChIP-PCR forward primer for MYOG_c

<400> SEQUENCE: 72
ggcctcattc accttcttga                                              20

<210> SEQ ID NO 73
<211> LENGTH: 20
<212> TYPE: DNA
<213> ORGANISM: Artificial Sequence
<220> FEATURE:
<223> OTHER INFORMATION: ChIP-PCR reverse primer for MYOG_c

<400> SEQUENCE: 73
tgggcgtgta aggtgtgtaa                                              20

<210> SEQ ID NO 74
<211> LENGTH: 20
<212> TYPE: DNA
<213> ORGANISM: Artificial Sequence
<220> FEATURE:
<223> OTHER INFORMATION: ChIP-PCR forward primer for MEF2C_a

```
<400> SEQUENCE: 74
catgcatttt caggtcacca                                             20

<210> SEQ ID NO 75
<211> LENGTH: 20
<212> TYPE: DNA
<213> ORGANISM: Artificial Sequence
<220> FEATURE:
<223> OTHER INFORMATION: ChIP-PCR reverse primer for MEF2C_a

<400> SEQUENCE: 75
cccctccact ttgattcgta                                             20

<210> SEQ ID NO 76
<211> LENGTH: 20
<212> TYPE: DNA
<213> ORGANISM: Artificial Sequence
<220> FEATURE:
<223> OTHER INFORMATION: ChIP-PCR forward primer for MEF2C_b

<400> SEQUENCE: 76
gcacgtttaa gaccccaaag                                             20

<210> SEQ ID NO 77
<211> LENGTH: 20
<212> TYPE: DNA
<213> ORGANISM: Artificial Sequence
<220> FEATURE:
<223> OTHER INFORMATION: ChIP-PCR reverse primer for MEF2C_b

<400> SEQUENCE: 77
cggcctcagc taaatgaaag                                             20

<210> SEQ ID NO 78
<211> LENGTH: 20
<212> TYPE: DNA
<213> ORGANISM: Artificial Sequence
<220> FEATURE:
<223> OTHER INFORMATION: ChIP-PCR forward primer for SOX1

<400> SEQUENCE: 78
ccgtctcact ccgtctgaat                                             20

<210> SEQ ID NO 79
<211> LENGTH: 19
<212> TYPE: DNA
<213> ORGANISM: Artificial Sequence
<220> FEATURE:
<223> OTHER INFORMATION: ChIP-PCR reverse primer for SOX1

<400> SEQUENCE: 79
agtgcaggtc ggtctccat                                              19

<210> SEQ ID NO 80
<211> LENGTH: 2541
<212> TYPE: DNA
<213> ORGANISM: Homo sapiens

<400> SEQUENCE: 80
gggttggacc ctcgtacaga agctaatacg actcactata gggaaataag agagaaaga      60 agagtaagaa gaaatataag agccaccccg cggtggcggc cgctctagaa ctagtggatc    120
ccccgggctg caggaattcg ataaaagcga tcgcccatca caagtttgta caaaaaagca    180
ggcttagcca ccatgtaccc atacgatgtt ccagattacg ctcctaagaa aaagaggaag    240
```

```
gtgcagagcg aggagatcca gggtcgtgag aagtcccggc ccgatcttgg cggggcctcc    300
aaggccaagc cacccacagc tccagcccct ccatcagctc ctgcaccttc tgcccagccc    360 acaccccgt cagcctctgt ccctggaaag aaggctcggg aggaagcccc agggccaccg     420
ggtgtcagcc gggccgacat gctgaagctg cgctcactta gtgaggggcc ccccaaggag    480
ctgaagatcc ggctcatcaa ggtagagagt ggtgacaagg agacctttat cgcctctgag    540
gtggaagagc ggcggctgcg catggcagac ctcaccatca gccactgtgc tgctgacgtc    600
gtgcgcgcca gcaggaatgc caaggtgaaa gggaagtttc gagagtccta cctttcccct    660
gcccagtctg tgaaaccgaa gatcaacact gaggagaagc tgccccggga aaaactcaac    720 cccctacac ccagcatcta tctggagagc aaacgggatg ccttctcacc tgtcctgctg     780
cagttctgta cagaccctcg aaatcccatc acagtgatcc ggggcctggc gggctccctg    840
cggctcaact tgggcctctt ctccaccaag accctggtgg aagcgagtgg cgaacacacc    900
gtggaagttc gcacccaggt gcagcagccc tcagatgaga actgggatct gacaggcact    960
cggcagatct ggccttgtga gagctcccgt cccacaccac ccattgccaa gtacgcacag   1020
taccaggcct catccttcca ggagtctctg caggaggaga aggagagtga ggatgaggag   1080
tcagaggagc cagacagcac cactggaacc cctcctagca gcgcaccaga cccgaagaac   1140
catcacatca tcaagtttgg caccaacatc gacttgtctg atgctaagcg gtggaagccc   1200
cagctgcagg agctgctgaa gctgcccgcc ttcatgcggg taacatccac gggcaacatg   1260
ctgagccacg tgggccacac catcctgggc atgaacacgg tgcagctgta catgaaggtg   1320
cccggcagcc gaacgccagg ccaccaggag aataacaact tctgctccgt caacatcaac   1380
attgccccag gcgactgcga gtggttcgcg gtgcacgagc actactggga gaccatcagc   1440
gctttctgtg atcggcacgg cgtggactac ttgacgggtt cctggtggcc aatcctggat   1500
gatctctatg catccaatat tcctgtgtac cgcttcgtgc agcgacccgg agacctcgtg   1560
tggattaatg cggggactgt gcactgggtg caggccaccg gctggtgcaa caacattgcc   1620
tggaacgtgg ggccctcac cgcctatcag taccagctgg ccctggaacg atacgagtgg   1680
aatgaggtga agaacgtcaa atccatcgtg cccatgattc acgtgtcatg gaacgtggct   1740
cgcacggtca aaatcagcga ccccgacttg ttcaagatga tcaagttctg cctgctgcag   1800
tccatgaagc actgccaggt gcaacgcgag agcctggtgc gggcagggaa gaaaatcgct   1860
taccagggcc gtgtcaagga cgagccagcc tactactgca acgagtgcga tgtggaggtg   1920
tttaacatcc tgttcgtgac aagtgagaat ggcagccgca acacgtacct ggtacactgc   1980
gagggctgtg cccggcgccg cagcgcaggc ctgcagggct ggtggtgct ggagcagtac    2040 cgcactgagg agctggctca ggcctacgac gccttcacgc tggtgagggc ccggcgggcg   2100
cgcgggcagc ggaggagggc actggggcag gctgcaggga cgggcttcgg gagcccggcc   2160
gcgcctttcc ctgagccccc gccggctttc tccccccagg ccccagccag cacgtcgcga   2220
tgaacccagc tttcttgtac aaagtggtga tggccgctgt ttaaaacttt tatcaagctt   2280
atcgataccg tcgacctcga atgctgcctt ctgcggggct tgccttctgg ccatgccctt   2340
cttctctccc ttgcacctgt acctcttggt ctttgaataa agcctgagta ggaagtgagg   2400
gtctagaact agtgtcgacg caaaaaaaaa aaaaaaaaa aaaaaaaaaa aaaaaaaaa     2460 aaaaaaaaaa aaaaaaaaa aaaaaaaa aaaaaaaaaa aaaaaaaaaa aaaaaaaaa       2520 aaaaaaaaaa aaaaaaaaa a                                               2541
```

<210> SEQ ID NO 81
<211> LENGTH: 1222
<212> TYPE: DNA
<213> ORGANISM: Homo sapiens

<400> SEQUENCE: 81

| | | | | | | |
|---|---|---|---|---|---|---|
| gggttggacc | ctcgtacaga | agctaatacg | actcactata | gggaaataag | agagaaaaga | 60 |
| agagtaagaa | gaaatataag | agccaccccg | cggtggcggc | cgctctagaa | ctagtggatc | 120 |
| ccccgggctg | caggaattcg | ataaaagcga | tcgcccatca | caagtttgta | caaaaaagca | 180 |
| ggctccacca | tgccagcccg | ccttgagacc | tgcatctccg | acctcgactg | cgccagcagc | 240 |
| agcggcagtg | acctatccgg | cttcctcacc | gacgaggaag | actgtgccag | actccaacag | 300 |
| gcagcctccg | cttcggggcc | gcccgcgccg | gcccgcaggg | gcgcgcccaa | tatctcccgg | 360 |
| gcgtctgagg | ttccagggc | acaggacgac | gagcaggaga | ggcggcggcg | ccgcggccgg | 420 |
| acgcgggtcc | gctccgaggc | gctgctgcac | tcgctgcgca | ggagccggcg | cgtcaaggcc | 480 |
| aacgatcgcg | agcgcaaccg | catgcacaac | ttgaacgcgg | ccctggacgc | actgcgcagc | 540 |
| gtgctgccct | cgttccccga | cgacaccaag | ctcaccaaaa | tcgagacgct | gcgcttcgcc | 600 |
| tacaactaca | tctgggctct | ggccgagaca | ctgcgcctgg | cggatcaagg | gctgcccgga | 660 |
| ggcggtgccc | gggagcgcct | cctgccgccg | cagtgcgtcc | cctgcctgcc | cggtcccca | 720 |
| agccccgcca | gcgacgcgga | gtcctggggc | tcaggtgccg | ccgccgcctc | cccgctctct | 780 |
| gaccccagta | gcccagccgc | ctccgaagac | ttcacctacc | gccccggcga | ccctgttttc | 840 |
| tccttcccaa | gctgcccaa | agacttgctc | cacacaacgc | cctgtttcat | tccttaccac | 900 |
| taggacccag | ctttcttgta | caaagtggtg | atggccgctg | tttaaaactt | ttatcaagct | 960 |
| tatcgatacc | gtcgacctcg | aatgctgcct | tctgcgggc | ttgccttctg | gccatgccct | 1020 |
| tcttctctcc | cttgcacctg | tacctcttgg | tctttgaata | aagcctgagt | aggaagtgag | 1080 |
| ggtctagaac | tagtgtcgac | gcaaaaaaaa | aaaaaaaaaa | aaaaaaaaaa | aaaaaaaaaa | 1140 |
| aaaaaaaaaa | aaaaaaaaaa | aaaaaaaaaa | aaaaaaaaaa | aaaaaaaaaa | aaaaaaaaaa | 1200 |
| aaaaaaaaaa | aaaaaaaaaa | aa | | | | 1222 |

<210> SEQ ID NO 82
<211> LENGTH: 1357
<212> TYPE: DNA
<213> ORGANISM: Homo sapiens

<400> SEQUENCE: 82

| | | | | | | |
|---|---|---|---|---|---|---|
| gggttggacc | ctcgtacaga | agctaatacg | actcactata | gggaaataag | agagaaaaga | 60 |
| agagtaagaa | gaaatataag | agccaccccg | cggtggcggc | cgctctagaa | ctagtggatc | 120 |
| ccccgggctg | caggaattcg | ataaaagcga | tcgcccatca | caagtttgta | caaaaaagca | 180 |
| ggctccgcgg | ccgcccccctt | caccatgttc | gtcaaatccg | agaccttgga | gttgaaggag | 240 |
| gaagaggacg | tgttagtgct | gctcggatcg | gcctcccccg | ccttggcggc | cctgaccccg | 300 |
| ctgtcatcca | gcgccgacga | agaagaggag | gaggagccgg | gcgcgtcagg | tggggcgcgt | 360 |
| cggcagcgcg | gggctgaggc | cgggcagggg | gcgcggggcg | gcgtggctgc | gggtgcggag | 420 |
| ggctgccggc | ccgcacggct | gctgggtctg | gtacacgatt | gcaaacggcg | cccttcccgg | 480 |
| gcgcgggccc | tctcccgagg | cgccaagacg | gccgagacgg | tgcagcgcat | caagaagacc | 540 |
| cgtagactga | aggccaacaa | ccgcgagcga | aaccgcatgc | acaacctcaa | cgcggcactg | 600 |
| gacgcgctgc | gcgaggtgct | ccccacgttc | cccgaggacg | ccaagctcac | caagatcgag | 660 |

| | |
|---|---|
| accctgcgct tcgcccacaa ctacatctgg gcactcaccg agaccctgcg cctggcggat | 720 |
| cactgcgggg gcggcggcgg gggcctgccg ggggcgctct tctccgaggc agtgttgctg | 780 |
| agcccgggag gcgccagcgc cgccctgagc agcagcggag acagcccctc gcccgcctcc | 840 |
| acgtggagtt gcaccaacag ccccgcgccg tcctcctccg tgtcctccaa ttccacctcc | 900 |
| ccctacagct gcactttatc gcccgccagc ccggccgggt cagacatgga ctattggcag | 960 |
| cccccacctc ccgacaagca ccgctatgca cctcacctcc ccatagccag ggattgtatc | 1020 |
| tagaagggtg ggcgcgccga cccagctttc ttgtacaaag tggtgatggc cgctgtttaa | 1080 |
| aactttatc aagcttatcg ataccgtcga cctcgaatgc tgccttctgc ggggcttgcc | 1140 |
| ttctggccat gcccttcttc tctcccttgc acctgtacct cttggtcttt gaataaagcc | 1200 |
| tgagtaggaa gtgagggtct agaactagtg tcgacgcaaa aaaaaaaaaa aaaaaaaaaa | 1260 |
| aaaaaaaaaa aaaaaaaaaa aaaaaaaaaa aaaaaaaaaa aaaaaaaaaa aaaaaaaaaa | 1320 |
| aaaaaaaaaa aaaaaaaaaa aaaaaaaaaa aaaaaaa | 1357 |

<210> SEQ ID NO 83
<211> LENGTH: 1153
<212> TYPE: DNA
<213> ORGANISM: Homo sapiens

<400> SEQUENCE: 83

| | |
|---|---|
| gggttggacc ctcgtacaga agctaatacg actcactata gggaaataag agagaaaga | 60 |
| agagtaagaa gaaatataag agccacccccg cggtggcggc cgctctagaa ctagtggatc | 120 |
| ccccgggctg caggaattcg ataaaagcga tcgcccatca caagtttgta caaaaaagca | 180 |
| ggcttcacca tgacgcctca accctcgggt gcgcccactg tccaagtgac ccgtgagacg | 240 |
| gagcggtcct tccccagagc ctcggaagac gaagtgacct gccccacgtc cgccccgccc | 300 |
| agccccactc gcacacgggg gaactgcgca gaggcggaag agggaggctg ccgaggggcc | 360 |
| ccgaggaagc tccgggcacg gcgcggggga cgcagccggc ctaagagcga gttggcactg | 420 |
| agcaagcagc gacggagtcg gcgaaagaag gccaacgacc gcgagcgcaa tcgaatgcac | 480 |
| aacctcaact cggcactgga cgccctgcgc ggtgtcctgc ccaccttccc agacgacgcg | 540 |
| aagctcacca agatcgagac gctgcgcttc gcccacaact acatctgggc gctgactcaa | 600 |
| acgctgcgca tagcggacca cagcttgtac gcgctggagc cgccggcgcc gcactgcggg | 660 |
| gagctgggca gcccaggcgg ttcccccggg gactgggggt ccctctactc cccagtctcc | 720 |
| caggctggca gcctgagtcc cgccgcgtcg ctggaggagc gacccgggct gctgggggcc | 780 |
| accttttccg cctgcttgag cccaggcagt ctggctttct cagattttct gtgagaccca | 840 |
| gctttcttgt acaaagtggt gatggccgct gtttaaaact tttatcaagc ttatcgatac | 900 |
| cgtcgacctc gaatgctgcc ttctgcgggg cttgccttct ggccatgccc ttcttctctc | 960 |
| ccttgcacct gtacctcttg gtctttgaat aaagcctgag taggaagtga gggtctagaa | 1020 |
| ctagtgtcga cgcaaaaaaa aaaaaaaaaa aaaaaaaaaa aaaaaaaaaa aaaaaaaaaa | 1080 |
| aaaaaaaaaa aaaaaaaaaa aaaaaaaaaa aaaaaaaaaa aaaaaaaaaa aaaaaaaaaa | 1140 |
| aaaaaaaaaa aaa | 1153 |

<210> SEQ ID NO 84
<211> LENGTH: 1609
<212> TYPE: DNA
<213> ORGANISM: Homo sapiens

<400> SEQUENCE: 84

```
gggttggacc ctcgtacaga agctaatacg actcactata gggaaataag agagaaaaga      60
agagtaagaa gaaatataag agccaccccg cggtggcggc cgctctagaa ctagtggatc     120
ccccgggctg caggaattcg ataaaagcga tcgcccatca caagtttgta caaaaaagca     180
ggctccgcgg ccgccccctt caccatgacc aaatcgtaca gcgagagtgg gctgatgggc     240
gagcctcagc cccaaggtcc tccaagctgg acagacgagt gtctcagttc tcaggacgag     300
gagcacgagg cagacaagaa ggaggacgac ctcgaagcca tgaacgcaga ggaggactca     360
ctgaggaacg gggagagga ggaggacgaa gatgaggacc tggaagagga ggaagaagag     420
gaagaggagg atgacgatca aaagcccaag agacgcggcc ccaaaaagaa gagatgact     480
aaggctcgcc tggagcgttt taaattgaga cgcatgaagg ctaacgcccg ggagcggaac     540
cgcatgcacg gactgaacgc ggcgctagac aacctgcgca aggtggtgcc ttgctattct     600
aagacgcaga agctgtccaa aatcgagact ctgcgcttgg ccaagaacta catctgggct     660
ctgtcggaga tcctgcgctc aggcaaaagc ccagacctgg tctccttcgt tcagacgctt     720
tgcaagggct atcccaacc caccaccaac ctggttgcgg gctgcctgca actcaatcct     780
cggactttc tgcctgagca gaaccaggac atgccccccc acctgccgac ggccagcgct     840
tccttccctg tacaccccta ctcctaccag tcgcctgggc tgcccagtcc gccttacggt     900
accatggaca gctcccatgt cttccacgtt aagcctccgc cgcacgccta cagcgcagcg     960
ctggagccct tctttgaaag ccctctgact gattgcacca gccttccctt tgatggaccc    1020
ctcagcccgc cgctcagcat caatggcaac ttctctttca acacgaacc gtccgccgag    1080
tttgagaaaa attatgcctt taccatgcac tatcctgcag cgacactggc agggccccaa    1140
agccacggat caatcttctc aggcaccgct gcccctcgct gcgagatccc catagacaat    1200
attatgtcct tcgatagcca ttcacatcat gagcgagtca tgagtgccca gctcaatgcc    1260
atatttcatg attagaaggg tgggcgcgcc gacccagctt tcttgtacaa agtggtgatg    1320
gccgctgttt aaaacttta tcaagcttat cgataccgtc gacctcgaat gctgccttct    1380
gcggggcttg ccttctggcc atgccctct tctctcccctt gcacctgtac ctcttggtct    1440
ttgaataaag cctgagtagg aagtgagggt ctagaactag tgtcgacgca aaaaaaaaa    1500
aaaaaaaaa aaaaaaaaa aaaaaaaaa aaaaaaaaa aaaaaaaaa aaaaaaaaa    1560
aaaaaaaaa aaaaaaaaa aaaaaaaaa aaaaaaaaa aaaaaaaa    1609
```

<210> SEQ ID NO 85
<211> LENGTH: 1687
<212> TYPE: DNA
<213> ORGANISM: Homo sapiens

<400> SEQUENCE: 85

```
gggttggacc ctcgtacaga agctaatacg actcactata gggaaataag agagaaaaga      60
agagtaagaa gaaatataag agccaccccg cggtggcggc cgctctagaa ctagtggatc     120
ccccgggctg caggaattcg ataaaagcga tcgcccatca caagtttgta caaaaaagca     180
ggctccgcgg ccgccccctt caccatgctg accgcctgt tcagcgagcc ggccttctc     240
tcggacgtgc ccaagttcgc cagctgggc gacggcgaag acgacgagcc gaggagcgac     300
aagggcgacg cgccgccacc gccaccgct gcgcccgggc caggggctcc ggggccagcc     360
cggggcggcca agccagtccc tctccgtgga agaggggga cggaggccac gttgccgag     420
gtcaaggagg aaggcgagct ggggggagag gaggaggagg aagaggagga ggaagaagga     480
```

```
ctggacgagg cggagggcga gcggcccaag aagggcgggc ccaagaagcg caagatgacc      540
aaggcgcgct tggagcgctc caagcttcgg cggcagaagg cgaacgcgcg ggagcgcaac      600
cgcatgcacg acctgaacgc agccctggac aacctgcgca aggtggtgcc ctgctactcc      660
aagacgcaga agctgtccaa gatcgagacg ctgcgcctag ccaagaacta tatctgggcg      720
ctctcggaga tcctgcgctc cggcaagcgg ccagacctag tgtcctacgt gcagactctg      780
tgcaagggtc tgtcgcagcc caccaccaat ctggtggccg gctgtctgca gctcaactct      840
cgcaacttcc tcacggagca aggcgccgac ggtgccggcc gcttccacgg ctcgggcggc      900
ccgttcgcca tgcacccta cccgtacccg tgctcgcgcc tggcgggcgc acagtgccag      960
gcggccggcg gcctgggcgg cggcgcggcg cacgccctgc ggacccacgg ctactgcgca     1020
gcctacgaga cgctgtatgc ggcggcaggc ggtggcggcg cgagcccgga ctacaacagc     1080
tccgagtacg agggcccgct cagcccccg ctctgtctca atggcaactt ctcactcaag     1140
caggactcct cgcccgacca cgagaaaagc taccactact ctatgcacta ctcggcgctg     1200
cccggttcgc ggcccacggg ccacgggcta gtcttcggct cgtcggctgt gcgcgggggc     1260
gtccactcgg agaatctctt gtcttacgat atgcaccttc accacgaccg gggccccatg     1320
tacgaggagc tcaatgcgtt ttttcataac tgaaagggtg ggcgcgccga cccagctttc     1380
ttgtacaaag tggtgatggc cgctgtttaa aactttatc aagcttatcg ataccgtcga     1440
cctcgaatgc tgccttctgc ggggcttgcc ttctggccat gcccttcttc tctcccttgc     1500
acctgtacct cttggtcttt gaataaagcc tgagtaggaa gtgagggtct agaactagtg     1560
tcgacgcaaa aaaaaaaaa aaaaaaaaaa aaaaaaaaaa aaaaaaaaaa aaaaaaaaaa     1620
aaaaaaaaaa aaaaaaaaaa aaaaaaaaaa aaaaaaaaaa aaaaaaaaaa aaaaaaaaaa     1680
aaaaaaa                                                                1687

<210> SEQ ID NO 86
<211> LENGTH: 1574
<212> TYPE: DNA
<213> ORGANISM: Homo sapiens

<400> SEQUENCE: 86
gggttggacc ctcgtacaga agctaatacg actcactata gggaaataag agagaaaaga       60
agagtaagaa gaaatataag agccaccccg cggtggcggc cgctctagaa ctagtggatc      120
ccccgggctg caggaattcg ataaaagcga tcgcccatca caagtttgta caaaaaagca      180
ggctccgcgg ccgcccccttt caccgctagg gataacaggg taatagaagg agccgccacc      240
atggagctac tgtcgccacc gctccgcgac gtagacctga cggcccccga cggctctctc      300
tgctcctttg ccacaacgga cgacttctat gacgacccgt gtttcgactc cccggacctg      360
cgcttcttcg aagacctgga cccgcgcctg atgcacgtgg gcgcgctcct gaaacccgaa      420
gagcactcgc acttccccgc ggcggtgcac ccggcccggg gcgcacgtga ggacgagcat      480
gtgcgcgcgc ccagcgggca ccaccaggcg ggccgctgcc tactgtgggc ctgcaaggcg      540
tgcaagcgca agaccaccaa cgccgaccgc cgcaaggccg ccaccatgcg cgagcggcgc      600
cgcctgagca aagtaaatga ggccttttgag acactcaagc gctgcacgtc gagcaatcca      660
aaccagcggt tgcccaaggt ggagatcctg cgcaacgcca tccgctatat cgagggcctg      720
caggctctgc tgcgcgacca ggagccgcgc cccctggcg ccgcagccgc cttctatgcg      780
ccgggcccgc tgccccgggg ccgcggcggc gagcactaca gcggcgactc cgacgcgtcc      840
agcccgcgct ccaactgctc cgacggcatg atggactaca gcggcccccc gagcggcgcc      900
```

| | |
|---|---|
| cggcggcgga actgctacga aggcgcctac tacaacgagg cgcccagcga acccaggccc | 960 |
| gggaagagtg cggcggtgtc gagcctagac tgcctgtcca gcatcgtgga gcgcatctcc | 1020 |
| accgagagcc ctgcggcgcc cgccctcctg ctggcggacg tgccttctga gtcgcctccg | 1080 |
| cgcaggcaag aggctgccgc ccccagcgag ggagagagca gcggcgaccc cacccagtca | 1140 |
| ccggacgccg ccccgcagtg ccctgcgggt gcgaaccccca acccgatata ccaggtgctc | 1200 |
| tgagtttcct gtgaacaatt gctcctctct taaggtagca aagggtgggc gcgccgaccc | 1260 |
| agctttcttg tacaaagtgg tgatggccgc tgtttaaaac ttttatcaag cttatcgata | 1320 |
| ccgtcgacct cgaatgctgc cttctgcggg gcttgccttc tggccatgcc cttcttctct | 1380 |
| cccttgcacc tgtacctctt ggtctttgaa taaagcctga gtaggaagtg agggtctaga | 1440 |
| actagtgtcg acgcaaaaaa aaaaaaaaaa aaaaaaaaaa aaaaaaaaaa aaaaaaaaaa | 1500 |
| aaaaaaaaaa aaaaaaaaaa aaaaaaaaaa aaaaaaaaaa aaaaaaaaaa aaaaaaaaaa | 1560 |
| aaaaaaaaaa aaaa | 1574 |

<210> SEQ ID NO 87
<211> LENGTH: 2414
<212> TYPE: DNA
<213> ORGANISM: Homo sapiens

<400> SEQUENCE: 87

| | |
|---|---|
| gggttggacc ctcgtacaga agctaatacg actcactata gggaaataag agagaaaaga | 60 |
| agagtaagaa gaaatataag agccaccccg cggtggcggc cgctctagaa ctagtggatc | 120 |
| ccccgggctg caggaattcg ataaaagcga tcgcccatca caagtttgta caaaaaagca | 180 |
| ggctccacca tggtttctaa actgagccag ctgcagacgg agctcctggc ggccctgctg | 240 |
| gagtcagggc tgagcaaaga ggcactgctc caggcactgg gtgagccggg gccctacctc | 300 |
| ctggctggag aaggccccct ggacaagggg gagtcctgcg gcggcggtcg aggggagctg | 360 |
| gctgagctgc ccaatgggct gggggagact cggggctccg aggacgagac ggacgacgat | 420 |
| ggggaagact tcacgccacc catcctcaaa gagctggaga acctcagccc tgaggaggcg | 480 |
| gcccaccaga aagccgtggt ggagacccctt ctgcaggagg acccgtggcg tgtggcgaag | 540 |
| atggtcaagt cctacctgca gcagcacaac atcccacagc gggaggtggt cgataccact | 600 |
| ggcctcaacc agtcccacct gtcccaacac ctcaacaagg gcactcccat gaagacgcag | 660 |
| aagcgggccg ccctgtacac ctggtacgtc cgcaagcagc gagaggtggc gcagcagttc | 720 |
| acccatgcag ggcagggagg gctgattgaa gagcccacag gtgatgagct accaaccaag | 780 |
| aaggggcgga ggaaccgttt caagtggggc ccagcatccc agcagatcct gttccaggcc | 840 |
| tatgagaggc agaagaaccc tagcaaggag gagcgagaga cgctagtgga ggagtgcaat | 900 |
| agggcggaat gcatccagag aggggtgtcc ccatcacagg cacaggggct gggctccaac | 960 |
| ctcgtcacgg aggtgcgtgt ctacaactgg tttgccaacc ggcgcaaaga agaagccttc | 1020 |
| cggcacaagc tggccatgga cacgtacagc gggcccccc cagggccagg cccgggacct | 1080 |
| gcgctgcccg ctcacagctc ccctggcctg cctccacctg ccctctcccc cagtaaggtc | 1140 |
| cacggtgtgc gctatggaca gcctgcgacc agtgagactg cagaagtacc ctcaagcagc | 1200 |
| ggcggtccct tagtgacagt gtctacaccc ctccaccaag tgtccccac gggcctggag | 1260 |
| cccagccaca gcctgctgag tacagaagcc aagctggtct cagcagctgg ggccccctc | 1320 |
| cccccctgtca gcaccctgac agcactgcac agcttggagc agacatcccc aggcctcaac | 1380 |
| cagcagcccc agaacctcat catggcctca cttcctgggg tcatgaccat cgggcctggt | 1440 |

```
gagcctgcct ccctgggtcc tacgttcacc aacacaggtg cctccaccct ggtcatcggc    1500
ctggcctcca cgcaggcaca gagtgtgccg gtcatcaaca gcatgggcag cagcctgacc    1560
accctgcagc ccgtccagtt ctcccagccg ctgcaccccc tctaccagca gccgctcatg    1620
ccacctgtgc agagccatgt gacccagagc cccttcatgg ccaccatggc tcagctgcag    1680 agccccacg ccctctacag ccacaagccc gaggtggccc agtacaccca cacaggcctg    1740
ctcccgcaga ctatgctcat caccgacacc accaacctga cgccctggcc agcctcacg    1800 cccaccaagc aggtcttcac ctcagacact gaggcctcca gtgagtccgg gcttcacacg    1860
ccggcatctc aggccaccac cctccacgtc cccagccagg accctgccgg catccagcac    1920
ctgcagccgg cccaccggct cagcgccagc cccacagtgt cctccagcag cctggtgctg    1980
taccagagct cagactccag caatggccag agccacctgc tgccatccaa ccacagcgtc    2040
atcgagacct tcatctccac ccagatggcc tcttcctccc agttgtgagc ggccgcaccc    2100
agctttcttg tacaaagtgg tgatggccgc tgtttaaaac ttttatcaag cttatcgata    2160
ccgtcgacct cgaatgctgc cttctgcggg gcttgccttc tggccatgcc cttcttctct    2220
cccttgcacc tgtacctctt ggtctttgaa taaagcctga gtaggaagtg agggtctaga    2280
actagtgtcg acgcaaaaaa aaaaaaaaaa aaaaaaaaaa aaaaaaaaaa aaaaaaaaaa    2340
aaaaaaaaaa aaaaaaaaaa aaaaaaaaaa aaaaaaaaaa aaaaaaaaaa aaaaaaaaaa    2400
aaaaaaaaaa aaaa                                                      2414

<210> SEQ ID NO 88
<211> LENGTH: 320
<212> TYPE: PRT
<213> ORGANISM: Homo sapiens

<400> SEQUENCE: 88

Met Glu Leu Leu Ser Pro Pro Leu Arg Asp Val Asp Leu Thr Ala Pro
1               5                   10                  15

Asp Gly Ser Leu Cys Ser Phe Ala Thr Thr Asp Asp Phe Tyr Asp Asp
            20                  25                  30

Pro Cys Phe Asp Ser Pro Asp Leu Arg Phe Phe Glu Asp Leu Asp Pro
        35                  40                  45

Arg Leu Met His Val Gly Ala Leu Leu Lys Pro Glu Glu His Ser His
    50                  55                  60

Phe Pro Ala Ala Val His Pro Ala Pro Gly Ala Arg Glu Asp Glu His
65                  70                  75                  80

Val Arg Ala Pro Ser Gly His His Gln Ala Gly Arg Cys Leu Leu Trp
                85                  90                  95

Ala Cys Lys Ala Cys Lys Arg Lys Thr Thr Asn Ala Asp Arg Arg Lys
            100                 105                 110

Ala Ala Thr Met Arg Glu Arg Arg Arg Leu Ser Lys Val Asn Glu Ala
        115                 120                 125

Phe Glu Thr Leu Lys Arg Cys Thr Ser Ser Asn Pro Asn Gln Arg Leu
    130                 135                 140

Pro Lys Val Glu Ile Leu Arg Asn Ala Ile Arg Tyr Ile Glu Gly Leu
145                 150                 155                 160

Gln Ala Leu Leu Arg Asp Gln Asp Ala Ala Pro Pro Gly Ala Ala Ala
                165                 170                 175

Ala Phe Tyr Ala Pro Gly Pro Leu Pro Pro Gly Arg Gly Gly Glu His
            180                 185                 190
```

Tyr Ser Gly Asp Ser Asp Ala Ser Pro Arg Ser Asn Cys Ser Asp
            195                 200                 205

Gly Met Met Asp Tyr Ser Gly Pro Pro Ser Gly Ala Arg Arg Arg Asn
210                 215                 220

Cys Tyr Glu Gly Ala Tyr Tyr Asn Glu Ala Pro Ser Glu Pro Arg Pro
225                 230                 235                 240

Gly Lys Ser Ala Ala Val Ser Ser Leu Asp Cys Leu Ser Ser Ile Val
            245                 250                 255

Glu Arg Ile Ser Thr Glu Ser Pro Ala Ala Pro Ala Leu Leu Leu Ala
            260                 265                 270

Asp Val Pro Ser Glu Ser Pro Arg Arg Gln Glu Ala Ala Ala Pro
            275                 280                 285

Ser Glu Gly Glu Ser Ser Gly Asp Pro Thr Gln Ser Pro Asp Ala Ala
            290                 295                 300

Pro Gln Cys Pro Ala Gly Ala Asn Pro Asn Pro Ile Tyr Gln Val Leu
305                 310                 315                 320

<210> SEQ ID NO 89
<211> LENGTH: 237
<212> TYPE: PRT
<213> ORGANISM: Homo sapiens

<400> SEQUENCE: 89

Met Pro Ala Arg Leu Glu Thr Cys Ile Ser Asp Leu Asp Cys Ala Ser
1               5                   10                  15

Ser Ser Gly Ser Asp Leu Ser Gly Phe Leu Thr Asp Glu Glu Asp Cys
            20                  25                  30

Ala Arg Leu Gln Gln Ala Ala Ser Ala Ser Gly Pro Pro Ala Pro Ala
        35                  40                  45

Arg Arg Gly Ala Pro Asn Ile Ser Arg Ala Ser Glu Val Pro Gly Ala
    50                  55                  60

Gln Asp Asp Glu Gln Glu Arg Arg Arg Arg Gly Arg Thr Arg Val
65                  70                  75                  80

Arg Ser Glu Ala Leu Leu His Ser Leu Arg Arg Ser Arg Val Lys
                85                  90                  95

Ala Asn Asp Arg Glu Arg Asn Arg Met His Asn Leu Asn Ala Ala Leu
            100                 105                 110

Asp Ala Leu Arg Ser Val Leu Pro Ser Phe Pro Asp Thr Lys Leu
        115                 120                 125

Thr Lys Ile Glu Thr Leu Arg Phe Ala Tyr Asn Tyr Ile Trp Ala Leu
130                 135                 140

Ala Glu Thr Leu Arg Leu Ala Asp Gln Gly Leu Pro Gly Gly Gly Ala
145                 150                 155                 160

Arg Glu Arg Leu Leu Pro Pro Gln Cys Val Pro Cys Leu Pro Gly Pro
                165                 170                 175

Pro Ser Pro Ala Ser Asp Ala Glu Ser Trp Gly Ser Gly Ala Ala Ala
            180                 185                 190

Ala Ser Pro Leu Ser Asp Pro Ser Ser Pro Ala Ala Ser Glu Asp Phe
        195                 200                 205

Thr Tyr Arg Pro Gly Asp Pro Val Phe Ser Phe Pro Ser Leu Pro Lys
    210                 215                 220

Asp Leu Leu His Thr Thr Pro Cys Phe Ile Pro Tyr His
225                 230                 235

-continued

<210> SEQ ID NO 90
<211> LENGTH: 272
<212> TYPE: PRT
<213> ORGANISM: Homo sapiens

<400> SEQUENCE: 90

Met Phe Val Lys Ser Glu Thr Leu Glu Leu Lys Glu Glu Glu Asp Val
1               5                   10                  15

Leu Val Leu Leu Gly Ser Ala Ser Pro Ala Leu Ala Ala Leu Thr Pro
            20                  25                  30

Leu Ser Ser Ser Ala Asp Glu Glu Glu Glu Glu Pro Gly Ala Ser
        35                  40                  45

Gly Gly Ala Arg Arg Gln Arg Gly Ala Glu Ala Gly Gln Gly Ala Arg
    50                  55                  60

Gly Gly Val Ala Ala Gly Ala Glu Gly Cys Arg Pro Ala Arg Leu Leu
65                  70                  75                  80

Gly Leu Val His Asp Cys Lys Arg Arg Pro Ser Arg Ala Arg Ala Val
                85                  90                  95

Ser Arg Gly Ala Lys Thr Ala Glu Thr Val Gln Arg Ile Lys Lys Thr
            100                 105                 110

Arg Arg Leu Lys Ala Asn Asn Arg Glu Arg Asn Arg Met His Asn Leu
        115                 120                 125

Asn Ala Ala Leu Asp Ala Leu Arg Glu Val Leu Pro Thr Phe Pro Glu
    130                 135                 140

Asp Ala Lys Leu Thr Lys Ile Glu Thr Leu Arg Phe Ala His Asn Tyr
145                 150                 155                 160

Ile Trp Ala Leu Thr Glu Thr Leu Arg Leu Ala Asp His Cys Gly Gly
                165                 170                 175

Gly Gly Gly Gly Leu Pro Gly Ala Leu Phe Ser Glu Ala Val Leu Leu
            180                 185                 190

Ser Pro Gly Gly Ala Ser Ala Ala Leu Ser Ser Ser Gly Asp Ser Pro
        195                 200                 205

Ser Pro Ala Ser Thr Trp Ser Cys Thr Asn Ser Pro Ala Pro Ser Ser
    210                 215                 220

Ser Val Ser Ser Asn Ser Thr Ser Pro Tyr Ser Cys Thr Leu Ser Pro
225                 230                 235                 240

Ala Ser Pro Ala Gly Ser Asp Met Asp Tyr Trp Gln Pro Pro Pro
                245                 250                 255

Asp Lys His Arg Tyr Ala Pro His Leu Pro Ile Ala Arg Asp Cys Ile
            260                 265                 270

<210> SEQ ID NO 91
<211> LENGTH: 214
<212> TYPE: PRT
<213> ORGANISM: Homo sapiens

<400> SEQUENCE: 91

Met Thr Pro Gln Pro Ser Gly Ala Pro Thr Val Gln Val Thr Arg Glu
1               5                   10                  15

Thr Glu Arg Ser Phe Pro Arg Ala Ser Glu Asp Glu Val Thr Cys Pro
            20                  25                  30

Thr Ser Ala Pro Pro Ser Pro Thr Arg Thr Arg Gly Asn Cys Ala Glu
        35                  40                  45

Ala Glu Glu Gly Gly Cys Arg Gly Ala Pro Arg Lys Leu Arg Ala Arg
    50                  55                  60

-continued

Arg Gly Gly Arg Ser Arg Pro Lys Ser Glu Leu Ala Leu Ser Lys Gln
65                  70                  75                  80

Arg Arg Ser Arg Arg Lys Lys Ala Asn Asp Arg Glu Arg Asn Arg Met
                85                  90                  95

His Asn Leu Asn Ser Ala Leu Asp Ala Leu Arg Gly Val Leu Pro Thr
            100                 105                 110

Phe Pro Asp Asp Ala Lys Leu Thr Lys Ile Glu Thr Leu Arg Phe Ala
        115                 120                 125

His Asn Tyr Ile Trp Ala Leu Thr Gln Thr Leu Arg Ile Ala Asp His
    130                 135                 140

Ser Leu Tyr Ala Leu Glu Pro Ala Pro His Cys Gly Leu Gly Leu Gly
145                 150                 155                 160

Ser Pro Gly Gly Ser Pro Gly Asp Trp Gly Ser Leu Tyr Ser Pro Val
                165                 170                 175

Ser Gln Ala Gly Ser Leu Ser Pro Ala Ala Ser Leu Glu Glu Arg Pro
            180                 185                 190

Gly Leu Leu Gly Ala Thr Phe Ser Ala Cys Leu Ser Pro Gly Ser Leu
        195                 200                 205

Ala Phe Ser Asp Phe Leu
    210

<210> SEQ ID NO 92
<211> LENGTH: 356
<212> TYPE: PRT
<213> ORGANISM: Homo sapiens

<400> SEQUENCE: 92

Met Thr Lys Ser Tyr Ser Glu Ser Gly Leu Met Gly Glu Pro Gln Pro
1               5                   10                  15

Gln Gly Pro Pro Ser Trp Thr Asp Glu Cys Leu Ser Ser Gln Asp Glu
                20                  25                  30

Glu His Glu Ala Asp Lys Lys Glu Asp Asp Leu Glu Ala Met Asn Ala
            35                  40                  45

Glu Glu Asp Ser Leu Arg Asn Gly Gly Glu Glu Glu Asp Glu Asp Glu
        50                  55                  60

Asp Leu Glu Glu Glu Glu Glu Glu Glu Glu Asp Asp Asp Gln Lys
65                  70                  75                  80

Pro Lys Arg Arg Gly Pro Lys Lys Lys Lys Met Thr Lys Ala Arg Leu
                85                  90                  95

Glu Arg Phe Lys Leu Arg Arg Met Lys Ala Asn Ala Arg Glu Arg Asn
            100                 105                 110

Arg Met His Gly Leu Asn Ala Ala Leu Asp Asn Leu Arg Lys Val Val
        115                 120                 125

Pro Cys Tyr Ser Lys Thr Gln Lys Leu Ser Lys Ile Glu Thr Leu Arg
    130                 135                 140

Leu Ala Lys Asn Tyr Ile Trp Ala Leu Ser Glu Ile Leu Arg Ser Gly
145                 150                 155                 160

Lys Ser Pro Asp Leu Val Ser Phe Val Gln Thr Leu Cys Lys Gly Leu
                165                 170                 175

Ser Gln Pro Thr Thr Asn Leu Val Ala Gly Cys Leu Gln Leu Asn Pro
            180                 185                 190

Arg Thr Phe Leu Pro Glu Gln Asn Gln Asp Met Pro Pro His Leu Pro
        195                 200                 205

Thr Ala Ser Ala Ser Phe Pro Val His Pro Tyr Ser Tyr Gln Ser Pro
    210                 215                 220

```
Gly Leu Pro Ser Pro Tyr Gly Thr Met Asp Ser His Val Phe
225                 230                 235                 240

His Val Lys Pro Pro His Ala Tyr Ser Ala Ala Leu Glu Pro Phe
            245                 250                 255

Phe Glu Ser Pro Leu Thr Asp Cys Thr Ser Pro Ser Phe Asp Gly Pro
                260                 265                 270

Leu Ser Pro Pro Leu Ser Ile Asn Gly Asn Phe Ser Phe Lys His Glu
            275                 280                 285

Pro Ser Ala Glu Phe Glu Lys Asn Tyr Ala Phe Thr Met His Tyr Pro
        290                 295                 300

Ala Ala Thr Leu Ala Gly Ala Gln Ser His Gly Ser Ile Phe Ser Gly
305                 310                 315                 320

Thr Ala Ala Pro Arg Cys Glu Ile Pro Ile Asp Asn Ile Met Ser Phe
                325                 330                 335

Asp Ser His Ser His His Glu Arg Val Met Ser Ala Gln Leu Asn Ala
            340                 345                 350

Ile Phe His Asp
        355

<210> SEQ ID NO 93
<211> LENGTH: 382
<212> TYPE: PRT
<213> ORGANISM: Homo sapiens

<400> SEQUENCE: 93

Met Leu Thr Arg Leu Phe Ser Glu Pro Gly Leu Leu Ser Asp Val Pro
1               5                   10                  15

Lys Phe Ala Ser Trp Gly Asp Gly Glu Asp Asp Glu Pro Arg Ser Asp
                20                  25                  30

Lys Gly Asp Ala Pro Pro Pro Pro Ala Pro Gly Pro Gly Ala
            35                  40                  45

Pro Gly Pro Ala Arg Ala Ala Lys Pro Val Pro Leu Arg Gly Glu Glu
        50                  55                  60

Gly Thr Glu Ala Thr Leu Ala Glu Val Lys Glu Glu Gly Glu Leu Gly
65                  70                  75                  80

Gly Glu Glu Glu Glu Glu Glu Glu Glu Glu Gly Leu Asp Glu Ala
                85                  90                  95

Glu Gly Glu Arg Pro Lys Lys Gly Gly Pro Lys Lys Arg Lys Met Thr
            100                 105                 110

Lys Ala Arg Leu Glu Arg Ser Lys Leu Arg Arg Gln Lys Ala Asn Ala
        115                 120                 125

Arg Glu Arg Asn Arg Met His Asp Leu Asn Ala Ala Leu Asp Asn Leu
130                 135                 140

Arg Lys Val Val Pro Cys Tyr Ser Lys Thr Gln Lys Leu Ser Lys Ile
145                 150                 155                 160

Glu Thr Leu Arg Leu Ala Lys Asn Tyr Ile Trp Ala Leu Ser Glu Ile
                165                 170                 175

Leu Arg Ser Gly Lys Arg Pro Asp Leu Val Ser Tyr Val Gln Thr Leu
            180                 185                 190

Cys Lys Gly Leu Ser Gln Pro Thr Thr Asn Leu Val Ala Gly Cys Leu
        195                 200                 205

Gln Leu Asn Ser Arg Asn Phe Leu Thr Glu Gln Gly Ala Asp Gly Ala
210                 215                 220

Gly Arg Phe His Gly Ser Gly Gly Pro Phe Ala Met His Pro Tyr Pro
225                 230                 235                 240
```

```
Tyr Pro Cys Ser Arg Leu Ala Gly Ala Gln Cys Gln Ala Ala Gly Gly
                245                 250                 255

Leu Gly Gly Gly Ala Ala His Ala Leu Arg Thr His Gly Tyr Cys Ala
            260                 265                 270

Ala Tyr Glu Thr Leu Tyr Ala Ala Gly Gly Gly Gly Ala Ser Pro
        275                 280                 285

Asp Tyr Asn Ser Ser Glu Tyr Glu Gly Pro Leu Ser Pro Pro Leu Cys
        290                 295                 300

Leu Asn Gly Asn Phe Ser Leu Lys Gln Asp Ser Ser Pro Asp His Glu
305                 310                 315                 320

Lys Ser Tyr His Tyr Ser Met His Tyr Ser Ala Leu Pro Gly Ser Arg
                325                 330                 335

Pro Thr Gly His Gly Leu Val Phe Gly Ser Ser Ala Val Arg Gly Gly
                340                 345                 350

Val His Ser Glu Asn Leu Leu Ser Tyr Asp Met His Leu His His Asp
            355                 360                 365

Arg Gly Pro Met Tyr Glu Glu Leu Asn Ala Phe Phe His Asn
370                 375                 380

<210> SEQ ID NO 94
<211> LENGTH: 632
<212> TYPE: PRT
<213> ORGANISM: Homo sapiens

<400> SEQUENCE: 94

Met Val Ser Lys Leu Ser Gln Leu Gln Thr Glu Leu Leu Ala Ala Leu
1               5                   10                  15

Leu Glu Ser Gly Leu Ser Lys Glu Ala Leu Leu Gln Ala Leu Gly Glu
            20                  25                  30

Pro Gly Pro Tyr Leu Leu Ala Gly Glu Gly Pro Leu Asp Lys Gly Glu
        35                  40                  45

Ser Cys Gly Gly Gly Arg Gly Glu Leu Ala Glu Leu Pro Asn Gly Leu
    50                  55                  60

Gly Glu Thr Arg Gly Ser Glu Asp Glu Thr Asp Asp Asp Gly Glu Asp
65                  70                  75                  80

Phe Thr Pro Pro Ile Leu Lys Glu Leu Glu Asn Leu Ser Pro Glu Glu
                85                  90                  95

Ala Ala His Gln Lys Ala Val Val Glu Thr Leu Leu Gln Glu Asp Pro
            100                 105                 110

Trp Arg Val Ala Lys Met Val Lys Ser Tyr Leu Gln Gln His Asn Ile
        115                 120                 125

Pro Gln Arg Glu Val Val Asp Thr Thr Gly Leu Asn Gln Ser His Leu
    130                 135                 140

Ser Gln His Leu Asn Lys Gly Thr Pro Met Lys Thr Gln Lys Arg Ala
145                 150                 155                 160

Ala Leu Tyr Thr Trp Tyr Val Arg Lys Gln Arg Glu Val Ala Gln Gln
                165                 170                 175

Phe Thr His Ala Gly Gln Gly Gly Leu Ile Glu Glu Pro Thr Gly Asp
            180                 185                 190

Glu Leu Pro Thr Lys Lys Gly Arg Arg Asn Arg Phe Lys Trp Gly Pro
        195                 200                 205

Ala Ser Gln Gln Ile Leu Phe Gln Ala Tyr Glu Arg Gln Lys Asn Pro
    210                 215                 220
```

```
Ser Lys Glu Glu Arg Glu Thr Leu Val Glu Glu Cys Asn Arg Ala Glu
225                 230                 235                 240

Cys Ile Gln Arg Gly Val Ser Pro Ser Gln Ala Gln Gly Leu Gly Ser
            245                 250                 255

Asn Leu Val Thr Glu Val Arg Val Tyr Asn Trp Phe Ala Asn Arg Arg
        260                 265                 270

Lys Glu Glu Ala Phe Arg His Lys Leu Ala Met Asp Thr Tyr Ser Gly
    275                 280                 285

Pro Pro Pro Gly Pro Gly Pro Gly Pro Ala Leu Pro Ala His Ser Ser
290                 295                 300

Pro Gly Leu Pro Pro Pro Ala Leu Ser Pro Ser Lys Val His Gly Val
305                 310                 315                 320

Arg Tyr Gly Gln Pro Ala Thr Ser Glu Thr Ala Glu Val Pro Ser Ser
            325                 330                 335

Ser Gly Gly Pro Leu Val Thr Val Ser Thr Pro Leu His Gln Val Ser
        340                 345                 350

Pro Thr Gly Leu Glu Pro Ser His Ser Leu Leu Ser Thr Glu Ala Lys
    355                 360                 365

Leu Val Ser Ala Ala Gly Gly Pro Leu Pro Pro Val Ser Thr Leu Thr
370                 375                 380

Ala Leu His Ser Leu Glu Gln Thr Ser Pro Gly Leu Asn Gln Gln Pro
385                 390                 395                 400

Gln Asn Leu Ile Met Ala Ser Leu Pro Gly Val Met Thr Ile Gly Pro
            405                 410                 415

Gly Glu Pro Ala Ser Leu Gly Pro Thr Phe Thr Asn Thr Gly Ala Ser
        420                 425                 430

Thr Leu Val Ile Gly Leu Ala Ser Thr Gln Ala Gln Ser Val Pro Val
    435                 440                 445

Ile Asn Ser Met Gly Ser Ser Leu Thr Thr Leu Gln Pro Val Gln Phe
450                 455                 460

Ser Gln Pro Leu His Pro Ser Tyr Gln Gln Pro Leu Met Pro Pro Val
465                 470                 475                 480

Gln Ser His Val Thr Gln Ser Pro Phe Met Ala Thr Met Ala Gln Leu
            485                 490                 495

Gln Ser Pro His Ala Leu Tyr Ser His Lys Pro Glu Val Ala Gln Tyr
        500                 505                 510

Thr His Thr Gly Leu Leu Pro Gln Thr Met Leu Ile Thr Asp Thr Thr
    515                 520                 525

Asn Leu Ser Ala Leu Ala Ser Leu Thr Pro Thr Lys Gln Val Phe Thr
530                 535                 540

Ser Asp Thr Glu Ala Ser Ser Glu Ser Gly Leu His Thr Pro Ala Ser
545                 550                 555                 560

Gln Ala Thr Thr Leu His Val Pro Ser Gln Asp Pro Ala Gly Ile Gln
            565                 570                 575

His Leu Gln Pro Ala His Arg Leu Ser Ala Ser Pro Thr Val Ser Ser
        580                 585                 590

Ser Ser Leu Val Leu Tyr Gln Ser Ser Asp Ser Ser Asn Gly Gln Ser
    595                 600                 605

His Leu Leu Pro Ser Asn His Ser Val Ile Glu Thr Phe Ile Ser Thr
610                 615                 620

Gln Met Ala Ser Ser Ser Gln Leu
625                 630
```

METHOD FOR REDUCING DIFFERENTIATION RESISTANCE OF PLURIPOTENT STEM CELLS

TECHNICAL FIELD

The present disclosure relates to a method of attenuating differentiation resistance of a pluripotent stem cell to a desired cell type, and more specifically, to a method of differentiating a pluripotent stem cell into a desired cell type with high efficiency and a differentiation inducer to be used for the differentiation method.

The present application is a National Stage Application of PCT/JP2016/082152, filed Oct. 28, 2016, which claims priority from Japanese Patent Application No. 2015-211356, which is incorporated herein by reference.

BACKGROUND ART (On Induction of Differentiation of Pluripotent Stem Cells)

Regenerative medicine using cells obtained by inducing differentiation of embryonic stem cells (ES cells) or induced pluripotent stem cells (iPS cells) is a therapeutic method for which the people have high expectations and which is desired to be realized soon. As regenerative medicine, a transplantation therapy with retinal pigment epithelial cells derived from iPS cells is fresh in memory. However, a technology for generating mature differentiated cells suited for cell transplantation rapidly and in a sufficient amount is still under development and has huge room for development.

A currently mainstream method of inducing differentiation of pluripotent stem cells into a desired cell type is a method involving sequentially adding cytokines/growth factors suited for respective differentiation stages to a medium to cause differentiation via an embryoid body and progenitor cells. This method has problems in, for example, that a culture period until differentiated cells of interest are obtained is long, that differentiation induction efficiency is not high, and that cells of different cell lineages are mixed with each other.

In recent years, attempts have been actively made to direct cell differentiation by forcibly expressing, in ES/iPS cells, one or a combination of a plurality of tissue-specifically expressed transcription factors. This differentiation induction method using transcription factors can directly induce ES/iPS cells into differentiated cells of interest, and hence is expected to be very effective means. However, even with this technique, cell differentiation induction efficiency is low. Accordingly, under the circumstances, it is difficult to obtain a sufficient amount of differentiated cells of interest required for regenerative medicine depending on the kind of cells.

In view of the foregoing, there has been a demand for development of a novel differentiation induction method for producing differentiated cells of interest from pluripotent stem cells more rapidly and more uniformly with higher efficiency.

(Current Situation of Induction of Differentiation of Pluripotent Stem Cells in Related Prior Art)

Non Patent Literatures 1 to 4, which are related art, are each directed to a system for facilitating induction of differentiation of ES/iPS cells. As an example, there is a disclosure that ES/iPS cells are induced into skeletal muscle differentiation.

CITATION LIST

Non Patent Literature

[NPL 1] Nature medicine 13: 642-648.
[NPL 2] Cell stem cell 10: 610-619.
[NPL 3] Mol Ther. November; 20(11): 2153-67.
[NPL 4] PLoS One. 2013 Apr. 23; 8(4): e61540.

SUMMARY OF INVENTION

Problem to be Solved by Invention

In related-art methods of differentiating pluripotent stem cells into a desired cell type, there has not been established a differentiation induction method using human ES/iPS cells and being stable and highly efficient. Many attempts have been made, including a stepwise differentiation induction method based on the control of culture conditions or the addition of, for example, various cell growth factors/differentiation factors to a culture solution, but the use of complicated culture steps is a serious problem. In addition, there are also serious problems in, for example, that the speed of cell differentiation is low, and hence long-period culture is required, and that the differentiation efficiency is low, and hence it is difficult to obtain a sufficient number of required cells.

Means for Solving Problem

The inventors of the present invention have considered that the above-mentioned problems are partly due to the fact that pluripotent stem cells have a property of resisting cell differentiation by various mechanisms (stemness-maintaining property). In view of this, the inventors have found a method of inducing differentiation into a desired cell type within a short period of time and with high efficiency by attenuating differentiation resistance of a pluripotent stem cell to generate a pluripotent stem cell that actively proceeds to a differentiated cell type. Thus, the inventors have completed the present invention.

That is, the present disclosure includes the following.

1. A differentiation induction kit for differentiating a pluripotent stem cell into a desired cell type, including at least any one of the following items (1) to (5):
   (1) a pluripotent stem cell having a histone in which H3K27me3 modification has been substantially removed or reduced;
   (2) a pluripotent stem cell in which a demethylase is forcibly expressed;
   (3) a pluripotent stem cell and a demethylase gene;
   (4) a gene construct carrying a demethylase gene and a pluripotent stem cell; and
   (5) a pluripotent stem cell having a gene construct carrying a demethylase gene inserted into a genome thereof.
2. A differentiation induction kit according to the above-mentioned item 1, wherein the differentiation induction kit includes the above-mentioned item (1), (2), or (5).
3. A differentiation induction kit according to the above-mentioned item 1 or 2, wherein the demethylase is JMJD3.
4. A differentiation induction kit according to the above-mentioned item 1 or 2, wherein the demethylase is a demethylase containing only an enzymatically active region of JMJD3.
5. A differentiation induction kit according to the above-mentioned item 3, wherein the demethylase has an amino acid sequence set forth in any one of SEQ ID NOS: 1 to 3.

6. A differentiation induction kit according to any one of the above-mentioned items 1 to 5, further including a transcription factor required for induction of differentiation into the desired cell type.

7. A differentiation induction kit for differentiating a pluripotent stem cell into a skeletal muscle cell, including at least any one of the following items (1) to (5):

(1) a pluripotent stem cell having a histone in which H3K27me3 modification has been substantially removed or reduced, and a transcription factor MYOD1;

(2) a pluripotent stem cell in which a demethylase is forcibly expressed, and a transcription factor MYOD1;

(3) a pluripotent stem cell, a demethylase gene, and a transcription factor MYOD1;

(4) a gene construct carrying a demethylase gene, a pluripotent stem cell, and a transcription factor MYOD1; and (5) a pluripotent stem cell having a gene construct carrying a demethylase gene inserted into a genome thereof, and a transcription factor MYOD1.

8. A differentiation induction kit for differentiating a pluripotent stem cell into a nerve cell, including at least any one of the following items (1) to (5):

(1) a pluripotent stem cell having a histone in which H3K27me3 modification has been substantially removed or reduced, and transcription factors NEUROG1, NEUROG2, NEUROG3, NEUROD1, and NEUROD2;

(2) a pluripotent stem cell in which a demethylase is forcibly expressed, and transcription factors NEUROG1, NEUROG2, NEUROG3, NEUROD1, and NEUROD2;

(3) a pluripotent stem cell, a demethylase gene, and transcription factors NEUROG1, NEUROG2, NEUROG3, NEUROD1, and NEUROD2;

(4) a gene construct carrying a demethylase gene, a pluripotent stem cell, and transcription factors NEUROG1, NEUROG2, NEUROG3, NEUROD1, and NEUROD2; and (5) a pluripotent stem cell having a gene construct carrying a demethylase gene inserted into a genome thereof, and transcription factors NEUROG1, NEUROG2, NEUROG3, NEUROD1, and NEUROD2.

9. A differentiation induction kit for differentiating a pluripotent stem cell into a liver cell, including at least any one of the following items (1) to (5):

(1) a pluripotent stem cell having a histone in which H3K27me3 modification has been substantially removed or reduced, and a transcription factor HNF1A;

(2) a pluripotent stem cell in which a demethylase is forcibly expressed, and a transcription factor HNF1A;

(3) a pluripotent stem cell, a demethylase gene, and a transcription factor HNF1A;

(4) a gene construct carrying a demethylase gene, a pluripotent stem cell, and a transcription factor HNF1A; and (5) a pluripotent stem cell having a gene construct carrying a demethylase gene inserted into a genome thereof, and a transcription factor HNF1A.

10. A method of differentiating a pluripotent stem cell into a desired cell type, including any one of the following steps (1) to (7):

(1) a step of adding a demethylase gene and a transcription factor required for induction of differentiation into the desired cell type to a pluripotent stem cell;

(2) a step of inserting a gene construct carrying a demethylase gene and a transcription factor gene required for induction of differentiation into the desired cell type into a genome of a pluripotent stem cell;

(3) a step of inserting a gene construct carrying a demethylase gene into a genome of a pluripotent stem cell, followed by addition of a transcription factor required for induction of differentiation into the desired cell type to the cell;

(4) a step of inserting a gene construct carrying a demethylase gene and a gene construct carrying a transcription factor required for induction of differentiation into the desired cell type into a genome of a pluripotent stem cell;

(5) a step of adding a transcription factor required for induction of differentiation into the desired cell type to a pluripotent stem cell having a histone in which H3K27me3 modification has been substantially removed or reduced;

(6) a step of adding a transcription factor required for induction of differentiation into the desired cell type to a pluripotent stem cell in which a demethylase is forcibly expressed; and (7) a step of adding a demethylase and a transcription factor required for differentiation into the desired cell type to a pluripotent stem cell.

11. A method of differentiating a pluripotent stem cell according to the above-mentioned item 10, wherein the differentiation induction kit includes the above-mentioned step (1), (3), (6), or (7).

12. A method of differentiating a pluripotent stem cell according to the above-mentioned item 10 or 11, wherein the demethylase is JMJD3.

13. A method of differentiating a pluripotent stem cell according to the above-mentioned item 10 or 11, wherein the demethylase is a demethylase containing only an enzymatically active region of JMJD3.

14. A method of differentiating a pluripotent stem cell into a skeletal muscle cell, including any one of the following steps (1) to (7):

(1) a step of adding a demethylase gene and a transcription factor MYOD1 to a pluripotent stem cell;

(2) a step of inserting a gene construct carrying a demethylase gene and a desired transcription factor MYOD1 gene into a genome of a pluripotent stem cell;

(3) a step of inserting a gene construct carrying a demethylase gene into a genome of a pluripotent stem cell, followed by addition of a transcription factor MYOD1 to the cell;

(4) a step of inserting a gene construct carrying a demethylase gene and a gene construct carrying a transcription factor MYOD1 into a genome of a pluripotent stem cell;

(5) a step of adding a transcription factor MYOD1 to a pluripotent stem cell having a histone in which H3K27me3 modification has been substantially removed or reduced;

(6) a step of adding a transcription factor MYOD1 to a pluripotent stem cell in which a demethylase is forcibly expressed; and (7) a step of adding a demethylase and a transcription factor MYOD1 to a pluripotent stem cell.

15. A method of differentiating a pluripotent stem cell into a nerve cell, including any one of the following steps (1) to (7):

(1) a step of adding a demethylase gene and a transcription factor NEUROG1, NEUROG2, NEUROG3, NEUROD1, and/or NEUROD2 to a pluripotent stem cell;

(2) a step of inserting a gene construct carrying a demethylase gene and a desired transcription factor NEUROG1, NEUROG2, NEUROG3, NEUROD1, and/or NEUROD2 gene into a genome of a pluripotent stem cell;

(3) a step of inserting a gene construct carrying a demethylase gene into a genome of a pluripotent stem cell, followed by addition of a transcription factor NEUROG1, NEUROG2, NEUROG3, NEUROD1, and/or NEUROD2 to the cell;

(4) a step of inserting a gene construct carrying a demethylase gene and a gene construct carrying a transcription factor NEUROG1, NEUROG2, NEUROG3, NEUROD1, and/or NEUROD2 into a genome of a pluripotent stem cell;

(5) a step of adding a transcription factor NEUROG1, NEUROG2, NEUROG3, NEUROD1, and/or NEUROD2 to a pluripotent stem cell having a histone in which H3K27me3 modification has been substantially removed or reduced;

(6) a step of adding a transcription factor NEUROG1, NEUROG2, NEUROG3, NEUROD1, and/or NEUROD2 to a pluripotent stem cell in which a demethylase is forcibly expressed; and (7) a step of adding a demethylase and a transcription factor NEUROG1, NEUROG2, NEUROG3, NEUROD1, and/or NEUROD2 to a pluripotent stem cell.

16. A method of differentiating a pluripotent stem cell into a liver cell, including any one of the following steps (1) to (7):

(1) a step of adding a demethylase gene and a transcription factor HNF1A to a pluripotent stem cell;

(2) a step of inserting a gene construct carrying a demethylase gene and a desired transcription factor HNF1A gene into a genome of a pluripotent stem cell;

(3) a step of inserting a gene construct carrying a demethylase gene into a genome of a pluripotent stem cell, followed by addition of a transcription factor HNF1A to the cell;

(4) a step of inserting a gene construct carrying a demethylase gene and a gene construct carrying a transcription factor HNF1A into a genome of a pluripotent stem cell;

(5) a step of adding a transcription factor HNF1A to a pluripotent stem cell having a histone in which H3K27me3 modification has been substantially removed or reduced;

(6) a step of adding a transcription factor HNF1A to a pluripotent stem cell in which a demethylase is forcibly expressed; and (7) a step of adding a demethylase and a transcription factor HNF1A to a pluripotent stem cell.

17. A method of differentiating a pluripotent stem cell according to any one of the above-mentioned items 10 to 13, wherein the transcription factor required for induction of differentiation into the desired cell type is TCF-1, and the desired cell type is a hepatoblast.

18. A method of differentiating a pluripotent stem cell according to any one of the above-mentioned items 10 to 13, wherein the transcription factor required for induction of differentiation into the desired cell type is SOX9, and the desired cell type is a chondrocyte.

19. A method of differentiating a pluripotent stem cell according to any one of the above-mentioned items 10 to 13, wherein the transcription factor required for induction of differentiation into the desired cell type is RUNX3, and the desired cell type is an osteoblast.

Advantageous Effects of Invention

The method of differentiating a pluripotent stem cell into a desired cell type with high efficiency and differentiation induction kit for differentiating a pluripotent stem cell into a desired cell type with high efficiency of the present disclosure have at least any one of the following effects.

(1) The period of time required for cell differentiation starting with the pluripotent stem cell is shortened and/or the differentiation induction efficiency is improved.

(2) As modified synthetic mRNA for a gene is used to introduce the gene into the pluripotent stem cell, the introduced gene is not integrated into the genome of the pluripotent stem cell, with the result that there is no risk of canceration or the like after cell differentiation induction.

(3) In the introduction of the gene into the pluripotent stem cell using the modified synthetic mRNA, the timing and number of times of the addition of the mRNA for the gene can be easily changed, and hence optimal conditions specific to each of various desired cell types can be selected so as to differentiate the pluripotent stem cell into the desired cell types.

BRIEF DESCRIPTION OF DRAWINGS

FIG. 5A: The structures of full-length JMJD3 (JMJD3f) and JMJD3c proteins. JMJD3c was designed to contain the JmjC domain (amino acids 1376 to 1484) having demethylase activity. FIG. 5B: hESCs were transfected with modified synthetic mRNA for human influenza virus hemagglutinin (HA)-tagged full-length JMJD3 (HA-JMJD3f) or HA-tagged JMJD3c (HA-JMJD3c), and were stained with an anti-HA antibody and an anti-H3K27me3 antibody. The arrowheads indicate the transfected cells. FIG. 5C: The effects of transfection of the HA-JMJD3f and HA-JMJD3c mRNAs on H3K27me3 were analyzed by an immunoblotting method. Modified synthetic mRNA for a green fluorescent protein Emerald (Em) was transfected as a control. An anti-H3 antibody was used as a loading control. FIG. 5D: A plasmid vector for tet-on induction of JMJD3c in hESCs (JMJD3c-hESCs). FIG. 5E: JMJD3c-hESCs were stained with 5-bromo-4-chloro-3-indolyl-β-D-galactopyranoside (X-gal) 3 days after doxycycline (Dox) treatment. FIG. 5F: HA-JMJD3c-induced H3K27me3 demethylation was detected 1 day to 3 days after DOX treatment. FIG. 5G: A point mutation in a JMJD3c mutant (mut) was introduced at amino acid 1390 for demethylase inactivation. FIG. 5H: Confirmation of the influences of HA-JMJD3c and HA-JMJD3c mut on H3K27me3.

FIG. 6A: Morphologies of JMJD3-hESCs without Dox treatment (−JMJD3c) and with Dox treatment (+JMJD3c). FIG. 6B: Changes in H3K27me3 and H3K4me3 after Dox treatment (Day 0 to Day 3) were analyzed by ChIP-qPCR. POU5F1 and NANOG are stem cell genes, and T, MX1, SOX17, FOXA2, GATA4, GATA6, GSC, and EVX1 are mesendodermal differentiation-related genes. n=2 or 3.

*P<0.05. The error bars indicate the standard error of the mean (SEM). FIG. 6C: qRT-PCR analyses for showing relative expression of stem cell genes and mesendodermal differentiation-related genes under differentiation conditions as compared with hESCs. Basal Medium represents a medium without cytokines and growth factors, activin A represents a medium for endodermal differentiation, activin A+BMP4+bFGF represents a medium for mesodermal differentiation, and JMJD3c represents a medium with Dox (forced expression of JMJD3c). The expression levels were normalized to the expression amount of glyceraldehyde 3-phosphate dehydrogenase (GAPDH).

FIG. 7A: A schematic of a differentiation protocol. JMJD3c-hESCs were treated with or without Dox on from Day 1 to Day 2 after plating and were transfected with synthetic mRNA for MYOD1 or Emerald three times on from Day 2 to Day 3. The cells were collected on Day 5. FIG. 7B: RT-qPCR analyses of muscle differentiation-related genes in MYOD1-differentiated cells with Dox treatment (+JMJD3c) or without Dox treatment (-JMJD3c). - represents no transfection, Em represents Emerald transfection, and MYOD1 represents MYOD1 transfection. The expression levels were normalized to GAPDH. n=3. The error bars indicate the SEM. FIG. 7C: ChIP-qPCR analyses of H3K27me3, H3K4me3, and H3K27ac in the promoter regions of MYOG and MEF2C genes of MYOD1-transfected cells with Dox treatment (+JMJD3c) or without Dox treatment (-JMJD3c). For the promoter regions of the MYOG and MEF2C genes, two regions (FIGS. 7A to 7C) and three regions (FIG. 7A, 7B) were tested, respectively. GAPDH, POU5F1, and T each represent a positive control, and SOX1 represents a negative control. n=2 or 3. P<0.05. The error bars indicate the SEM. FIG. 7D: Immunostaining for myosin heavy chain isoform (MHC) in the cells in which JMJD3c, MYOD1, or JMJD3c+MYOD1 are forcibly expressed. FIG. 7E: The percentage of nuclei contained within MHC-stained cells. n=3. *P<0.01. The error bars indicate SEM. FIG. 7F: Immunostaining for MHC in the MYOD1-transfected cells in which JMJD3c or the JMJD3c mutant is forcibly expressed. FIG. 7G: The percentage of nuclei contained within MHC-stained cells. n=3. *P<0.01. The error bars indicate the SEM.

FIGS. 8A-8G: Differentiation of hESCs and iPSCs into skeletal muscle cells by transfection of a demethylase and a transcription factor as synthetic mRNAs. FIG. 8A: A schematic of a differentiation induction protocol. hESC/iPSCs were transfected with synthetic mRNAs for JMJD3c or a red fluorescent protein mCherry twice on Day 1 and Day 2 and MYOD1 three times on Day 2 and Day 3. The cells were fixed for immunostaining on Day 5. FIG. 8B: Immunostaining for MHC in cells that were transfected with MYOD1 after mCherry or JMJD3c transfection. FIG. 8C: The percentage of nuclei contained within MHC-stained cells. n=3. *P<0.01. The error bars indicate the SEM. FIG. 8D: Representative staining images for showing muscular fusion (arrowheads). FIG. 8E: Induced myogenic cells were labeled with green fluorescence and cocultured with mouse C2C12 cells having nuclei labeled with red fluorescence. On Day 3 and Day 5 after cocultuing, cell fusions were detected (arrowheads). FIG. 8F: iPSCs were transfected with mCherry or JMJD3c, followed by MYOD1, and were immunostained for MHC. FIG. 8G: The percentage of nuclei contained within MHC-stained cells. n=3. *P<0.01. The error bars indicate the SEM.

FIG. 9: Increases in expression of marker genes for hepatoblasts (TCF-1), chondrocytes (SOX9), and osteoblasts (RUNX3) through expression of respective transcription factors TCF-1, SOX9, and RUNX3 in combination with JMJD3c. AFP is a marker gene for hepatoblasts, COL2 is a marker gene for chondrocytes, and COL1A1 is a marker gene for osteoblasts. The expression levels were standardized to GAPDH. n=2. *P<0.05. The error bars indicate the SEM.

DESCRIPTION OF EMBODIMENTS

Figure 1A:
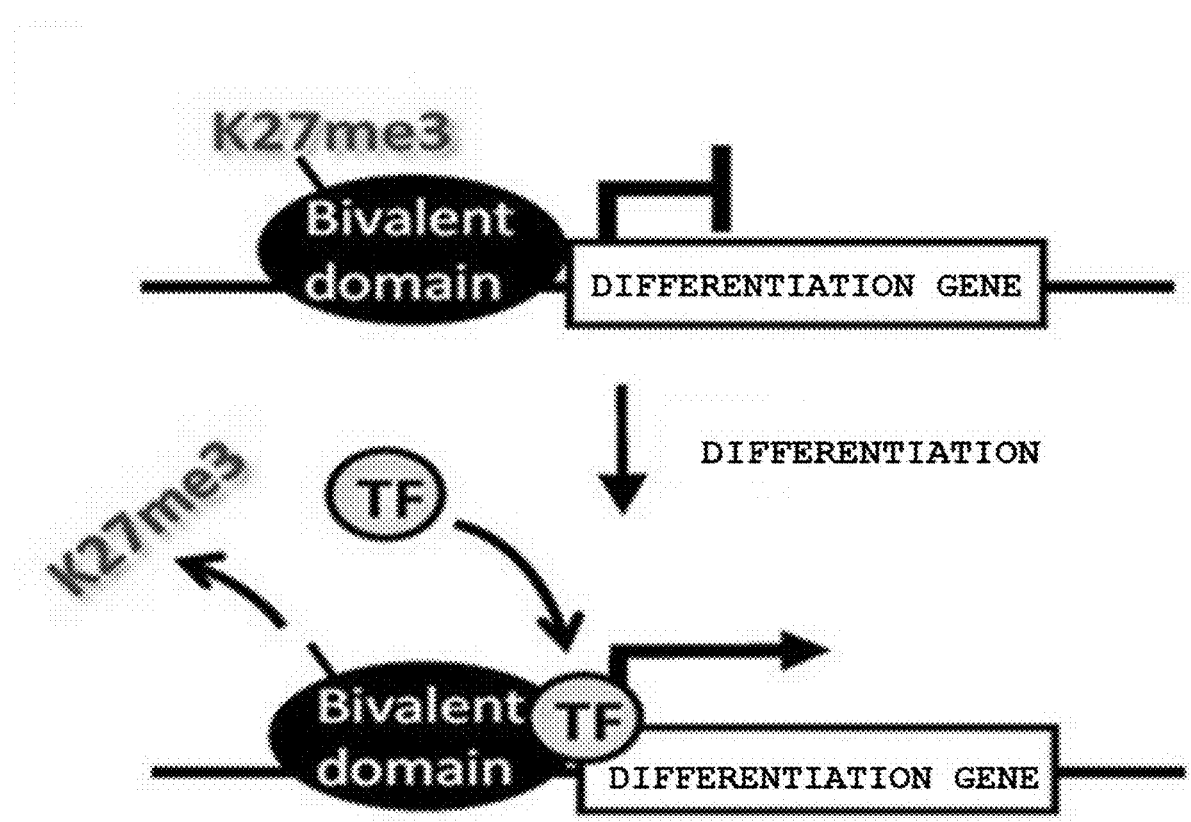
FIG. 1A: A schematic diagram of a method of attenuating differentiation resistance of a pluripotent stem cell to a desired cell type of the present disclosure.
Figure 1B:
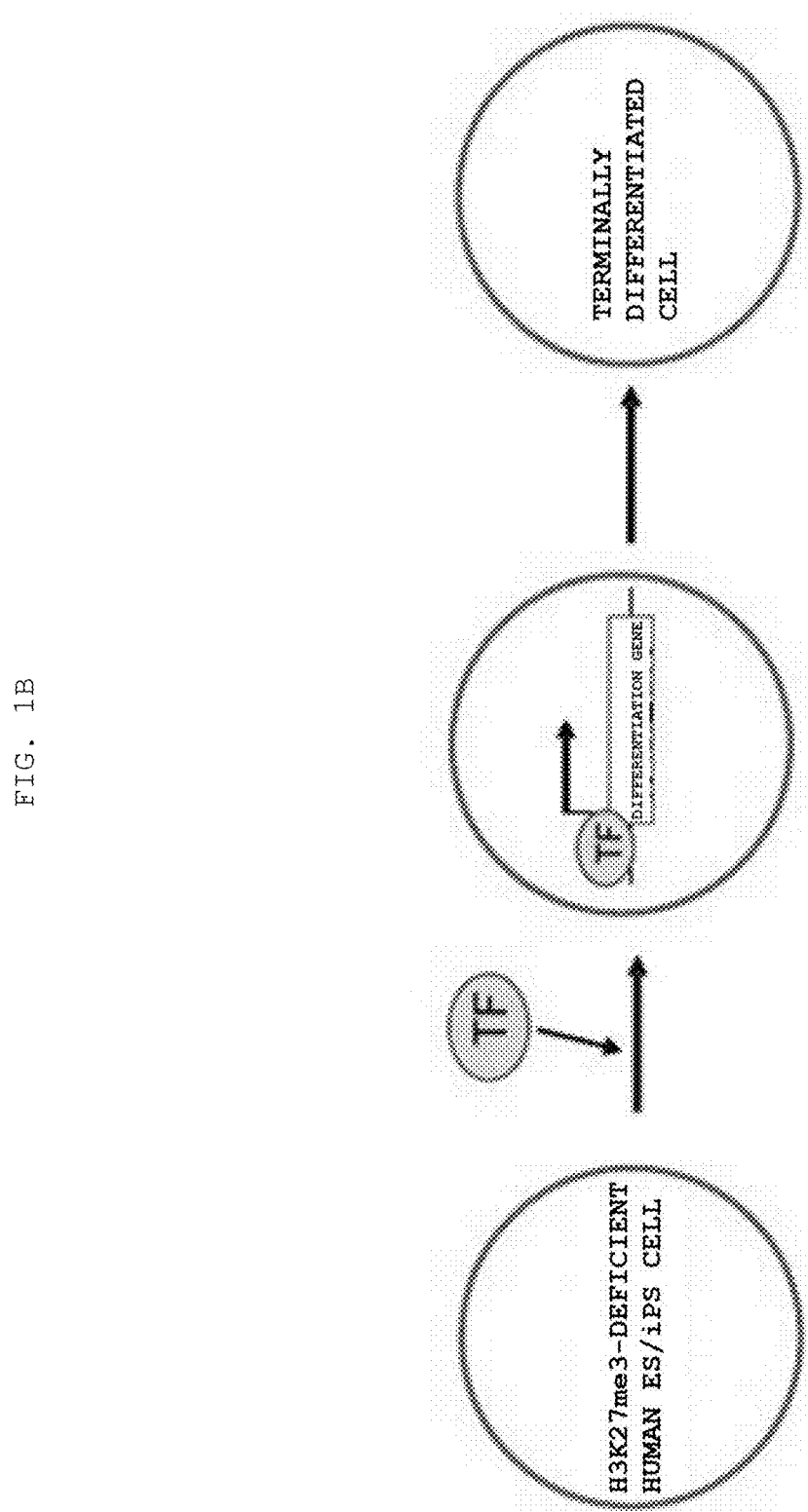
FIG. 1B: When H3K27me3 in a human ES or iPS cell is attenuated or removed, a transcription factor (TF) binds to the promoter site of a downstream gene to enhance the expression of a group of development/differentiation-related genes, resulting in differentiation.
Figure 1C:
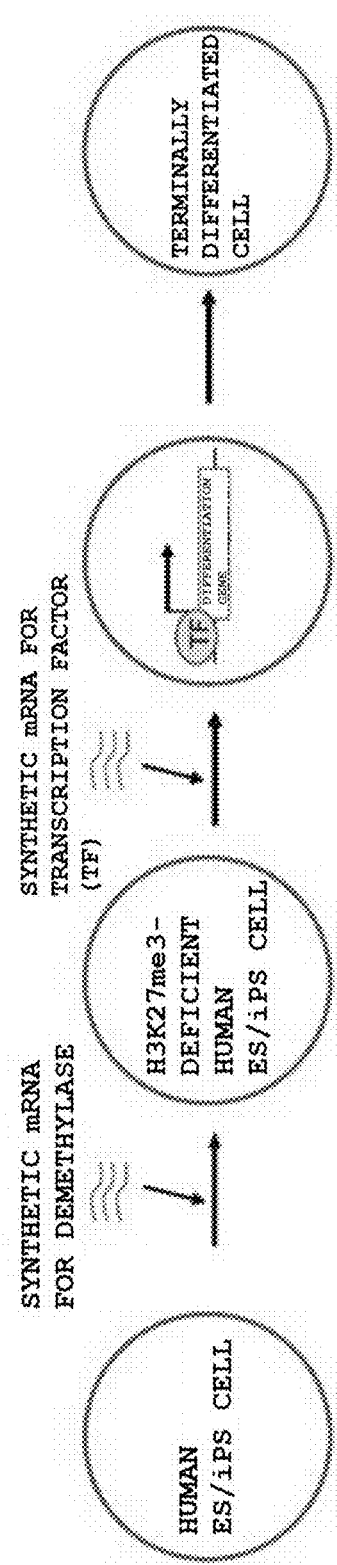
FIG. 1C: A method of inducing differentiation of a human ES cell or an iPS cell by introducing modified synthetic mRNA for a demethylase, and then introducing modified synthetic mRNA for the transcription factor (TF).
Figure 1D:
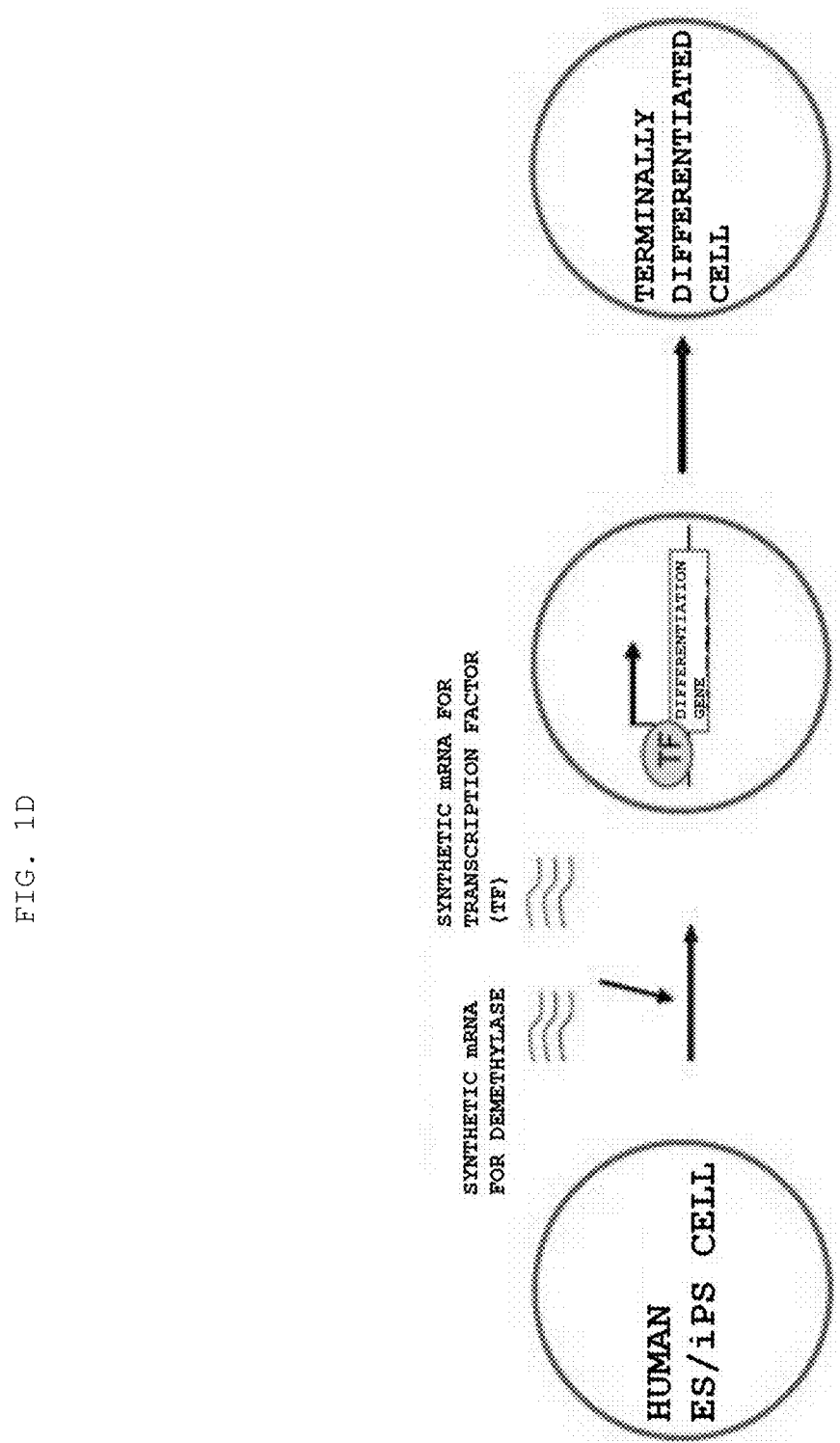
FIG. 1D: A method of inducing differentiation of a human ES cell or an iPS cell by simultaneously introducing the modified synthetic mRNAs for the demethylase and the transcription factor (TF).

A method of inducing differentiation of a pluripotent stem cell into a desired cell type with high efficiency of the present disclosure (hereinafter sometimes referred to as "method of the present disclosure") is described below, though the method is not particularly limited as long as the method can attenuate differentiation resistance of a pluripotent stem cell to the desired cell type.

(Pluripotent Stem Cell)

The pluripotent stem cell to be used in the method of the present disclosure is not particularly limited, but is preferably derived from a mammal, more preferably derived from a human. The pluripotent stem cell is, for example, a human ES cell, a human iPS cell, or any combination thereof, is not particularly limited, and encompasses tissue stem cells derived from tissues and organs, dermal fibroblasts, and all kinds of cells derived from tissues or organs.

(Attenuating Differentiation Resistance of Pluripotent Stem Cell to Desired Cell Type)

In pluripotent stem cells, a special chromatin structure called a "bivalent domain" is formed in each promoter region of a group of genes involved in differentiation, and under a stemness-maintaining state, the group of genes involved in development/differentiation are in a standby state so as not to be easily expressed. In Examples of the present disclosure, it has been confirmed that "when a methyl group modification of a histone called H3K27me3 is removed or reduced in the "bivalent domain", the expression of differentiation genes required for induction of differentiation into the desired cell type is rapidly and efficiently facilitated" (see FIGS. 1A-1D).

That is, the "attenuating differentiation resistance of a pluripotent stem cell to a desired cell type" of the present disclosure means that the H3K27me3 modification of the pluripotent stem cell is substantially removed or reduced.

In addition, a state in which the H3K27me3 modification of the pluripotent stem cell has been substantially removed or reduced may be confirmed by a comparison to the degree of the H3K27me3 modification of a pluripotent stem cell that has not been subjected to the removing or the reducing. For example, the state (degree) in which the H3K27me3 modification of the pluripotent stem cell has been substantially removed or reduced is from 95 to 1, from 90 to 2, from 85 to 3, from 80 to 4, from 75 to 5, from 70 to 6, from 65 to 7, from 60 to 8, from 50 to 10, from 40 to 20, about 30, or 50 or less, 40 or less, 30 or less, 20 or less, or 10 or less when compared to the degree of the H3K27me3 modification of the pluripotent stem cell that has not been removed or reduced, which is defined as 100. The degree of the H3K27me3 modification of the pluripotent stem cell may be easily measured by using a commercially available anti-Histone H3K27me3 antibody, and the gene expression amount of H3K27me3 may be measured by a method known per se.

(Method of Inducing Differentiation of Pluripotent Stem Cell into Desired Cell Type with High Efficiency of the Present Disclosure)

As described above, the method of the present disclosure is not particularly limited as long as the method can attenuate differentiation resistance of the pluripotent stem cell to the desired cell type, and may be exemplified by the following.

(Use of Modified Synthetic mRNA for Target Gene)

The method of the present disclosure includes adding (introducing, transfecting), to a pluripotent stem cell, a gene for a compound having an action of substantially removing or reducing H3K27me3 modification, and a gene for a transcription factor required for induction of differentiation of the pluripotent stem cell into the desired cell type.

The term "gene" as used herein encompasses not only double strands, but also their respective constituent single strands, such as plus strands (or sense strands) or complementary strands (or antisense strands), linear nucleic acids, and circular nucleic acids, and encompasses DNA, RNA, mRNA, cDNA, and the like, unless otherwise stated.

In addition, the term "target gene" is meant to encompass both or any one of the gene for the compound having an action of substantially removing or reducing H3K27me3 modification and the transcription factor required for induction of differentiation into the desired cell type.

Figure 2:
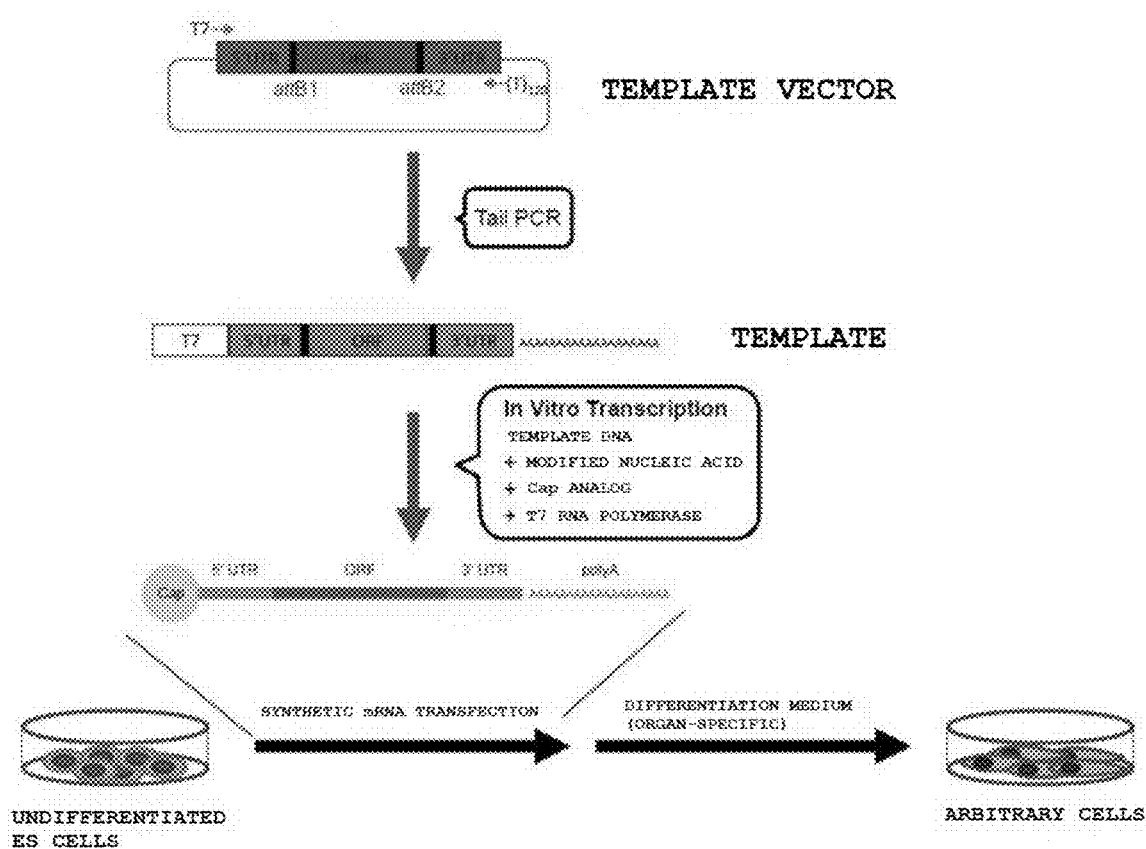
FIG. 2: A schematic view of a differentiation induction method using modified synthetic mRNA for a target gene.

In a step of the method of the present disclosure, a method known per se may be used without any particular limitation as a method of adding (introducing, transfecting) the gene for the compound having an action of substantially removing or reducing H3K27me3 modification and/or the transcription factor required for induction of differentiation into the desired cell type to the pluripotent stem cell. There is preferably used a method of inducing differentiation by efficiently introducing synthetic mRNA for a transcription factor into human pluripotent stem cells through use of a gene expression method involving using synthetic mRNA developed by Warren, Rossi, et al. (reference: Cell Stem Cell 7: 618-630, 2010), which is a footprint-free forced gene expression method causing no gene integration into a host genome (see FIG. 2).

The timing at which the gene for the compound having an action of substantially removing or reducing H3K27me3 modification and the transcription factor required for induction of differentiation into the desired cell type are added to the pluripotent stem cell is not particularly limited, but it is preferred that the gene for the compound having an action of substantially removing or reducing H3K27me3 modification be added to the pluripotent stem cell before the addition of the transcription factor required for differentiation induction.

Further, with regard to the addition timing of each gene (mRNA), the addition may be performed, for example, one or more times, preferably two to five times, two to four times, two or three times, or two times every 12 hours to 64 hours, but the addition timing is not particularly limited thereto.

A more specific method may be exemplified by the following.

(Synthesis of Modified mRNA Encoding Amino Acid Sequence of Transcription Factor)

Modified mRNA is synthesized with reference to a method described in the literature "Warren et al., Cell Stem Cell, 2010 Nov. 5; 7 (5): 618-30." More detailed, mRNA is synthesized by in vitro transcription using a mixture of dNTPs {(dNTPs: 3-O-Me-m7G(5')ppp(5')GARCA cap analog, 5-methylcytidine triphosphate, and pseudouridine triphosphate)} obtained by modifying template DNA encoding the amino acid sequence of the transcription factor required for induction of differentiation into the desired cell type.

(Generation of Sendai Virus Vector Encoding Amino Acid Sequence of Transcription Factor)

In order to express a mammalian (in particular, human) transcription factor, a Sendai virus vector capable of expressing a human transcription factor is preferably used. In particular, a mutant of a Sendai virus vector, such as an F protein-deficient mutant, has no infectivity, and is easy to handle (see Inoue et al., J Virol. 77: 23238-3246, 2003).

(Method of Inducing Differentiation of Pluripotent Stem Cell into Desired Cell Type with High Efficiency)

A single transcription factor or a cocktail of two or more transcription factors required for induction of differentiation into the desired cell type is prepared. The form of the transcription factors is not particularly limited, and may be any of synthetic mRNAs, a Sendai virus vector having incorporated therein a transcription factor (or a plurality of transcription factors), and nanoparticle capsules containing synthetic mRNAs.

Figure 3:
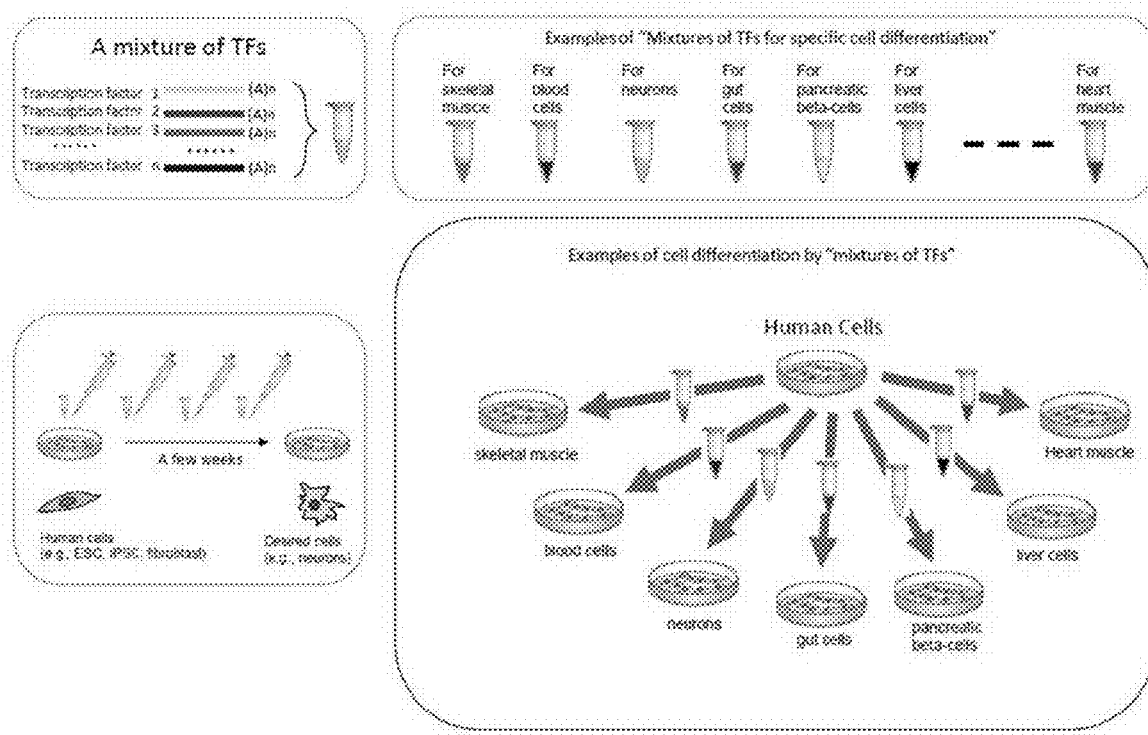
FIG. 3: A schematic view of a differentiation step using modified synthetic mRNA for a target gene.

A method of introducing the single transcription factor or cocktail of two or more transcription factors described above into cells is not particularly limited, and transfection with Lipofectamine, viral infection, or the like is utilized. A schematic view of the differentiation induction step of the method of the present disclosure is illustrated in FIG. 3.

(Use of Expression Vector)

In a step of the method of the present disclosure, an expression vector known per se having introduced therein the gene for the compound having an action of substantially removing or reducing H3K27me3 modification and/or the transcription factor required for induction of differentiation into the desired cell type may be used. Examples of the expression vector to be used in the present disclosure may include, but not particularly limited to, an animal cell expression plasmid vector and a Sendai virus vector.

A method of introducing the synthetic mRNA and the expression vector into the pluripotent stem cell is not particularly limited, for examples thereof may include a lipofection method, a liposome method, an electroporation method, a calcium phosphate coprecipitation method, a diethylaminoethyl (DEAE)-dextran method, a microinjection method, and a gene gun method. A particularly preferred example is a lipofection method.

Another method may involve using an expression vector for the gene for the compound having an action of substantially removing or reducing H3K27me3 modification, and using synthetic mRNA for the transcription factor required for induction of differentiation into the desired cell type, or may adopt the opposite pattern.

(Compound Having Action of Substantially Removing or Reducing H3K27Me3 Modification)

The compound having an action of substantially removing or reducing H3K27me3 modification of the present disclosure is not particularly limited, and is, for example, a demethylase (in particular, a demethylase having an action of removing a methyl group of H3K27me3), an antibody that specifically binds to H3K27me3, an antibody for a Polycomb-group proteins (PcG proteins) having an H3K27me3 modification action, small interfering RNA (siRNA), or an inhibitor.

In addition, not only by using those compounds alone, but also by using a plurality of kinds of compounds and/or a low-molecular-weight compound in combination, it is possible to efficiently "attenuate differentiation resistance of a pluripotent stem cell to a desired cell type (substantially remove or reduce H3K27me3 modification of a pluripotent stem cell)."

Examples of the low-molecular-weight compound may include, but not particularly limited to, histone deaceylase (HDAC) inhibitors, such as valproic acid.

Examples of the demethylase include AOF (LSD1), AOF1 (LSD2), FBXL11 (JHDM1A), Fbxl10 (JHDM1B), FBXL19 (JHDM1C), KIAA1718 (JHDM1D), PHF2 (JHDM1E), PHF8 (JHDM1F), JMJD1A(JHDM2A), JMJD1B(JHDM2B), JMJD1C (JHDM2C), JMJD2A (JHDM3A), JMJD2B (JHDM3B), JMJD2C (JHDM3C), JMJD2D (JHDM3D), RBP2 (JARID1A), PLU1 (JARID1B), SMCX (JARID1C), SMCY (JARID1D), Jumonji (JARID2), UTX (UTX), UTY (UTY), JMJD3 (JMJD3), JMJD4 (JMJD4), JMJD5 (JMJD5), JMJD6 (JMJD6), JMJD7 (JMJD7), and JMJD8 (JMJD8). Of those, JMJD3 or the like is preferred as a demethylase having an action of removing a methyl group of H3K27me3.

In addition, the demethylase of the present disclosure may also include the following:

(1) a protected derivative, sugar chain-modified product, acylated derivative, or acetylated derivative of any one of the demethylases described above;

(2) an enzyme that has 90% (or 92%, 94%, 96%, 98%, or 99%) or more homology to any one of the demethylases described above and has a substantially equivalent action of substantially removing or reducing H3K27me3 modification to that of the demethylase; and (3) an enzyme that has 100 to 10, 50 to 30, 40 to 20, 10 to 5, or 5 to 1 amino acid substituted, deleted, inserted, and/or added in any one of the demethylases described above and has a substantially equivalent action of substantially removing or reducing H3K27me3 modification to that of the demethylase.

Further, the gene of the demethylase of the present disclosure includes the following:

(1) a gene encoding a polypeptide formed of the amino acid sequence of any one or more of the enzymes described above;

(2) a gene encoding a polypeptide that has 1 to 20 (or 1 to 15, 1 to 10, 1 to 7, 1 to 5, or 1 to 3) amino acids substituted, deleted, inserted, and/or added in the amino acid sequence of any one or more of the enzymes described above and has a substantially equivalent action of substantially removing or reducing H3K27me3 modification to that of the demethylase; and (3) a gene encoding a polypeptide that has 90% (or 92%, 94%, 96%, 98%, or 99%) or more homology to the amino acid sequence of any one or more of the enzymes described above and has a substantially equivalent action of substantially removing or reducing H3K27me3 modification to that of the demethylase.

An enzyme having a mutation may be a naturally occurring one, or may be one obtained by introducing a mutation on the basis of a gene of natural origin. Means for introducing a mutation is known per se, and for example, a site-directed mutagenesis method, a homologous gene recombination method, a primer extension method, a polymerase chain reaction (hereinafter abbreviated as PCR), and the like may be used alone or in combination thereof as appropriate.

The method may be performed in conformity with any of methods described in the literatures ("Molecular Cloning: A Laboratory Manual, second edition" edited by Sambrook et al., 1989, Cold Spring Harbor Laboratory; and "Lab Manual: Genetic Engineering" edited by Masami Muramatsu, 1988, Maruzen), or by modifying these methods, and Ulmer's technology (Ulmer, K. M., "Science", 1983, volume 219, p. 666-671) may also be utilized. In the case of a peptide, from the viewpoint of preventing alteration of basic properties of the peptide (e.g., physical properties, function, physiological activity, or immunological activity) in the introduction of a mutation, for example, mutual substitution between homologous amino acids (e.g., polar amino acids, non-polar amino acids, hydrophobic amino acids, hydrophilic amino acids, positively charged amino acids, negatively charged amino acids, and aromatic amino acids) is easily conceivable.

(JMJD3)

JMJD3 is known as a demethylase for H3K27me3 of a histone (mouse NP_001017426, human NP_001073893), and even in its full length (NP_001073893, SEQ ID NO: 1), has an action of substantially removing or reducing the H3K27me3 modification of pluripotent stem cells. However, in Example 1 of the present disclosure, it has been confirmed that JMJD3c having the JmjC domain {SEQ ID NO: 2, catalytic domain: SEQ ID NO: 3 (amino acids 1376-1484)} has a stronger action of substantially removing or reducing H3K27me3 modification as compared to full-length JMJD3 (see Example 2).

In addition, the JMJD3 of the present disclosure encompasses the following embodiments as well:

(1) a protected derivative, sugar chain-modified product, acylated derivative, or acetylated derivative of an amino acid sequence set forth in SEQ ID NO: 1;

(2) an amino acid sequence that has 90% (or 92%, 94%, 96%, 98%, or 99%) or more homology to the amino acid sequence set forth in SEQ ID NO: 1 and has a substantially equivalent action of substantially removing or reducing H3K27me3 modification to that of the JMJD3;

(3) an amino acid sequence that has 100 to 10, 50 to 30, 40 to 20, 10 to 5, or 5 to 1 amino acid substituted, deleted, inserted, and/or added in the amino acid sequence set forth in SEQ ID NO: 1 and has a substantially equivalent action of substantially removing or reducing H3K27me3 modification to that of the JMJD3;

(4) a protected derivative, sugar chain-modified product, acylated derivative, or acetylated derivative of an amino acid sequence set forth in SEQ ID NO: 2;

(5) an amino acid sequence that has 90% (or 92%, 94%, 96%, 98%, or 99%) or more homology to the amino acid sequence set forth in SEQ ID NO: 2 and has a substantially equivalent action of substantially removing or reducing H3K27me3 modification to that of the JMJD3c;

(6) an amino acid sequence that has 100 to 10, 50 to 30, 40 to 20, 10 to 5, or 5 to 1 amino acid substituted, deleted, inserted, and/or added in the amino acid sequence set forth in SEQ ID NO: 2 and has a substantially equivalent action of substantially removing or reducing H3K27me3 modification to that of the JMJD3c;

(7) a protected derivative, sugar chain-modified product, acylated derivative, or acetylated derivative of an amino acid sequence set forth in SEQ ID NO: 3;

(8) an amino acid sequence that has 90% (or 92%, 94%, 96%, 98%, or 99%) or more homology to the amino acid sequence set forth in SEQ ID NO: 3 and has a substantially equivalent action of substantially removing or reducing H3K27me3 modification to that of the JMJD3;

(9) an amino acid sequence that has 100 to 10, 50 to 30, 40 to 20, 10 to 5, or 5 to 1 amino acid substituted, deleted, inserted, and/or added in the amino acid sequence set forth in SEQ ID NO: 3 and has a substantially equivalent action of substantially removing or reducing H3K27me3 modification to the JMJD3; and

(10) an amino acid sequence that includes the amino acid sequence set forth in SEQ ID NO: 3 and has a substantially equivalent action of substantially removing or reducing H3K27me3 modification to the JMJD3c.

It is appropriate that the "sequence homology" be generally 70% or more, preferably 80%, more preferably 85% or more, still more preferably 90% or more, even more preferably 95% or more, most preferably 98% or more of an entire amino acid sequence.

Further, the JMJD3 gene of the present disclosure encompasses the following:

(1) a gene encoding a polypeptide formed of an amino acid sequence set forth in any one of SEQ ID NOS: 1 to 3;

(2) a gene encoding a polypeptide that has 1 to 20 (or 1 to 15, 1 to 10, 1 to 7, 1 to 5, or 1 to 3) amino acids substituted, deleted, inserted, and/or added in the amino acid sequence set forth in any one of SEQ ID NOS: 1 to 3 and has a substantially equivalent action of substantially removing or reducing H3K27me3 modification to that of the amino acid sequence set forth in any one of SEQ ID NOS: 1 to 3;

(3) a gene encoding a polypeptide that has 90% (or 92%, 94%, 96%, 98%, or 99%) or more homology to the amino acid sequence set forth in any one of SEQ ID NOS: 1 to 3 and has a substantially equivalent action of substantially removing or reducing H3K27me3 modification to that of the amino acid sequence set forth in any one of SEQ ID NOS: 1 to 3;

(4) a gene formed of a base sequence set forth in any one of SEQ ID NOS: 4 to 6;

(5) a gene encoding a polypeptide that hybridizes with a base sequence complementary to the base sequence set forth in any one of SEQ ID NOS: 4 to 6 under stringent conditions and has a substantially equivalent action of substantially removing or reducing H3K27me3 modification to that of the amino acid sequence set forth in any one of SEQ ID NOS: 1 to 3;

(6) a gene that has a sequence of 1 to 50 (or 1 to 40, 1 to 30, 1 to 20, 1 to 15, 1 to 10, 1 to 5, or 1 to 3 bases substituted, deleted, inserted, and/or added in the gene (DNA) formed of the base sequence set forth in any one of SEQ ID NOS: 4 to 6; and (7) a gene having 90% (or 92%, 94%, 96%, 98%, or 99%) or more homology to the gene formed of the base sequence set forth in any one of SEQ ID NOS: 4 to 6.

(Transcription Factor Required for Highly Efficient Induction of Differentiation into Desired Cell Type)

The form of the "transcription factor required for highly efficient induction of differentiation into the desired cell type" to be used in the method of the present disclosure is not particularly limited, for examples thereof may include, but not particularly limited to, nucleic acids, such as RNA and DNA, synthetic nucleic acids, and proteins. The following examples may be given.

In addition, in the method of the present disclosure, examples of the desired cell type may include a skeletal muscle (skeletal muscle cells), the liver (liver cells), and nerve (nerve cells).

{Transcription Factor Required for Induction of Differentiation into Skeletal Muscle (in Particular, Cells Present in Skeletal Muscle)}

A method of inducing differentiation into a skeletal muscle is as described below.

A single transcription factor, or two or more transcription factors selected from the group consisting of MYOD1, NRF1, SALL4, ZIC1, KLF9, ZNF281, CTCF, HES1, HOXA2, TBX5, TP73, ERG, MAB21L3, PRDM1, NFIC, CTCFL, FOXP1, HEY1, PITX2, JUNB, KLF4, ESX1, TFAP2C, FOS, TFE3, FOSL1, GRHL2, TBX2, NFIB, and IRF4 are introduced into a pluripotent stem cell having a histone in which H3K27me3 modification has been substantially removed or reduced.

In particular, the JMJD3c gene (SEQ ID NO: 80) and MYOD1 (myogenic differentiation 1: SEQ ID NO: 86, SEQ ID NO: 88) are added to pluripotent stem cells known per se.

{Transcription Factor Required for Induction of Differentiation into Liver (in Particular, Cells Present in Liver, i.e., Liver Cells or Hepatoblasts)}

A method of inducing differentiation into the liver (in particular, the liver, liver cells, or the fetal liver) is as described below.

Liver: A single transcription factor, or two or more transcription factors selected from TCF-1, SALL4, TGIF1, MAB21L3, ZIC1, EGFLAM, PITX2, HNF4A, NRF1, ZNF281, CTCFL, TP73, TFE3, DLX6, and TCF4 are introduced into human pluripotent stem cells.

Fetal liver: A single transcription factor, or two or more transcription factors selected from TCF-1, SIX5, HNF4A, SIN3A, ID1, and HNF1A are introduced into human pluripotent stem cells.

In particular, the JMJD3c gene (SEQ ID NO: 80) and HNF1A (hepatocyte nuclear factor 1, alpha: SEQ ID NO: 87, SEQ ID NO: 94) are added to pluripotent stem cells known per se.

{Transcription Factor Required for Induction of Differentiation into Neural Cells (in Particular, Motoneurons or Peripheral Motoneuron Cells)}

A method of inducing differentiation into neural cells (in particular, motoneurons or peripheral motoneuron cells) is as described below.

A single transcription factor, or two or more, three or more, or four or more transcription factors selected from NEUROG1 (neurogenin 1: SEQ ID NO: 81), NEUROG2 (neurogenin 2: SEQ ID NO: 82), NEUROG3 (neurogenin 3: SEQ ID NO: 83), NEUROD1 (neurogenic differentiation 1: SEQ ID NO: 84), and NEUROD2 (neurogenic differentiation 2: SEQ ID NO: 85) or all of these transcription factors are introduced into human pluripotent stem cells.

In particular, the JMJD3c gene (SEQ ID NO: 80), and NEUROG1 (SEQ ID NO: 81, SEQ ID NO: 89), NEUROG2 (SEQ ID NO: 82, SEQ ID NO: 90), NEUROG3 (SEQ ID NO: 83, SEQ ID NO: 91), NEUROD1 (SEQ ID NO: 84, SEQ ID NO: 92), and NEUROD2 (SEQ ID NO: 85, SEQ ID NO: 93) are added to pluripotent stem cells known per se.

(Method of Introducing Target Gene into Genome of Pluripotent Stem Cell)

Figure 4:
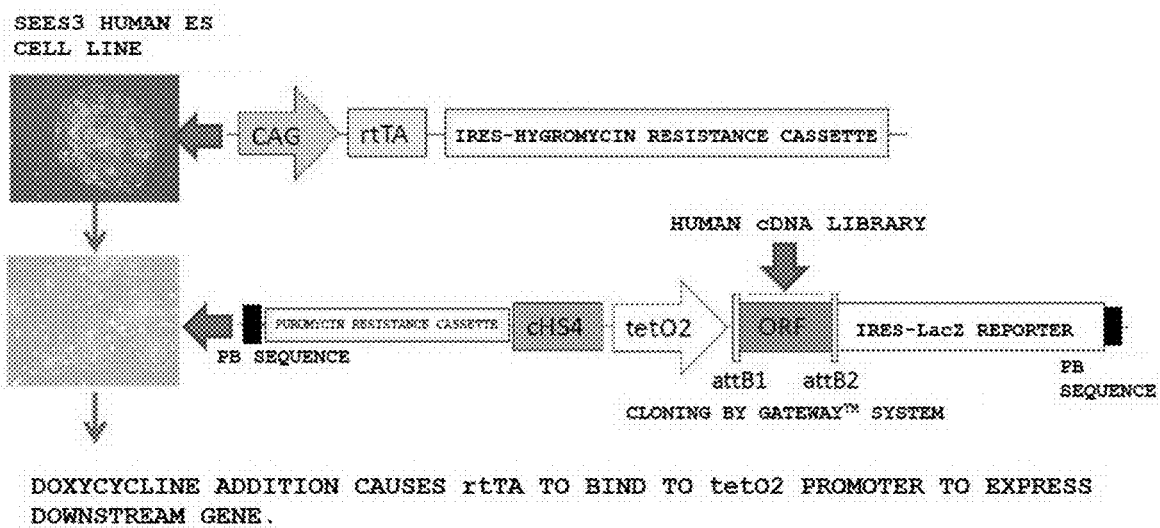
FIG. 4: A method of introducing a target gene into the genome of a pluripotent stem cell.

In a step of the method of the present disclosure, a method known per se may be used without any particular limitation as a method of introducing the gene for the compound having an action of substantially removing or reducing H3K27me3 modification and/or the transcription factor required for highly efficient induction of differentiation into the desired cell type into the genome of the pluripotent stem cell. There may be preferably used an expression cassette inserted between PiggyBac transposase recognition sequences (PB sequences) developed by Woltjen et al. (reference: Nature 458: 766-770, 2009), which is a mechanism by which a gene to be introduced is actively incorporated into pluripotent stem cells (in particular, the genome of human ES cells). The expression cassette is a system capable of efficiently establishing a genetically modified pluripotent stem cell line by introducing a drug selection cassette (see FIG. 4).

(Method of Introducing Target Protein into Pluripotent Stem Cell)

In a step of the method of the present disclosure, a method known per se may be used as a method of introducing the compound (in particular, protein) having an action of substantially removing or reducing H3K27me3 modification and/or the transcription factor (protein) required for highly efficient induction of differentiation into the desired cell type into the genome of the pluripotent stem cell, and examples thereof may include: a method involving using a protein transfection reagent; a method involving using a fusion protein having added thereto a cell-penetrating peptide; and a microinjection method.

The "cell membrane permeable peptide" of the present disclosure is a peptide having a property of migrating into a cell, more specifically a property of permeating a cell membrane, still more specifically a property of permeating a cell membrane or a nuclear membrane to permeate into cytoplasm or a nucleus. The amino acid sequence of the peptide is not particularly limited, but examples thereof may include TAT (GRKKRRQRRRPQ: SEQ ID NO: 7), r8 {rrrrrrrr (D-form-R): SEQ ID NO: 8}, and MPG-8 (βAFLGWLGAWGTMGWSPKKKRK: SEQ ID NO: 9).

The target protein encompasses both of the compound (in particular, protein) having an action of substantially removing or reducing H3K27me3 modification and/or the transcription factor (protein) required for highly efficient induction of differentiation into the desired cell type.

(Differentiation Induction Kit for Inducing Differentiation of Pluripotent Stem Cell into Desired Cell Type with High Efficiency)

A differentiation induction kit for inducing differentiation of a pluripotent stem cell into a desired cell type with high efficiency of the present disclosure (hereinafter sometimes referred to as "kit of the present disclosure") includes any one or more of the following embodiments.

(1) Pluripotent Stem Cell in which H3K27Me3 Modification has been Substantially Removed or Reduced A pluripotent stem cell in which H3K27me3 modification has been substantially removed or reduced can be easily generated by the method of the present disclosure described above.

A practitioner of the present disclosure can easily induce differentiation into the desired cell type by introducing the transcription factor required for induction of differentiation into the desired cell type as described above into the pluripotent stem cell in which H3K27me3 modification has been substantially removed or reduced.

In addition, the pluripotent stem cell in which H3K27me3 modification has been substantially removed or reduced encompasses a pluripotent stem cell having a gene construct inducible with doxycycline or the like inserted into the genome thereof so that a demethylase can be transiently forcibly expressed therein.

(2) Demethylase Gene for Kit of the Present Disclosure

A practitioner of the present disclosure can easily generate the pluripotent stem cell in which H3K27me3 modification has been substantially removed or reduced by adding a demethylase gene for a kit to a pluripotent stem cell known per se.

Examples of the demethylase gene for a kit may include, but not particularly limited to, mRNAs, DNAs, and proteins of demethylase genes (e.g., JMJD3c).

(3) Demethylase Gene for Kit and Gene Containing Transcription Factor Required for Induction of Differentiation into Desired Cell Type of the Present Disclosure.

A practitioner of the present disclosure can easily generate the pluripotent stem cell in which H3K27me3 modification has been substantially removed or reduced, and induce differentiation into the desired cell type with high efficiency by adding the demethylase gene for a kit and a gene containing the transcription factor required for induction of differentiation into the desired cell type to a pluripotent stem cell known per se.

The two genes may be present on one gene, or on separate genes. When the two genes are present on separate genes, the demethylase gene and the transcription factor required for induction of differentiation into the desired cell type may be added to the pluripotent stem cell simultaneously or at separate times.

(4) Demethylase for Kit of the Present Disclosure

A practitioner of the present disclosure can easily generate the pluripotent stem cell in which H3K27me3 modification has been substantially removed or reduced by adding a demethylase for a kit to a pluripotent stem cell known per se.

(5) Gene Construct Carrying Demethylase Gene of the Present Disclosure

A practitioner of the present disclosure can easily generate the pluripotent stem cell in which H3K27me3 modification has been substantially removed or reduced by introducing a gene construct carrying a demethylase gene into the genome of a pluripotent stem cell known per se.

The gene construct may contain a promoter sequence, a gene expression-enhancing sequence, a marker gene, a reporter sequence, a drug resistance gene, and the like as required in addition to the demethylase gene.

(6) Gene Construct Carrying Demethylase Gene and Transcription Factor Required for Induction of Differentiation into Desired Cell Type of the Present Disclosure A practitioner of the present disclosure can easily generate the pluripotent stem cell in which H3K27me3 modification has been substantially removed or reduced, and induce differentiation into the desired cell type by introducing a gene construct carrying a demethylase gene and a transcription factor required for induction of differentiation into the desired cell type into the genome of a pluripotent stem cell known per se.

The two genes may be present on one gene, or on separate genes. When the two genes are present on separate genes, the demethylase gene and the transcription factor required for induction of differentiation into the desired cell type may be introduced into the genome of the pluripotent stem cell simultaneously or at separate times.

The gene construct may contain a promoter sequence, a gene expression-enhancing sequence, a marker gene, a reporter sequence, a drug resistance gene, and the like as required in addition to the demethylase gene and the transcription factor required for induction of differentiation into the desired cell type.

A method of differentiating a pluripotent stem cell into a desired cell type of the present disclosure may be exemplified by, but not particularly limited to, a method including any one of the following steps (1) to (7):

(1) a step of adding a demethylase gene and a transcription factor required for induction of differentiation into the desired cell type to a pluripotent stem cell;

(2) a step of inserting a gene construct carrying a demethylase gene and a transcription factor gene required for induction of differentiation into the desired cell type into a genome of a pluripotent stem cell;

(3) a step of inserting a gene construct carrying a demethylase gene into a genome of a pluripotent stem cell, followed by addition of a transcription factor required for induction of differentiation into the desired cell type to the cell;

(4) a step of inserting a gene construct carrying a demethylase gene and a gene construct carrying a transcription factor required for induction of differentiation into the desired cell type into a genome of a pluripotent stem cell;

(5) a step of adding a transcription factor required for induction of differentiation into the desired cell type to a pluripotent stem cell having a histone in which H3K27me3 modification has been substantially removed or reduced;

(6) a step of adding a transcription factor required for induction of differentiation into the desired cell type to a pluripotent stem cell in which a demethylase is forcibly expressed; and (7) a step of adding a demethylase and a transcription factor required for differentiation into the desired cell type to a pluripotent stem cell.

The present disclosure also encompasses any one of the following pluripotent stem cells for differentiation into a desired cell type:

(1) a pluripotent stem cell for differentiation into a desired cell type, which has a histone in which H3K27me3 modification has been substantially removed or reduced;

(2) a pluripotent stem cell for differentiation into a desired cell type, in which a demethylase is forcibly expressed; and (3) a pluripotent stem cell for differentiation into a desired cell type, which has a gene construct carrying a demethylase gene inserted into the genome thereof.

The present disclosure also encompasses a use of any one of the following pluripotent stem cells for differentiation into a desired cell type:

(1) a pluripotent stem cell for differentiation into a desired cell type, which has a histone in which H3K27me3 modification has been substantially removed or reduced;

(2) a pluripotent stem cell for differentiation into a desired cell type, in which a demethylase is forcibly expressed; and (3) a pluripotent stem cell for differentiation into a desired cell type, which has a gene construct carrying a demethylase gene inserted into the genome thereof.

The present disclosure also encompasses a use of any one of the following pluripotent stem cells for differentiation into a desired cell type, in production of a differentiation induction kit for differentiating a pluripotent stem cell into a desired cell type:

(1) a pluripotent stem cell for differentiation into a desired cell type, which has a histone in which H3K27me3 modification has been substantially removed or reduced;

(2) a pluripotent stem cell for differentiation into a desired cell type, in which a demethylase is forcibly expressed; and (3) a pluripotent stem cell for differentiation into a desired cell type, which has a gene construct carrying a demethylase gene inserted into the genome thereof.

The present disclosure is specifically described below by way of Examples. However, the present disclosure is not limited thereto. All of these Examples were carried out after being approved by the Ethics Committee of Keio University School of Medicine.

Example 1

(Materials and Methods)

Examples 2 to 7 were carried out using materials and methods described below. The details are as described below.

(Human Pluripotent Stem Cell Culture and Differentiation Induction Methods)

A human ES cell (hESC) lineage SEES-3 was obtained from the National Center for Child Health and Development, Japan (National Research Institute for Child Health and Development). Human induced pluripotent stem cells (hiPSCs) were generated from adult human fibroblasts by introducing mRNAs for POU5F1, SOX2, KLF4, and c-MYC. hESC/iPSCs were maintained under feeder cell-free conditions using StemFitAK-03medium (Ajinomoto) on iMatrix-511 (Nippi)-coated plates. A ROCK inhibitor Y-27632 was added to the medium during cell subculture in order to prevent detachment-induced apoptosis.

For early differentiation, the hESCs were cultured in a differentiation medium of RPMI 1640 (Gibco) supplemented with growth factors (100 ng/ml activin A for endodermal differentiation and 100 ng/ml activin A on Day 1, which was replaced with 10 ng/ml BMP4 and ng/ml bFGF for mesodermal differentiation). For myogenic differentiation, the hPSCs were cultured in a medium of αMEM (Gibco) supplemented with 5% KSR, 1 mM sodium pyruvate, 0.1 mM non-essential amino acids, 2 mM glutamine, 0.1 mM β-mercaptoethanol, and penicillin/streptomycin (50 U/50 μg/ml) on iMatrix-511 or Matrigel (BD)-coated plates.

(Generation of JMJD3c-hESCs)

A full-length human JMJD3 clone was obtained from Addgene (plasmid ID #24167). A point mutation in the catalytic domain was introduced using PrimeSTAR Mutagenesis Basal Kit (Takara). HA-tagged JMJD3c and a mutant thereof were subcloned into a PiggyBac construct containing a tetracycline-responsive element IRES-βgeo, and a puromycin resistance gene controlled by a PGK promoter. Vectors were simultaneously introduced with PiggyBac transposase vectors into hESCs that consistently expressed a reverse tetracycline transactivator (SEE3-1v) using a GeneJuice transfection reagent (Novagen). Stable clones were established by puromycin selection. Inducible expression with doxycycline treatment was confirmed by X-Gal staining.

(Modified mRNA Synthesis and Transfection)

The protein-coding regions (Open Reading Frames, ORFs) of a red fluorescent protein mCherry, a green fluorescent protein Emerald and human influenza virus hemagglutinin (Hemagglutinin, HA)-tagged full-length or catalytic domains of JMJD3, and UTX were subcloned into a pCRII construct containing the 5' UTR and 3' UTR of mouse α-globin, which increased mRNA stability and translation efficiency, to prepare templates used to synthesize mRNAs.

Modified mRNAs were synthesized on the basis of the description of the literature "Cell stem cell 7, 618-630 (2010)". Briefly speaking, a T7 promoter and a poly (A) tail were added through PCR reaction using a KAPA taq kit (Kapa Biosystems). RNAs were synthesized from PCR products using a MEGAscript T7 kit (Ambion) together with ARCA cap analog (New England Biolabs), ATP, GTP, 5-Methyl-CTP (TriLink), and pseudo-UTP (TriLink). The synthetic mRNAs were purified using a MEGAclear kit (Ambion). RNA transfections were performed with Lipofectamine 2000 (Invitrogen) or Lipofectamine Messenger Max (Invitrogen), according to the instructions of the accompanying manual. The B18R interferon inhibitor (eBioscience) was added to the culture medium to increase the viability of the transfected cells. The medium was replaced 2 hours to 3 hours after each transfection.

(Antibody)

The following antibodies were used:
HA (Abcam #ab9110 for immunoblotting method and #ab18181 for immunostaining);
H3K4me3 (Millipore #07-473);
H3K27me3 (Millipore #07-449);
H3K27ac (Active Motif #39-133);
panH3 (Abcam #ab1791); and
MHC (R&D #MAB4470).

(Immunostaining)

The cells were fixed in 4% PFA for 10 minutes at room temperature and permeabilized in 0.5% Triton-X-containing PBS for 10 minutes. The cells were blocked in 2% BSA-containing PBS for 10 minutes, and cultured with primary antibodies in a blocking solution (1:500) for from 2 hours to 3 hours at room temperature or overnight at 4° C. The cells were washed twice in PBS, and then cultured with Alexa dye-conjugated secondary antibodies (Invitrogen) in a blocking solution (1:500) for 1 hour at room temperature. Nuclei were counterstained with DAPI (Dako) for 5 minutes at room temperature. Immunofluorescence was visualized with an inverted fluorescence microscope IX73 (Olympus). Images were obtained using Olympus cellSens imaging software.

(Immunoblotting Method)

The cells were lysed with a sample buffer (50 mM Tris-HCl, pH 6.8, 2% SDS, 6% 2-mercaptoethanol, and 500 mg/ml urea). The proteins were separated by SDS-PAGE using a 4-15% polyacrylamide gel (Biorad) and were electrically transferred to polyvinylidene fluoride membranes (Biorad). The membranes were blocked for 1 hour in 0.1% Tween-20-containing Tris-buffered saline (TBST) and 5% skimmed milk. The membranes were washed in TBST and then incubated with primary antibodies in 2% BSA-containing TBS (1:1,000 dilution) overnight at 4° C. The membranes were washed and then incubated with horseradish peroxidase-conjugated secondary antibodies (GE) for 1 hour at room temperature. The membranes were washed in TEST, and immunoreactivity was visualized using ECL Prime Detection Kit (GE) and detected using Luminescent Image Analyzer (LAS-4000; Fujifilm).

(qRT-PCR)

Total RNA was isolated with TRIzol reagent (Invitrogen), and cDNAs were generated with random hexamers using a Superscript III First-strand Synthesis kit (Invitrogen). Real-time PCR was performed using a SYBR Green PCR system (Takara). The primer sequences used for RT-PCR are listed in Tables 1 and 2 below.

TABLE 1

| qRT-PCR | Forward | Reverse |
|---|---|---|
| GAPDH | GGTGGTCTCCTCTGACTTCAACA (SEQ ID NO: 10) | GTGGTCGTTGAGGGCAATG (SEQ ID NO: 11) |
| POU5F1 | CTTGAATCCCGAATGGAAAGGG (SEQ ID NO: 12) | GTGTATATCCCAGGGTGATCCTC (SEQ ID NO: 13) |
| NANOG | AGAAGGCCTCAGCACCTAC (SEQ ID NO: 14) | GGCCTGATTGTTCCAGGATT (SEQ ID NO: 15) |
| T | GCCCTCTCCCTCCCCTCCACGCACAG (SEQ ID NO: 16) | CGGCGCCGTTGCTCACAGACCACAGG 17)(SEQ ID NO: |
| MSX1 | CGAGAGGACCCCGTGGATGCAGAG (SEQ ID NO: 18) | GGCGGCCATCTTCAGCTTCTCCAG (SEQ ID NO: 19) |
| SOX17 | CGCTTTCATGGTGTGGGCTAAGGACG (SEQ ID NO: 20) | TAGTTGGGGTGGTCCTGCATGTGCTG (SEQ ID NO: 21) |
| FOXA2 | TGGGAGCGGTGAAGATGGAAGGGCAC (SEQ ID NO: 22) | TCATGCCAGCGCCCACGTACGACGAC (SEQ ID NO: 23) |
| GATA4 | GCTCCTTCAGGCAGTGAGAG (SEQ ID NO: 24) | CTGTGCCCGTAGTGAGATGA (SEQ ID NO: 25) |
| GATA6 | GTGCCCAGACCACTTGCTAT (SEQ ID NO: 26) | TGGAGTCATGGGAATGGAAT (SEQ ID NO: 27) |
| GSC | CGGTCCTCATCAGAGGAGTC (SEQ ID NO: 28) | CCGAGTCCAAATCGCTTTTA (SEQ ID NO: 29) |
| EVX1 | CGGCTGGAGAAGGAATTCTA (SEQ ID NO: 30) | ACACCTTGATGGTGGTTTCC (SEQ ID NO: 31) |
| MYOG | GCCAGACTATCCCCTTCCTC (SEQ ID NO: 32) | GAGGCCGCGTTATGATAAAA (SEQ ID NO: 33) |
| MEF2C | AGGTCACCTGACATCCCAAG (SEQ ID NO: 34) | GTTAGCCCTCCAACTCCACA (SEQ ID NO: 35) |
| CKM | GAAGAGCATGACGGAGAAGG (SEQ ID NO: 36) | GTTGTCATTGTGCCAGATGC (SEQ ID NO: 37) |
| SIX1 | TGTTTGCGCATAAAGGAATG (SEQ ID NO: 38) | TGGGAAGGAAAATGCAAAAG (SEQ ID NO: 39) |
| AFP | TGGGACCCGAACTTTCCA (SEQ ID NO: 40) | GGCCACATCCAGGACTAGTTTC (SEQ ID NO: 41) |

TABLE 1-continued

| qRT-PCR | Forward | Reverse |
|---|---|---|
| COL2 | TTTCCCAGGTCAAGATGGTC (SEQ ID NO: 42) | CTTCAGCACCTGTCTCACCA (SEQ ID NO: 43) |
| COL1A1 | CCTGGATGCCATCAAAGTCT (SEQ ID NO: 44) | TCTTGTCCTTGGGGTTCTTG (SEQ ID NO: 45) |

TABLE 2

| ChIP-PCR | Forward | Reverse |
|---|---|---|
| POU5F1 | GGAGGTAAACCCAGCTCACA (SEQ ID NO: 46) | TTTGGCCTTAGGGTTAAGCA (SEQ ID NO: 47) |
| NANOG | GCTCAGGGATGAGCATGATT (SEQ ID NO: 48) | TGCCCAGTAACATCCACAAA (SEQ ID NO: 49) |
| T | GGCACGGCCAAATAAGAATA (SEQ ID NO: 50) | GGTTCAATTCCTGGGTCGTA (SEQ ID NO: 51) |
| MSX1 | TCCCTCATCTGATCCCAAAC (SEQ ID NO: 52) | ACCAGCTCCTACTGCGAGAA (SEQ ID NO: 53) |
| SOX17 | AGCAAGATGCTGGGTGAGTC (SEQ ID NO: 54) | CTACACACCCCTGGTTTTGG (SEQ ID NO: 55) |
| FOXA2 | TTCTTCGCTCTCAGTGCTCA (SEQ ID NO: 56) | GGCGAGTTAAAGGTGTGTACG (SEQ ID NO: 57) |
| GATA4 | GATCTTCGCGACAGTTCCTC (SEQ ID NO: 58) | CATGGCCAAGCTCTGATACA (SEQ ID NO: 59) |
| GATA6 | TGCAGCCTACGCTCTTGTTA (SEQ ID NO: 60) | GTCAGTCAAGGCCATCCAC (SEQ ID NO: 61) |
| GSC | GACATGACGGAGATGGGTCT (SEQ ID NO: 62) | TGGAAGGTGCCTCACTTCTT (SEQ ID NO: 63) |
| EVX1 | TCACACTCTCCTCCCCAATC (SEQ ID NO: 64) | TTACAGTACCGCTGGTGACG (SEQ ID NO: 65) |
| GAPDH | CGGTGACTAACCCTGCGCTCCTG (SEQ ID NO: 66) | AGCTAGCCTCGCTCCACCTGACTT (SEQ ID NO: 67) |
| MYOG_a | CCTCCGGAAAGAATGGGACT (SEQ ID NO: 68) | TCTGTTAGCTGCTCTGAGTCT (SEQ ID NO: 69) |
| MYOG_b | TTGGAGCCAAGGTTACCAGT (SEQ ID NO: 70) | CTCTCACAGCGCCTCCTG (SEQ ID NO: 71) |
| MYOG_c | GGCCTCATTCACCTTCTTGA (SEQ ID NO: 72) | TGGGCGTGTAAGGTGTGTAA (SEQ ID NO: 73) |
| MEF2C_a | CATGCATTTTCAGGTCACCA (SEQ ID NO: 74) | CCCCTCCACTTTGATTCGTA (SEQ ID NO: 75) |
| MEF2C_b | GCACGTTTAAGACCCCAAAG (SEQ ID NO: 76) | CGGCCTCAGCTAAATGAAAG (SEQ ID NO: 77) |
| SOX1 | CCGTCTCACTCCGTCTGAAT (SEQ ID NO: 78) | AGTGCAGGTCGGTCTCCAT (SEQ ID NO: 79) |

{Chromatin Immunoprecipitation (ChIP) Analysis}

The cells were crosslinked with formaldehyde in PBS (final concentration: 1%) at room temperature for 10 minutes. The reaction was quenched with glycine (final concentration: 125 M). The cells were washed with PBS, and stored at −80° C. until use. The cells were lysed in protease inhibitor cocktail-containing Lysis buffer 3 (10 mM Tris-HCl, pH 8.0, 100 mM NaCl, 1 mM EDTA, 0.5 mM EGTA, 0.1% sodium deoxycholate, 0.5% N-lauroylsarcosine). Ultrasonication was performed using Handy Sonic UR-20P (Tomy Seiko Co., Ltd.) so as to generate DNA fragments of from about 150 bp to about 450 bp. The ultrasonicated lysate was diluted with protease inhibitor cocktail-containing ChIP dilution buffer (20 mM Tris-HCl, pH 8.0, 150 mM NaCl, 2 mM EDTA, 1% Triton X-100), and then cultured overnight at 4° C. together with 30 μl of protein G magnetic beads (Invitrogen) precultured with 3 μg of an antibody. The precipitate was washed three times with RIPA buffer (10 mM Tris-HCl, pH 7.5, 140 mM NaCl, 1 mM EDTA, 0.5 mM EGTA, 1% Triton X-100, 0.1% SDS, 0.1% sodium deoxycholate), and then washed once with 10 mM Tris-HCl, pH 8.0, 5 mM EDTA, 10 mM NaCl. Bound chromatin was eluted from the beads in elution buffer (20 mM Tris-HCl, pH 7.5, 5 mM EDTA, 50 mM NaCl, 1% SDS) at 68° C., and decrosslinked at 68° C. for 6 hours. DNA was treated with RNase A and protease K, and then purified by phenol-chloroform-isoamyl alcohol and isopropanol precipitation. Real-time PCR was performed using a SYBR Green PCR system (Takara). The primer sequences are listed in Tables 1 and 2 above.

(Coculture of Myogenic Cells and C2C12 Cells)

Induced myogenic cells were labeled with green fluorescence by introducing Emerald mRNA. The cells were cocultured with C2C12 cells expressing H2B-mCherry in a medium of DMEM (Gibco) supplemented with 2% horse serum.

(Statistical Analysis)

The statistical significance of differences between samples was assessed using Student's t-test for independent samples.

Example 2

(Generation of H3K27Me3-Deficient Pluripotent Stem Cells (Pluripotent Stem Cells Having Histone in which H3K27Me3 Modification has been Substantially Removed or Reduced))

In this Example, pluripotent stem cells in which H3K27me3 had been demethylated (H3K27me3-deficient hESCs) were generated. Specifically, in order to demethylate the H3K27me3 of pluripotent stem cells, two methods of manipulating the expression of the demethylase JMJD3 were used. The details are as described below.

(1) Use of Modified Synthetic mRNA

Figure 5A:
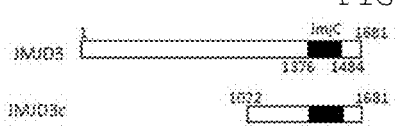
FIGS. 5A-5H: The generation of H3K27me3-attenuated hESCs by JMJD3c expression.

A forced expression system for JMJD3 was generated through use of modified synthetic mRNAs. mRNAs encoding full-length JMJD3 (JMJD3f) and the catalytic domain-containing C-terminus (JMJD3c) were synthesized in vitro (FIG. 5A).

Figure 5D:
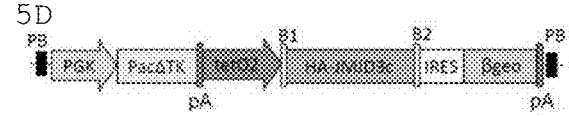
Figure 5B:
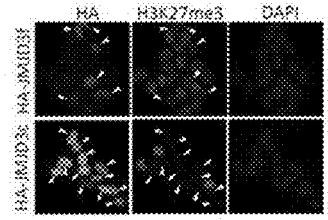
Figure 5E:
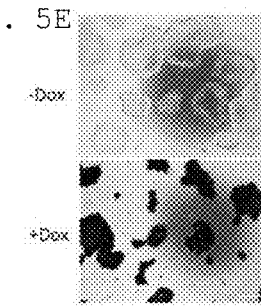
Figure 5F:
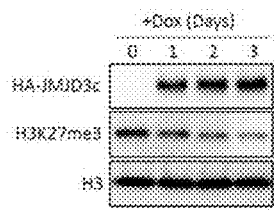
Figure 5C:
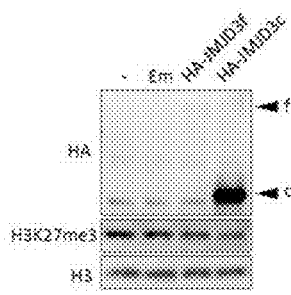

The N-terminus of each of those mRNAs was tagged with a hemagglutinin (HA) sequence for detecting a translated protein. At 8 hours after the introduction of the synthetic mRNAs into hESCs, the demethylation of H3K27me3 was detected by immunostaining and immunoblotting methods (FIG. 5B and FIG. 5C). The results showed that "the introduction of the JMJD3c mRNA induced a more significant decrease in H3K27me3 as compared to the JMJD3f mRNA," and the results showed that the catalytic domain of JMJD3 was able to sufficiently demethylate a nucleosome histone.

(2) Use of Plasmid Vector Having Inserted Therein Demethylase Gene

Figure 5G:
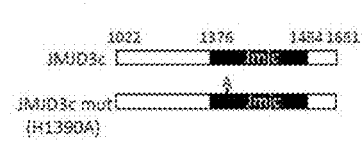
Figure 5H:
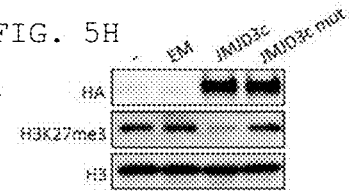

A forced expression system for JMJD3c was generated through use of a plasmid vector having introduced therein JMJD3c. More specifically, a hESC line in which the expression of HA-JMJD3c was regulated by doxycycline (Dox) treatment was generated (JMJD3c-hESC) (FIG. 5D). Dox treatment (1 μg/ml) induced HA-JMJD3c expression and a significant decrease in H3K27me3 in all hESCs (FIG. 5F). Forced expression of the JMJD3c mutant, which lacked catalytic function (FIG. 5G), did not induce any change in H3K27me3 (FIG. 5H). Thus, it was confirmed that JMJD3c removed or attenuated H3K27me3 through its demethylase activity.

That is, it was confirmed that pluripotent stem cells in which H3K27me3 modification had been substantially removed or reduced were generated.

It was confirmed that the expression level of H3K27me3 of pluripotent stem cells could be manipulated by each of the above-mentioned two methods. In addition, in the use of the modified synthetic mRNA, the timing and duration time of JMJD3c expression can be regulated, and hence the decrease in the expression level of H3K27me3 (or substantial removal of H3K27me3) can be performed at specific timing at which differentiation of pluripotent stem cells into a desired cell type is induced.

Example 3

(Confirmation of Changes in Developmental Genes in H3K27Me3-Deficient Pluripotent Stem Cells)

Figure 6A:
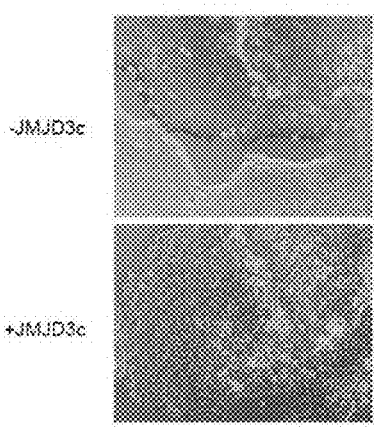
FIGS. 6A-6C: Development/differentiation-related genes whose gene expression are upregulated in JMJD3-hESCs.

It was revealed that forced expression of JMJD3c (H3K27me3-deficient pluripotent stem cells) resulted in morphological changes in hESCs toward differentiation (FIG. 6A). It was confirmed that the morphological changes occurred even under culture conditions for maintaining an undifferentiated state.

Figure 6B:
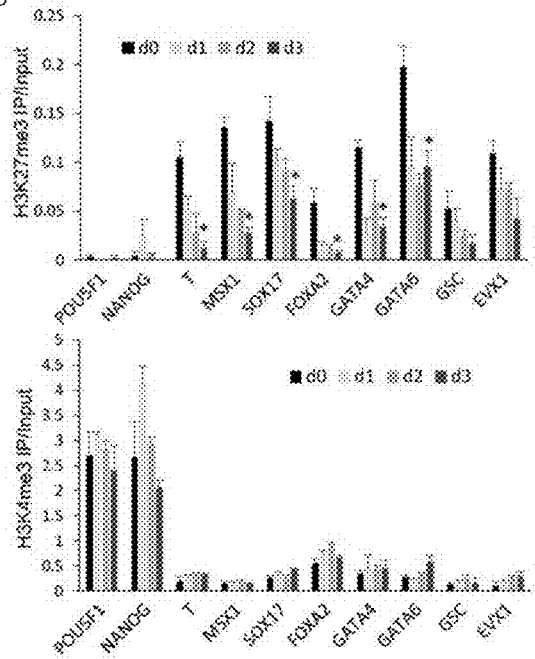

Chromatin immunoprecipitation (ChIP) analysis revealed that decreases in H3K27me3 occurred in the promoters of genes whose gene expression had been upregulated in Dox-treated JMJD3c-hESCs, but those regions were still rich in H3K4me3 (FIG. 6B). This result means that the chromatin structure is brought into an active state.

In this Example, it was shown that, by demethylating H3K27me3, JMJD3c expression was able to cause enhancement of the expression of development/differentiation-related genes over cell differentiation resistance (stem cell-maintaining property).

Figure 6C:
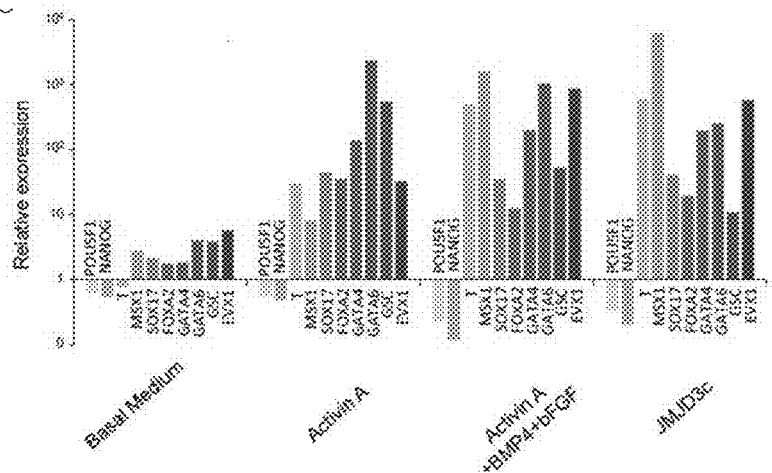

As described above, forced expression of JMJD3c upregulates the expression of development/differentiation-related genes. In particular, genes associated with endodermal and mesodermal differentiation, such as SOX17, FOXA2, GATA4/6, EOMES, T, and MIXL1, were highly expressed 3 days after the Dox treatment (FIG. 6C). Further, enhancement of the expression of those genes was found also under undifferentiated state-maintaining culture conditions. Typically, the differentiation of hESC/iPSCs into mesoderm/endoderm requires changes into a differentiation medium including various cytokines and growth factors (e.g., activin A, BMP, and FGF). In order to evaluate the influence of JMJD3c on gene expression enhancement for early differentiation, the expression levels of development/differentiation-related genes under JMJD3c-expressed conditions and conventional differentiation conditions were compared to each other. It was confirmed by real-time PCR analysis that JMJD3 upregulated the expression of developmental genes in a non-differentiation medium to a degree similar to that under differentiation conditions using cytokines and growth factors (FIG. 6C).

Those results suggest that ectopic expression (forced expression) of the demethylase allows a transition from a pluripotency-maintaining state to an early differentiation state by directly enhancing the expression of development/differentiation-related genes, and this does not require various cytokines and growth factors. That is, pluripotent stem cells in which H3K27me3 modification has been substantially removed or reduced easily undergo a transition from a pluripotent state to an early differentiation state.

Example 4

(Confirmation of Differentiation of Pluripotent Stem Cells in which Demethylase is Forcibly Expressed into Desired Cell Type)

In the above-mentioned Examples, it was confirmed that H3K27 demethylation by JMJD3c changes the chromatin structure of hESCs to an active form for highly efficient induction of differentiation into a desired cell type. In view of this, it was considered that, when a transcription factor required for induction of differentiation into a desired cell type was introduced, differentiation into the desired cell type was able to be induced with high efficiency. Accordingly, in this Example, as an example of induction of differentiation into a desired cell type, a myogenic differentiation model using a myogenesis-regulating master transcription factor MYOD1 was adopted. It is known that forced expression of MYOD1 alone cannot cause sufficient epigenetic changes and transcriptional changes in hESCs, resulting in poor myogenic conversion (see Cell Reports 3, 661-670 (2013)).

Figure 7A:
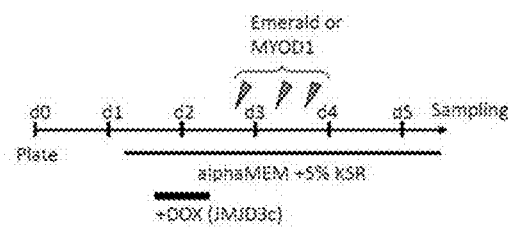
FIGS. 7A-7G: JMJD3c facilitates MYOD1-mediated muscle differentiation of hESCs.
Figure 7B:
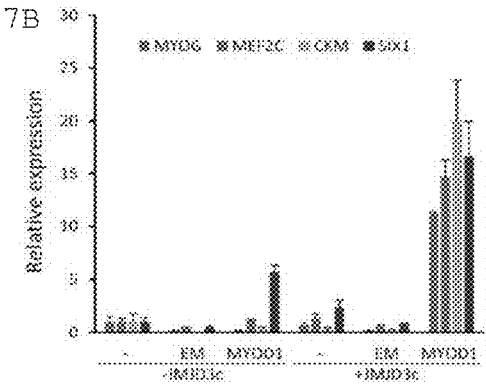

In order to confirm whether JMJD3c was able to facilitate MYOD1-induced muscle cell differentiation, JMJD3c was transiently forcibly expressed in hESCs before forced expression of MYOD1 (FIG. 7A).

In this process, the JMJD3c-hESC line was used, and induced by introducing JMJD3c and MYOD1 by means of Dox treatment and synthetic mRNA, respectively.

Alterations in the expression of four genes (MYOG, MEF2C, CKM, and SIX1) serving as markers for skeletal muscle differentiation were examined. Real-time PCR analysis revealed that forced expression of MYOD1 alone did not induce upregulation of the expression of the muscle cell differentiation-related genes except SIX1.

However, when JMJD3c was forcibly expressed before forced expression of MYOD1, all of those genes showed significant expression upregulation. However, forced expression of JMJD3c alone did not alter the expression pattern of MYOD1 downstream genes. Those results confirmed that JMJD3c facilitated muscle differentiation mediated by MYOD1 gene expression.

Figure 7C:
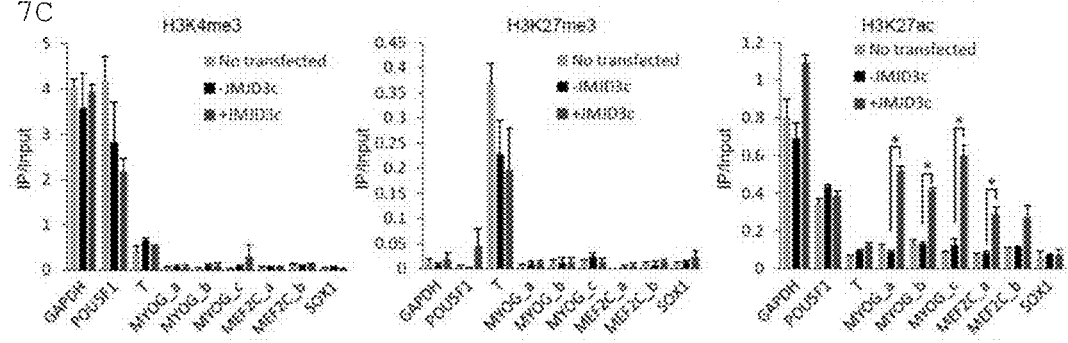

Further, chromatin changes in the promoter regions of MYOG and MEF2C during differentiation mediated by forced expression of MYOD1 with or without forced expression of JMJD3c were examined using ChIP assay. It was revealed that the levels of H3K4me3 and H3K27me3 in those regions were lower than those of a positive control, such as GAPDH, POU5F1, or Brachyury (T), in both the hESCs and the differentiated cells (FIG. 7C), and there was no large difference between a JMJD3c-positive condition and a negative condition. Meanwhile, it was revealed that those regions were significantly enriched for H3K27 acetylation (H3K27ac) in the differentiated cells only under the JMJD3c-positive condition, but not under the negative condition (FIG. 7C). H3K27ac has been known to be directly involved in active transcription. Thus, it was suggested that the combination of JMJD3c and MYOD1 formed an active state of chromatin in myogenic genes.

Figure 7D:
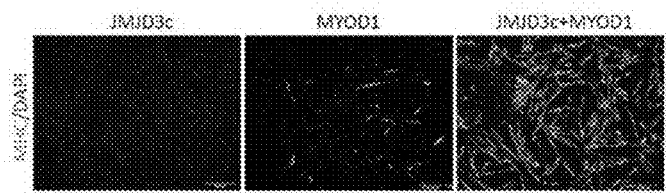
Figure 7E:
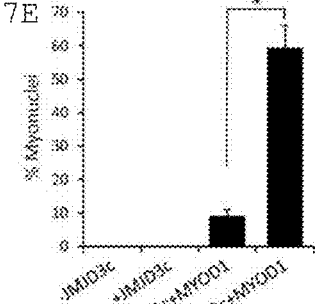
Figure 7F:
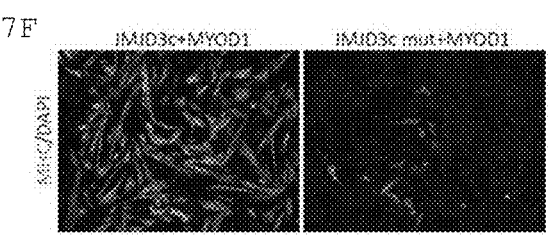
Figure 7G:
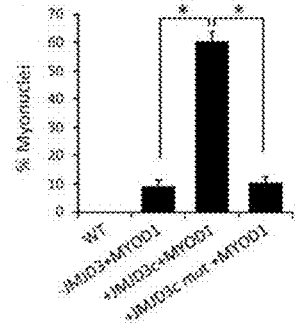

Further, it was confirmed that JMJD3c/MYOD1-forcibly expressing hESCs were myosin heavy chain (MHC)-positive, and changed to myotube-like morphology at 4 days post differentiation (FIG. 7D). The percentage of MHC-positive cells was much higher than the percentage observed under the condition of overexpressing MYOD1 alone (FIG. 7E). Those results show that JMJD3c facilitates MYOD1-mediated differentiation of hESCs into skeletal muscle cells. However, forced expression of the JMJD3c mutant did not induce MYOD1-mediated myogenic differentiation (FIG. 7F and FIG. 7G). Thus, it was confirmed that the demethylation of H3K27me3 was essential to MYOD1-mediated differentiation of hESCs into muscle cells.

As apparent from the foregoing, differentiation into a desired cell type can be efficiently induced by introducing a transcription factor required for induction of differentiation into the desired cell type into H3K27me3-deficient cells (pluripotent stem cells having a histone in which H3K27me3 modification has been substantially removed or reduced).

Example 5

(Confirmation of Differentiation of Pluripotent Stem Cells into Desired Cell Type Using Synthetic mRNA)

In Example 4 described above, it was confirmed that forced expression of the demethylase was able to facilitate MYOD1-mediated differentiation of hESCs into skeletal muscle cells.

In this Example, it was confirmed whether differentiation of hESCs into skeletal muscle cells was able to be induced by using only synthetic mRNAs for the demethylase JMJD3c and the transcription factor MYOD1 required for induction of differentiation into a desired cell type without altering the DNA of the pluripotent stem cells.

The mRNA for JMJD3c was transfected into hESCs twice, followed by three transfections with the MYOD1 mRNA (FIG. 8A). Two days after the last transfection of the MYOD1 mRNA, the majority of hESCs were differentiated into MHC-positive cells (FIG. 8B and FIG. 8C). As a control, hESCs were transfected with mRNAs for mCherry and MYOD1, but myogenic differentiation was not induced.

Some MHC-positive cells appeared to be fused cells (FIG. 8D), which was able to be further confirmed by a fusion assay with mouse C2C12 cells (FIG. 8E). Those results were able to confirm that the induced myotube-like cells became mature skeletal muscles in vitro.

Further, it was confirmed that the mRNA for JMJD3c facilitated MYOD1-mediated myogenic differentiation of fibroblast-derived hiPSCs (FIG. 8F and FIG. 8G). This suggests that JMJD3c facilitates direct conversion from a pluripotent state to a terminal differentiation state.

As apparent from the foregoing, differentiation into a desired cell type can be induced with high efficiency by introducing (adding) a transcription factor required for induction of differentiation into the desired cell type into pluripotent stem cells in which H3K27me3 modification has been substantially removed or reduced.

In related art, it is shown that skeletal muscle cells can be induced even when MYOD1 is used alone. However, in Non Patent Literature 4, drug selection needs to be performed in order to stably express the MYOD1 gene, and preculture is required for about 10 days prior to the initiation of differentiation induction. In addition, in Non Patent Literature 3, a PAX7 gene is introduced instead of the MYOD1 gene, but differentiation induction requires culture for about 1 month.

In addition, there is a report that skeletal muscle differentiation is induced by introducing a gene called BAF60C, and then introducing the MYOD1 gene (see Cell Rep. 2013Mar. 28; 3 (3): 661-70). However, differentiation induction takes 20 days, and requires the use of a lentiviral vector.

Example 6

(Transcription Factors Differentiate Pluripotent Stem Cells into Desired Cell Types)

In Examples 4 and 5 described above, it was confirmed that MYOD1-mediated induction of differentiation of hESCs into skeletal muscle cells was able to be facilitated by forcibly expressing the demethylase or adding the synthetic mRNA for the demethylase.

In this Example, it was confirmed whether differentiation of pluripotent stem cells into a plurality of desired cell types was able to be induced using respective transcription factors.

With reference to the method described in Example 4, JMJD3c-hESCs were treated with Dox (+JMJD3c) or without Dox (−JMJD3c) on from Day 1 to Day 2 after plating, and then, during Day 2, synthetic mRNA for TCF1, SOX9, RUNX3, or mCherry was introduced twice. The cells were collected on Day 4, and the expression of each differentiation marker gene was examined by RT-qPCR analysis.

The analysis results are shown in FIG. 9. In the cells transfected with the TCF1 transcription factor, AFP serving as a marker gene for hepatoblasts was significantly increased. In the cells transfected with the SOX9 transcription factor, COL2 serving as a marker gene for chondrocytes was significantly increased. In the cells transfected with the RUNX3 transcription factor, COL1A1 serving as a marker gene for osteoblasts was significantly increased.

Thus, it was confirmed that differentiation into desired cell types were able to be efficiently induced by introducing the transcription factors required for induction of differentiation into the desired cell types into H3K27me3-deficient cells (pluripotent stem cells having a histone in which H3K27me3 modification has been substantially removed or reduced).

Example 7

(Examples of Differentiation into Desired Cell Types Using Pluripotent Stem Cells of the Present Disclosure)

In this Example, differentiation into various desired cell types was confirmed using pluripotent stem cells having a histone in which H3K27me3 modification had been substantially removed or reduced.

(Differentiation into Skeletal Muscle Cells)

With reference to the description of Example 5, during 4-day culture, human pluripotent stem cells were transfected with the JMJD3c gene (SEQ ID NO: 80) twice, and then transfected with the MYOD1 gene (SEQ ID NO: 86, SEQ ID NO: 88) three times. It was confirmed that the cells were differentiated into skeletal muscle cells through the 4-day culture.

(Differentiation into Liver Cells)

With reference to the description of Example 5, during 4-day culture, human pluripotent stem cells were transfected with the JMJD3c gene (SEQ ID NO: 80) twice, and then transfected with the HNF1A gene (SEQ ID NO: 87, SEQ ID NO: 94) three times. It was confirmed that the cells were differentiated into liver cells through the 4-day culture.

(Differentiation into Nerve Cells)

With reference to the description of Example 5, during 4-day culture, human pluripotent stem cells were transfected with the JMJD3c gene (SEQ ID NO: 80) twice, and then transfected with the NEUROG1 gene (SEQ ID NO: 81, SEQ ID NO: 89), the NEUROG2 gene (SEQ ID NO: 82, SEQ ID NO: 90), the NEUROG3 gene (SEQ ID NO: 83, SEQ ID NO: 91), the NEUROD1 gene (SEQ ID NO: 84, SEQ ID NO: 92), and the NEUROD2 gene (SEQ ID NO: 85, SEQ ID NO: 93) three times. It was confirmed that the cells were differentiated into nerve cells through the 4-day culture.

Subject Matter of the Present Invention

It has been confirmed that, in the method of the present disclosure, a differentiation efficiency of from 60% to 70% is achieved in 4 days from the initiation of differentiation induction without the addition of various cytokines and growth factors required for causing a transition from a pluripotent state to an early differentiation state and with only the addition of synthetic mRNA to pluripotent stem cells. That is, in the method of the present disclosure, differentiation induction can be achieved within a shorter period and with higher efficiency without requiring the various cytokines and growth factors that are required in related-art methods.

In Examples of the present disclosure, even when there was no environmental change, a histone demethylase {in particular, the catalytic domain of JMJD3 (JMJD3c)} enhanced the expression of development/differentiation-related genes in pluripotent stem cells, and facilitated the conversion of a gene expression pattern from a pluripotent stem cell pattern to a gene expression pattern of a differentiated cell. This suggests that, without being limited to JMJD3, any demethylase having an effect of removing or attenuating methylation suppressing the expression of development/differentiation-related genes can facilitate cell differentiation of pluripotent stem cells into differentiated cells.

In Examples of the present disclosure, it has been shown that the histone demethylase JMJD3 cancels the suppression of the expression of the differentiation-related genes by rapidly attenuating the methylation of H3K27. Particularly when modified synthetic mRNA for JMJD3c was used, significant attenuation of H3K27me3 was confirmed in several hours. Those results show that the histone demethylase antagonistically regulates H3K27 methylation by a PcG complex in human pluripotent stem cells.

In the pluripotent stem cells, forced expression of the histone demethylase caused demethylation of H3K27me3, and upregulated gene expression of many development/differentiation-related genes. Those changes were also found under human pluripotent stem cell culture conditions for maintaining pluripotency. The mutant of the histone demethylase (function-deficient mutant of JMJD3c) did not induce those phenomena, revealing that specific demethylation of H3K27 by the demethylase was directly involved in the increase of the transcription activity of development/differentiation-related genes.

In Examples of the present disclosure, it has also been revealed that, in the group of development/differentiation-related genes whose gene expression is upregulated by the demethylase activity of JMJD3, more mesodermal/endodermal differentiation related genes are included than genes involved in ectodermal differentiation. This shows that the demethylase activity of the JMJD3 gene effectively facilitates differentiation into mesendodermal cells, specifically bone, muscle, liver, circulatory, digestive, and reproductive cells. However, the demethylase activity of JMJD3 gene also upregulated the expression of a group of genes involved in ectodermal differentiation as compared to that in pluripotent stem cells, and hence is likely involved also in facilitating differentiation into, for example, nerve and epidermal cells.

H3K27me3 is not present in large amounts in the promoter regions of muscle cell differentiation-related genes in hESCs, and hence the demethylase activity of JMJD3c is considered to be indirectly involved in enhancement of the expression of the muscle cell differentiation-related genes via enhancement of the expression of a gene involved in early development/cell differentiation.

Thus, it has been shown that the demethylase activity allows the state of cells to undergo a transition from a pluripotency-maintaining state to a differentiated state by attenuating differentiation resistance of pluripotent stem cells. The attenuation of the differentiation resistance is not limited to only the activation of muscle differentiation-related genes, but also facilitates the activation of other differentiated cell genes.

INDUSTRIAL APPLICABILITY

According to the present disclosure, the novel method of differentiating a pluripotent stem cell into a desired cell type with high efficiency can be provided.

The invention claimed is:

1. A method of differentiating a pluripotent stem cell into a desired cell type, comprising any one of the following steps (1) to (7):
   (1) a step of adding JMJD3 and a transcription factor required for induction of differentiation into the desired cell type to a pluripotent stem cell;
   (2) a step of inserting a gene construct carrying JMJD3 and a transcription factor gene required for induction of differentiation into the desired cell type into a genome of a pluripotent stem cell;
   (3) a step of inserting a gene construct carrying JMJD3 into a genome of a pluripotent stem cell, followed by addition of a transcription factor required for induction of differentiation into the desired cell type to the cell;
   (4) a step of inserting a gene construct carrying JMJD3 and a gene construct carrying a transcription factor required for induction of differentiation into the desired cell type into a genome of a pluripotent stem cell;
   (5) a step of adding a transcription factor required for induction of differentiation into the desired cell type to a pluripotent stem cell having a histone in which H3K27me3 modification has been substantially removed or reduced;
   (6) a step of adding a transcription factor required for induction of differentiation into the desired cell type to a pluripotent stem cell in which JMJD3 is forcibly expressed; and
   (7) a step of adding JMJD3 and a transcription factor required for differentiation into the desired cell type to a pluripotent stem cell,
   wherein the JMJD3 has demethylase activity that induces differentiation of the pluripotent stem cell by removing a methyl group of H3K27me3.

2. A method of differentiating a pluripotent stem cell into a desired cell type according to claim 1, wherein the method comprises the step (1), (3), (6), or (7).

3. A method of differentiating a pluripotent stem cell into a desired cell type according to claim 1, wherein the JMJD3 is a demethylase containing only an enzymatically active region of JMJD3.

4. A method of differentiating a pluripotent stem cell into a desired cell type according to claim 1, wherein the JMJD3 has an amino acid sequence set forth in any one of SEQ ID NOS: 1 to 3.

5. A method of differentiating a pluripotent stem cell into a desired cell type according to claim 1, wherein the desired cell type is a skeletal muscle cell, comprising any one of the following steps (1) to (7):
   (1) a step of adding JMJD3 and a transcription factor MYOD1 to a pluripotent stem cell;
   (2) a step of inserting a gene construct carrying JMJD3 and a desired transcription factor MYOD1 gene into a genome of a pluripotent stem cell;
   (3) a step of inserting a gene construct carrying JMJD3 into a genome of a pluripotent stem cell, followed by addition of a transcription factor MYOD1 to the cell;
   (4) a step of inserting a gene construct carrying JMJD3 and a gene construct carrying a transcription factor MYOD1 into a genome of a pluripotent stem cell;
   (5) a step of adding a transcription factor MYOD1 to a pluripotent stem cell having a histone in which H3K27me3 modification has been substantially removed or reduced;
   (6) a step of adding a transcription factor MYOD1 to a pluripotent stem cell in which JMJD3 is forcibly expressed; and
   (7) a step of adding JMJD3 and a transcription factor MYOD1 to a pluripotent stem cell.

6. A method of differentiating a pluripotent stem cell into a desired cell type according to claim 1, wherein the desired cell type is a nerve cell, comprising any one of the following steps (1) to (7):
   (1) a step of adding JMJD3 and a transcription factor NEUROG1, NEUROG2, NEUROG3, NEUROD1, and/or NEUROD2 to a pluripotent stem cell;
   (2) a step of inserting a gene construct carrying JMJD3 and a desired transcription factor NEUROG1, NEUROG2, NEUROG3, NEUROD1, and/or NEUROD2 gene into a genome of a pluripotent stem cell;
   (3) a step of inserting a gene construct carrying JMJD3 into a genome of a pluripotent stem cell, followed by addition of a transcription factor NEUROG1, NEUROG2, NEUROG3, NEUROD1, and/or NEUROD2 to the cell;
   (4) a step of inserting a gene construct carrying JMJD3 and a gene construct carrying a transcription factor NEUROG1, NEUROG2, NEUROG3, NEUROD1, and/or NEUROD2 into a genome of a pluripotent stem cell;
   (5) a step of adding a transcription factor NEUROG1, NEUROG2, NEUROG3, NEUROD1, and/or NEUROD2 to a pluripotent stem cell having a histone in which H3K27me3 modification has been substantially removed or reduced;
   (6) a step of adding a transcription factor NEUROG1, NEUROG2, NEUROG3, NEUROD1, and/or NEUROD2 to a pluripotent stem cell in which JMJD3 is forcibly expressed; and
   (7) a step of adding JMJD3 and a transcription factor NEUROG1, NEUROG2, NEUROG3, NEUROD1, and/or NEUROD2 to a pluripotent stem cell.

7. A method of differentiating a pluripotent stem cell into a desired cell type according to claim 1, wherein the desired cell type is a liver cell, comprising any one of the following steps (1) to (7):
   (1) a step of adding JMJD3 and a transcription factor HNF1A to a pluripotent stem cell;
   (2) a step of inserting a gene construct carrying JMJD3 and a desired transcription factor HNF1A gene into a genome of a pluripotent stem cell;
   (3) a step of inserting a gene construct carrying JMJD3 into a genome of a pluripotent stem cell, followed by addition of a transcription factor HNF1A to the cell;
   (4) a step of inserting a gene construct carrying JMJD3 and a gene construct carrying a transcription factor HNF1A into a genome of a pluripotent stem cell;
   (5) a step of adding a transcription factor HNF1A to a pluripotent stem cell having a histone in which H3K27me3 modification has been substantially removed or reduced;
   (6) a step of adding a transcription factor HNF1A to a pluripotent stem cell in which JMJD3 is forcibly expressed; and
   (7) a step of adding JMJD3 and a transcription factor HNF1A to a pluripotent stem cell.

* * * * *